United States Patent
Finkielsztein et al.

(10) Patent No.: US 10,383,971 B2
(45) Date of Patent: *Aug. 20, 2019

(54) HEMOSTATIC COMPOSITIONS AND THERAPEUTIC REGIMENS

(71) Applicant: Marine Polymer Technologies, Inc., Danvers, MA (US)

(72) Inventors: Sergio Finkielsztein, Newton, MA (US); John N. Vournakis, Charleston, SC (US)

(73) Assignee: Marine Polymer Technologies, Inc., Burlington, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 14/828,333

(22) Filed: Aug. 17, 2015

(65) Prior Publication Data
US 2016/0193379 A1   Jul. 7, 2016

Related U.S. Application Data

(60) Continuation of application No. 13/956,012, filed on Jul. 31, 2013, now Pat. No. 9,139,663, which is a
(Continued)

(51) Int. Cl.
*A61L 15/28* (2006.01)
*A61L 26/00* (2006.01)
(Continued)

(52) U.S. Cl.
CPC ............ *A61L 15/28* (2013.01); *A61L 15/20* (2013.01); *A61L 15/44* (2013.01); *A61L 26/0066* (2013.01); *A61L 27/54* (2013.01); *C08B 37/0024* (2013.01); *C08J 3/28* (2013.01); *C08L 5/08* (2013.01); *A61L 2300/23* (2013.01);
(Continued)

(58) Field of Classification Search
CPC ............. A61L 26/0066; A61L 27/54; A61L 2300/404; A61L 2300/414; A61L 15/20; A61L 15/44; A61L 15/28; A61L 2300/23; A61L 2430/34; C08L 5/08; C08J 3/28;
(Continued)

(56) References Cited

U.S. PATENT DOCUMENTS 3,988,411 A   10/1976   Capozza
3,989,535 A   11/1976   Capozza
(Continued)

FOREIGN PATENT DOCUMENTS

CA   2072395   1/1993
DE   19821598   11/1999
(Continued)

OTHER PUBLICATIONS

U.S. Appl. No. 09/875,846, filed Jun. 6, 2001, Vournakis et al.
(Continued)

*Primary Examiner* — Nicole P Babson
(74) *Attorney, Agent, or Firm* — Jones Day

(57) ABSTRACT

The present invention relates generally to the field of hemostasis, including methods, compositions, and devices that can be employed to treat wounds. More specifically the present invention relates to hemostatic compositions that reduce the need for, and cost of, nursing care of patients with chronic wounds by reducing the frequency of wound dressing changes.

Figure 1:
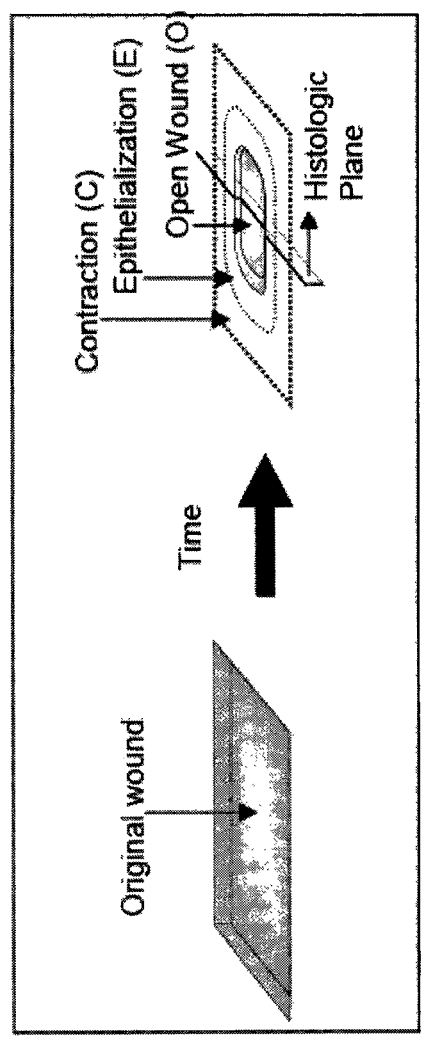

27 Claims, 51 Drawing Sheets
Specification includes a Sequence Listing.

Related U.S. Application Data division of application No. 12/033,670, filed on Feb. 19, 2008, now Pat. No. 8,871,247.

(60) Provisional application No. 60/901,826, filed on Feb. 19, 2007.

(51) Int. Cl.

| | |
|---|---|
| *A61L 27/54* | (2006.01) |
| *C08J 3/28* | (2006.01) |
| *C08L 5/08* | (2006.01) |
| *A61L 15/20* | (2006.01) |
| *A61L 15/44* | (2006.01) |
| *C08B 37/00* | (2006.01) |

(52) U.S. Cl.
CPC ... *A61L 2300/404* (2013.01); *A61L 2300/414* (2013.01); *A61L 2430/34* (2013.01); *C08J 2305/08* (2013.01); *Y10T 428/298* (2015.01)

(58) Field of Classification Search
CPC .............. C08J 2305/08; C08B 37/0024; Y10T 428/298
See application file for complete search history.

(56) References Cited

U.S. PATENT DOCUMENTS

| | | |
|---|---|---|
| 4,068,757 A | 1/1978 | Casey |
| 4,195,175 A | 3/1980 | Peniston et al. |
| 4,378,017 A | 3/1983 | Kosugi et al. |
| 4,394,373 A | 7/1983 | Malette et al. |
| 4,532,134 A | 7/1985 | Malette et al. |
| 4,575,519 A | 3/1986 | Kifune et al. |
| 4,605,623 A | 8/1986 | Malette et al. |
| 4,699,135 A | 10/1987 | Motosugi et al. |
| 4,749,620 A | 6/1988 | Rha et al. |
| 4,803,168 A | 2/1989 | Jarvis, Jr. |
| 4,895,724 A | 1/1990 | Cardinal et al. |
| 4,942,129 A | 7/1990 | Goosen et al. |
| 5,008,116 A | 4/1991 | Cahn |
| 5,057,540 A | 10/1991 | Kensil et al. |
| 5,071,977 A | 12/1991 | Cassels et al. |
| 5,093,319 A | 3/1992 | Higham et al. |
| 5,116,747 A | 5/1992 | Moo-Young et al. |
| 5,219,749 A | 6/1993 | Bouriotis et al. |
| 5,229,123 A | 7/1993 | Masubuchi et al. |
| 5,252,468 A | 10/1993 | Fujishima et al. |
| 5,447,505 A | 9/1995 | Valentine et al. |
| 5,457,141 A | 10/1995 | Matsuda et al. |
| 5,510,102 A | 4/1996 | Cochrum |
| 5,529,914 A | 6/1996 | Hubbell et al. |
| 5,541,186 A | 7/1996 | Breu et al. |
| 5,550,110 A | 8/1996 | Cody et al. |
| 5,571,821 A | 11/1996 | Chan et al. |
| 5,573,934 A | 11/1996 | Hubbell et al. |
| 5,622,834 A | 4/1997 | Vournakis et al. |
| 5,623,064 A | 4/1997 | Vournakis et al. |
| 5,624,679 A | 4/1997 | Vournakis et al. |
| 5,635,493 A | 6/1997 | Vournakis et al. |
| 5,641,752 A | 6/1997 | Cody et al. |
| 5,658,943 A | 8/1997 | Berryman et al. |
| 5,686,115 A | 11/1997 | Vournakis et al. |
| 5,731,298 A | 3/1998 | Reinmuller et al. |
| 5,811,416 A | 9/1998 | Chwalisz et al. |
| 5,846,952 A | 12/1998 | Vournakis et al. |
| 5,858,350 A | 1/1999 | Vournakis et al. |
| 5,871,985 A | 2/1999 | Aebischer et al. |
| 5,916,907 A | 6/1999 | Bird |
| 6,046,179 A | 4/2000 | Murch et al. |
| 6,063,911 A | 5/2000 | Vournakis et al. |
| 6,080,866 A | 6/2000 | Spurr |
| 6,162,241 A | 12/2000 | Coury et al. |
| 6,599,720 B2 | 7/2003 | Vournakis et al. |
| 6,610,668 B2 | 8/2003 | Vournakis et al. |
| 6,630,459 B2 | 10/2003 | Vournakis et al. |
| 6,649,599 B2 | 11/2003 | Vournakis et al. |
| 6,686,342 B2 | 2/2004 | Vournakis et al. |
| 6,743,783 B1 | 6/2004 | Vournakis et al. |
| 6,864,245 B2 | 3/2005 | Vournakis et al. |
| 7,037,983 B2 | 5/2006 | Huang et al. |
| 7,041,657 B2 | 5/2006 | Vournakis et al. |
| 7,074,175 B2 | 7/2006 | Handy et al. |
| 7,115,588 B2 | 10/2006 | Vournakis et al. |
| 7,140,882 B2 | 11/2006 | Ito |
| 7,148,209 B2 | 12/2006 | Hoemann et al. |
| 7,157,079 B2 | 1/2007 | Nielsen et al. |
| 7,285,266 B2 | 10/2007 | Vournakis et al. |
| 7,307,157 B2 | 12/2007 | Yoshii et al. |
| 7,371,403 B2 | 5/2008 | McCarthy et al. |
| 7,691,832 B2 | 4/2010 | Haty |
| 7,704,522 B2 | 4/2010 | Morgan |
| 7,931,637 B2 | 4/2011 | Vournakis et al. |
| 8,152,750 B2 | 4/2012 | Vournakis et al. |
| 8,258,117 B2 | 9/2012 | Hoemann et al. |
| 8,318,210 B2 | 11/2012 | Tengler et al. |
| 8,481,512 B2 | 7/2013 | Vournakis et al. |
| 8,748,390 B2 | 6/2014 | Schlom et al. |
| 8,802,083 B2 | 8/2014 | Vournakis et al. |
| 8,835,408 B2 | 9/2014 | Vournakis et al. |
| 8,858,964 B2 | 10/2014 | Vournakis et al. |
| 8,859,528 B2 | 10/2014 | Vournakis et al. |
| 8,871,247 B2 | 10/2014 | Finkielsztein et al. |
| 8,926,944 B2 | 1/2015 | Serda et al. |
| 8,992,453 B2 | 3/2015 | Vournakis et al. |
| 9,139,663 B2 | 9/2015 | Finkielsztein et al. |
| 9,139,664 B2 | 9/2015 | Finkielsztein et al. |
| 9,198,928 B2 | 12/2015 | Vournakis et al. |
| 9,320,653 B2 | 4/2016 | Vournakis et al. |
| 9,642,871 B2 | 5/2017 | Vournakis et al. |
| 2002/0082220 A1 | 6/2002 | Hoemann et al. |
| 2002/0197269 A1 | 12/2002 | Lingnau et al. |
| 2003/0104020 A1 | 6/2003 | Davison et al. |
| 2003/0144347 A1 | 6/2003 | Ryack et al. |
| 2003/0185845 A1 | 10/2003 | Klysner et al. |
| 2004/0087015 A1 | 5/2004 | Vournakis et al. |
| 2004/0091493 A1 | 5/2004 | Perrier et al. |
| 2004/0220140 A1 | 11/2004 | Vournakis et al. |
| 2004/0243043 A1 | 12/2004 | McCarthy et al. |
| 2004/0254244 A1 | 12/2004 | Kono et al. |
| 2005/0004072 A1 | 1/2005 | Vournakis et al. |
| 2005/0013812 A1 | 1/2005 | Dow et al. |
| 2005/0113773 A1 | 5/2005 | Yoshii et al. |
| 2006/0051432 A1 | 3/2006 | Morgan |
| 2006/0105049 A1 | 5/2006 | Fernandes et al. |
| 2006/0127873 A1 | 6/2006 | Hoemann et al. |
| 2006/0172000 A1 | 8/2006 | Cullen et al. |
| 2007/0021703 A1 | 1/2007 | McCarthy |
| 2007/0036846 A1 | 2/2007 | Tsang |
| 2007/0037737 A1 | 2/2007 | Hoemann et al. |
| 2007/0072826 A1 | 3/2007 | Vournakis et al. |
| 2007/0081972 A1 | 4/2007 | Sandler et al. |
| 2007/0085059 A1 | 4/2007 | Mora-Gutierrez et al. |
| 2007/0105815 A1 | 5/2007 | Vournakis et al. |
| 2007/0148215 A1 | 6/2007 | Teslenko et al. |
| 2007/0148437 A1 | 6/2007 | Muller-Schulte |
| 2007/0184023 A1 | 8/2007 | Rasmussen et al. |
| 2007/0237812 A1 | 10/2007 | Patel et al. |
| 2008/0026064 A1 | 1/2008 | Vournakis et al. |
| 2008/0207561 A1 | 8/2008 | Utecht et al. |
| 2008/0299147 A1 | 12/2008 | Dillon et al. |
| 2009/0075383 A1 | 3/2009 | Buschmann et al. |
| 2009/0117175 A1 | 5/2009 | Finkielsztein et al. |
| 2009/0130186 A1 | 5/2009 | McCarthy et al. |
| 2009/0149421 A1 | 6/2009 | Buschmann et al. |
| 2009/0202430 A1 | 8/2009 | Hoemann et al. |
| 2009/0247738 A1 | 10/2009 | Vournakis et al. |
| 2009/0304803 A1 | 12/2009 | Hasan |
| 2009/0318383 A1 | 12/2009 | Vournakis et al. |
| 2010/0021514 A1 | 1/2010 | Fugmann |
| 2010/0040694 A1 | 2/2010 | Na et al. |
| 2010/0086613 A1 | 4/2010 | Wu |
| 2010/0105139 A1 | 4/2010 | Spanjaard et al. |
| 2010/0150960 A1 | 6/2010 | Schlom et al. |

(56) References Cited

U.S. PATENT DOCUMENTS

| | | |
|---|---|---|
| 2010/0323986 A1 | 12/2010 | Vournakis et al. |
| 2011/0250225 A1 | 10/2011 | Fotin-Mleczek et al. |
| 2011/0293704 A1 | 12/2011 | Holst et al. |
| 2011/0313056 A1 | 12/2011 | Buschmann et al. |
| 2012/0164174 A1 | 6/2012 | Sung et al. |
| 2012/0321721 A1 | 12/2012 | Ouyang et al. |
| 2013/0004474 A1 | 1/2013 | Ouyang et al. |
| 2013/0084340 A1 | 4/2013 | Tengler et al. |
| 2013/0210717 A1 | 8/2013 | Merzouki et al. |
| 2013/0287853 A1 | 10/2013 | Vournakis et al. |
| 2013/0337037 A1 | 12/2013 | Finkielsztein et al. |
| 2014/0051849 A1 | 2/2014 | Finkielsztein et al. |
| 2014/0093577 A1 | 4/2014 | Tengler et al. |
| 2014/0127310 A1 | 5/2014 | Vournakis et al. |
| 2014/0287029 A1 | 9/2014 | Schlom et al. |
| 2014/0350449 A1 | 11/2014 | Vournakis et al. |
| 2014/0351961 A1 | 11/2014 | Asea |
| 2014/0363495 A1 | 12/2014 | Schlom et al. |
| 2014/0363673 A1 | 12/2014 | Minami et al. |
| 2015/0024014 A1 | 1/2015 | Finkielsztein et al. |
| 2015/0037427 A1 | 2/2015 | Benita et al. |
| 2015/0087689 A1 | 3/2015 | Merzouki et al. |
| 2015/0118281 A1 | 4/2015 | Vournakis et al. |
| 2015/0140045 A1 | 5/2015 | Vournakis et al. |
| 2015/0314036 A1 | 11/2015 | O'Keeffe et al. |
| 2016/0015748 A1 | 1/2016 | Caligiuri et al. |
| 2016/0030465 A1 | 2/2016 | Finkielsztein et al. |
| 2017/0128382 A1 | 5/2017 | Vournakis et al. |
| 2017/0304354 A1 | 10/2017 | Vournakis et al. |
| 2018/0099003 A1 | 4/2018 | Vournakis et al. |

FOREIGN PATENT DOCUMENTS

| | | |
|---|---|---|
| EP | 0392396 | 10/1990 |
| EP | 0426368 | 5/1991 |
| EP | 0543572 | 5/1993 |
| EP | 0544000 | 6/1993 |
| EP | 0731812 | 9/1996 |
| EP | 1139752 | 10/2001 |
| EP | 1306390 A1 | 5/2003 |
| FR | 2 736 835 | 1/1997 |
| GB | 2220211 | 1/1990 |
| GB | 1038367 | 8/1996 |
| JP | 55-152705 | 11/1980 |
| JP | 56-131639 | 10/1981 |
| JP | 56-133344 | 10/1981 |
| JP | 58-088424 | 5/1983 |
| JP | 58-220899 | 12/1983 |
| JP | 60-025003 | 2/1985 |
| JP | 60-208302 | 10/1985 |
| JP | 60-215003 | 10/1985 |
| JP | 61-253065 | 11/1986 |
| JP | 62-288602 | 12/1987 |
| JP | 63-503466 | 12/1988 |
| JP | 01-167301 | 7/1989 |
| JP | 02-006501 | 1/1990 |
| JP | 02-225539 | 9/1990 |
| JP | 02-235905 | 9/1990 |
| JP | 02-240101 | 9/1990 |
| JP | 03-167201 | 7/1991 |
| JP | 03-204812 | 9/1991 |
| JP | 04-041422 | 2/1992 |
| JP | 04-126701 | 4/1992 |
| JP | A-H04-371161 | 12/1992 |
| JP | 05-025289 | 2/1993 |
| JP | 05-032702 | 2/1993 |
| JP | 05-051465 | 3/1993 |
| JP | 05-502267 | 4/1993 |
| JP | 05-235905 | 9/1993 |
| JP | 05-271094 | 10/1993 |
| JP | A-H07-102458 | 4/1995 |
| JP | 9506126 | 6/1997 |
| JP | 2002-512195 | 4/2002 |
| JP | 2003-128704 | 5/2003 |
| JP | 2003-160602 | 6/2003 |
| JP | 2005-509059 | 4/2005 |
| JP | 2005-281239 | 10/2005 |
| JP | 2006-518764 | 8/2006 |
| JP | 2008-019264 | 1/2008 |
| NZ | 277662 | 4/1998 |
| WO | WO 1987/07618 | 12/1987 |
| WO | WO 1992/03480 | 3/1992 |
| WO | WO 1992/04408 | 3/1992 |
| WO | WO 1993/08799 | 5/1993 |
| WO | WO 1993/09176 | 5/1993 |
| WO | WO 1993/12875 | 7/1993 |
| WO | WO 1994/03483 | 2/1994 |
| WO | WO 95/15343 | 6/1995 |
| WO | WO 1995/15343 | 6/1995 |
| WO | WO 1996/11927 | 4/1996 |
| WO | WO 1996/19459 | 6/1996 |
| WO | WO 96/20698 A2 | 7/1996 |
| WO | WO 1996/39122 | 12/1996 |
| WO | WO 1997/08169 | 3/1997 |
| WO | WO 1997/37987 | 10/1997 |
| WO | WO 97/40679 A1 | 11/1997 |
| WO | WO 98/17693 A1 | 4/1998 |
| WO | WO 98/52605 A1 | 11/1998 |
| WO | WO 99/36089 A1 | 7/1999 |
| WO | WO 99/36090 A1 | 7/1999 |
| WO | WO 2000/36918 | 6/2000 |
| WO | WO 2002/000272 A2 | 1/2002 |
| WO | WO 2002/063961 | 8/2002 |
| WO | WO 2003/022360 A2 | 3/2003 |
| WO | WO 2003/042251 | 5/2003 |
| WO | WO 2004/006961 A1 | 1/2004 |
| WO | WO 2004/024196 | 3/2004 |
| WO | WO 2004/060172 | 7/2004 |
| WO | WO 2004/076637 | 9/2004 |
| WO | WO 2005/027993 | 3/2005 |
| WO | WO 2005/063311 | 7/2005 |
| WO | WO 2006/062723 A2 | 6/2006 |
| WO | WO 2006/066752 | 6/2006 |
| WO | WO 2007/051311 A1 | 5/2007 |
| WO | WO 2007/059605 | 5/2007 |
| WO | WO 2007/109812 | 9/2007 |
| WO | WO 2007/109813 | 9/2007 |
| WO | WO 2008/039390 A2 | 4/2008 |
| WO | WO 2008/103345 | 8/2008 |
| WO | WO 2009/095456 | 8/2009 |
| WO | WO 2009/097545 A1 | 8/2009 |
| WO | WO 2010/037408 A1 | 4/2010 |
| WO | WO 2010/088565 A1 | 8/2010 |
| WO | WO 2011/060544 A1 | 5/2011 |
| WO | WO 2011/060545 A1 | 5/2011 |
| WO | WO 2011/060555 A1 | 5/2011 |
| WO | WO 2011/130646 | 10/2011 |
| WO | WO 2011/140638 A1 | 11/2011 |
| WO | WO 2011/144358 A1 | 11/2011 |
| WO | WO 2012/061803 | 5/2012 |
| WO | WO 2012/142581 | 10/2012 |
| WO | WO 2012/159215 A1 | 11/2012 |
| WO | WO 2014/165302 | 10/2014 |
| WO | WO 2014/197970 A1 | 12/2014 |
| WO | WO 2015/061416 A2 | 4/2015 |
| WO | WO 2015/110656 A1 | 7/2015 |
| WO | WO 2015/123778 A1 | 8/2015 |
| WO | WO 2015/123779 A1 | 8/2015 |

OTHER PUBLICATIONS

Aebischer, P. et al., 1993, "Cell Encapsulation for the Nervous System," in *Fundamentals of Animal Cell Encapsulation and Immobilization*, CRC Press, pp. 197-224.

Andrews et al. 1999, "The role of zinc in wound healing." Adv Wound Care. 12(3):137-8.

ASTM Committee F04 on Medical and Surgical Materials and Devices, 2001, "Designation F2103-01: Standard Guide for Characterization and Testing of Chitosan Salts as Starting Materials Intended for Use in Biomedical and Tissue-Engineered Medical Product Applications," ASTM International, pp. 1-8.

(56) References Cited

OTHER PUBLICATIONS

Austin, P.R. and Sennett, S., 1986, "Dry Chitosan Salts and Complexes of Aliphatic Carboxylic Acids," in *Chitin in Nature and Technology*, Muzzarelli et al., eds., Plenum Press, New York, pp. 279-286.
Azuma, 2012, "alpha-Chitin Nanofibrils Improve Inflammatory and Fibrosis Responses in Inflammatory Bowel Disease Mice Model," Carbohydrate Polymers 90:197-200.
Azuma, 2012, "Beneficial and Preventive Effect of Chitin Nanofibrils in a Dextran Sulfate Sodium-induced Acute Ulcerative Colitis Model," Carbohydrate Polymers 87:1399-1403.
Barbosa et al., 2010, "Evaluation of the effect of the degree of acetylation on the inflammatory response to 3D porous chitosan scaffolds," J Biomed Mater Res A. 93(1):20-28.
Battistini, B. et al., 1993, "Growth Regulatory Properties of Endothelins," Peptides, 14:385-399.
Beauman, J.G. et al., 2005, "Genital herpes: a review," Am Fam Physician, 72(8):1527-34.
Bell, K.M. et al., 1995, "Effect of Endothelin-1 and Sarafotoxin S6c on Blood Flow in a Rat Tumor," J. Cardiovasc. Pharmacol., 26(Suppl. 3):S222-S225.
Berkeley, R.C.W. et al., 1979, "Chitin, Chitosan and their Degradative Enzymes," in *Microbial Polysaccharides and Polysaccharases*, Berkeley et al., eds., Academic Press, pp. 205-216.
Bissett, 2006, "Glucosamine: an Ingredient with Skin and Other Benefits," J. Cosm. Dermatol. 5:309-315.
Blackwell, J. et al., 1967, "Chitin Fibers of the Diatoms Thalassiosira fluviatilis and Cyclotella cryptica," J. Mol. Biol., 28:383-385.
Blackwell, J., 1988, "Physical Methods for the Determination of Chitin Structure and Conformation," Meth. Enz., 161:435-442.
Bodmeier, R. et al., 1989, "A Novel Approach to the Oral Delivery of Micro- or Nanoparticles," Pharm. Res., 6(5):413-417.
Carreno-Gomez, B. & Duncan, R., 1997, "Evaluation of the Biological Properties of Soluble Chitosan and Chitosan Microspheres," Int. J. Pharma., 148:231-240.
Chhabra, 2004, "Antimicrobial and antioxidant properties of chitosan," Thesis Submitted to the Graduate Faculty of the University of Georgia.
Choi, W.S. et al., 2002, "Preparation of Chitosan Oligomers by Irradiation," Polym. Degrad. Stab., 78:533-538.
Clozel, M. et al., 1994, "Pharmacological Characterization of Bosentan, a New Potent Orally Active Nonpeptide Endothelin Receptor Antagonist," J. Pharmacol. Exp. Ther., 270(1): 228-235.
Dai et al., 2009, "Chitosan acetate bandage as a topical antimicrobial dressing for infected burns," Antimicrobial Agents and Chemotherapy, 53(2):393-400.
Davis, M. and Preston, J.F., 1981, "A Simple Modified Carbodiimide Method for Conjugation of Small Molecular Weight Compounds to Immunoglobulin G with Minimal Protein Crosslinking," Anal. Biochem., 116:402-407.
Diaz-Visurraga et al., 2010, "Lethal effect of chitosan-Ag (I) films on *Staphylococcus aureus* as evaluated by electron microscopy," J Applied Microbiol. 108:633-646.
Ding et al., 2014, "Emerging Chitin and Chitosan Nanofibrous Materials for Biomedical Applications," Nanoscale 6:9477-9493.
Domard, A., 1986, "Circular Dichroism Study on N-acetylglucosamine Oligomers," Int. J. Macromol., 8:243-246.
Dong, C. and Rogers, J.A., 1991, "Polymer-coated Liposomes: Stability and Release of ASA from Carboxymethyl Chitin Coated Liposomes," Journal of Controlled Release, 17:217-224.
European Search Report issued for EP Application No. EP 12153634.6 dated Jun. 15, 2012.
Falk, M. et. al., 1966, "Studies on Chitin (β-(1-4)-linked 2-acetamido-2-deoxy-D-glucan) Fibers of the Diatom Thalassiosira fluviatilis hustedt," Can. J. Chem., 44: 2269-2281.
Fine et al., 1991, "Revised Clinical and Laboratory Criteria for Subtypes of Inherited Epidermolysis Bullosa: A Consensus Report by the Subcommittee on Diagnosis and Classification of the National Epidermolysis Bullosa Registry," Journal of the American Academy of Dermatology, 24(1):119-35.
Fischer et al., 2004, "Comparison of Structural and Hemostatic Properties of the Poly-N-Acetyl Glucosamine Syvek Patch with Products Containing Chitosan," Microsc. Res. Tech. 63:168-174.
Fischer et al., 2005, "Synergistic Platelet Integrin Signaling and Factor XII activation in poly-N-acetyl Glucosamine Fiber-mediated hemostasis," Biomaterials 26:5433-5443.
Fischer et al., 2007, "Hemostatic Properties of Glucosamine-based Materials," Journal of Biomedical Materials Research 80A: 167-174.
Fujimoto et al., 2006, "Antibacterial effects of Chitosan solution® against *Legionella pneumophila, Escherichia coli*, and *Staphylococcus aureus*," Intl J Food Microbiol. 112:96-101.
Gomez-Garre, D. et al., 1996, "An Orally Active $ET_A/ET_B$ Receptor Antagonist Ameliorates Proteinuria and Glomerular Lesions in Rats with Proliferative Nephritis," Kidney Intl., 50:962-972.
Goodwin, A.T. et al., 1998, "Role of Endogenous Endothelin in the Regulation of Basal Coronary Tone in the Rat," J. Physiol., 511(2):549-557.
Groboillot, A.F. et al., 1993, "Membrane Formation by Interfacial Cross-linking of Chitosan for Microencapsulation of *Lactococcus lactis*," Biotech. and Bioeng., 42(10):1157-1163.
Halaban, R., 1996, "Growth Factors and Melanomas," Seminars in Oncology, 23:673-681.
Harrington et al., 2002, "Cells as vehicles for cancer gene therapy: the missing link between targeted vectors and systemic delivery?" Hum Gene Ther. 13(11):1263-80.
Hazrati et al., 2006, "Human α- and βDefensins Block Multiple Steps in Herpes Simplex Virus Infection," J. Immunol 177:8658-66.
Hirano, S. et al., 1976, "Selective N-acylation of Chitosan," Carbohydrate Research, 47:315-320.
Hirano, S. et al., 1981, "SEM Ultrastructure Studies of N-acyl- and N-benzylidene-chitosan and Chitosan Membranes," J. Biomed. Mat. Res. 15:903-911.
Hirano, S. et al., 1990, "The Regulation of Serum Cholesterol Level by Oral Administration of Chitosan in Rabbits," Proceedings of the International Symposium of Chitin Derivatives in Life Sciences, Oct. 5-7, pp. 115-120.
Hirano, S., 1989, "Production and Application of Chitin and Chitosan in Japan," in *Chitin and Chitosan*, Skjak-Brack, Anthosen, and Sanford, eds. Elsevier Science Publishing Co., pp. 37-43.
Hirsch et al., 2009, "Human Beta-Defensin-3 Promotes Wound Healing in Infected Diabetic Wounds," The Journal of Gene Medicine, 11:220-8.
Hocher, B. et al., 1997, "The Paracrine Endothelial System: Pathophysiology and Implications in Clinical Medicine," Eur. J. Chem. Clin. Biochem., 35:175-189.
Howell, et al., 2007, "Antiviral Activity of Human Beta-defensin 3 against vaccinia virus," J. Allergy and Clini. Immuno. 119(4):1022-25.
Huang, Y.C. et al., 2005, "Pulmonary Inflammation Caused by Chitosan Microparticles," J. Biomed. Mater. Res. Part A, 75(2):283-287.
Hwang, C. et al., 1985, "Encapsulation with Chitosan: Transmembrane Diffusion of Proteins in Capsules," in *Chitin in Nature and Technology*, Muzzareli, R. et al., eds., Plenum Press, pp. 389-396.
IBA Indus Trial, 2007, "IBA Solutions in Cancer Diagnosis, Therapy. Sterilization and Ionization Solutions for Hygiene and Safety. Material Applications," http://www.iba-worldwide.com/industrial/applications/material/index.php.
International Preliminary Report of Patentability of International Application No. PCT/US2011/032709 (published as WO 2011/130646), dated Oct. 26, 2012.
International Search Report for International App. No. PCT/US2008/002172 (published as WO 2008/103345), dated Aug. 7, 2009.
International Search Report for International App. No. PCT/US2011/032709 (published as WO 2011/130646), dated Aug. 15, 2011.
International Search Report for International App. No. PCT/US2012/033782 (published as WO 2012/142581), dated Aug. 20, 2012.
International Search Report for International App. No. PCT/US2014/025623 (published as WO 2014/165302), dated Jul. 10, 2014.

(56) References Cited

OTHER PUBLICATIONS

Ishihara, M. et al., 2002, "Photocrosslinkable Chitosan as a Dressing for Wound Occlusion and Accelerator in Healing Process," Biomaterials, 23:833-840.

Jiang, Y. et al., 2009, "Expression of mouse beta-defensin-3 in MDCK cells and its anti-influenza-virus activity," Arch Virol. 154(4):639-47.

Johnson, R.S. et al, 1992, "In Vivo Tissue Response to Implanted Chitosan Glutamate," in *Advances in Chitin and Chitosan*, Brine, C.J. et al., eds., Elsevier Publishers, Ltd., pp. 3-8.

Kazakos et al., 2007, "Activity of human beta-defensin 3 against metallo-beta-lactamase-producing *Pseudomonas aeruginosa* strains" [online], European Society of Clinical Microbiology and Infectious Diseases [retrieved on Sep. 12, 2013]. Retrieved from the Internet <URL: http://www.blackwellpublishing.com/eccmid17/abstract.asp?id=56248>.

Kenny, B. et al., 1997, "Pharmacological Options in the Treatment of Benign Prostatic Hyperplasia," J. Medicinal Chem., 40:1293-1315.

Kikuchi, K. et al., 1996, "Decreased $ET_B$ Receptor Expression in Human Metastatic Melanoma Cells," Biochem. Biophys. Res. Comm., 219:734-739.

Komai, T. et al., 1986, "Biomedical Evaluation of Acylated Chitins as Coating Materials," in *Chitin in Nature and Technology*, Muzzarelli et al., eds., Plenum Press, New York, pp. 497-506.

Kurita, K. and Inoue, S., 1989, "Preparation of Indo-chitins and Graft Copolymerization onto the Derivatives," in *Chitin and Chitosan*, Skjak-Braek et al, Elsevier Science Publishing Co., Inc., pp. 365-372.

Kurita, K. et al., 1990, "Preparations of Soluble Chitin Derivatives and the Modifications to Branched Chitins," Polym. Prep. (Am. Chem. Soc., Div. Polym. Chem.), 31:624-625.

Lindner et al., 2011, "Anti bacterial effects of poly-N-acetylglucosamine nanofibers in cutaneous wound healing: requirement for Akt1," PLoS One 6(4):E18996. DOI: 10.1371/JOURNAL.PONE.0018996.

Liu et al., 2001, "Antibacterial action of chitosan and carboxymethylated chitosan," Journal of Applied Polymer Science 79:1324-1335.

Liu et al., 2004, "Chitosan kills bacteria through cell membrane damage," Intl J Food Microbiol. 95:147-155.

Lundblad, R. et al., 1996, "Granulocyte Colony-Stimulating Factor Improves Survival Rate and Reduces Concentrations of Bacteria, Endotoxin, Tumor Necrosis Factor, and Endothelin-1 in Fulminant Intra-Abdominal Sepsis in Rats," Crit. Care Med., 24:820-826.

Lüscher, T.F. and Wenzel, R.R., 1995, "Endothelin and Endothelin Antagonists: Pharmacology and Clinical Implications," in *Mediators in the Cardiovascular System: Regional Ischemia*, Birkhäuser Verlag, Basel, Switzerland, pp. 237-253.

Mann et al. 2006, "Unsaturated N-Acetyl- D-Glucosaminuronic Acid Glycosides as Inhibitors of Influenza Virus Sialidase," Glycoconj J. 23(1-2):127-33.

Mao et al. 2001, "Chitosan-DNA nanoparticles as gene carriers: synthesis, characterization and transfection efficiency," J Control Release 70(3):399-421.

Maresch, G. et al., 1989, "Hydroxypropylation of Chitosan," in *Chitin and Chitosan*, Skjak-Braek, Anthosen, and Sanford, eds., Elsevier Science Publishing Co., pp. 389-395.

Markewitz, B.A. et al., 1995, "Endothelin-1 Synthesis, Receptors, and Signal Transduction in Alveolar Epithelium: Evidence for an Autocrine Role," Am. J. Physiol., 268:L192-L200.

Mated, A.O. and De Artiñano, M.A., 1997, "Highlights on Endothelins: A Review," Pharmacol. Res., 36(5):339-351.

Matsuhashi, S. and Kume, T., 1997, "Enhancement of Antimicrobial Activity of Chitosan by Irradiation," J. Sci. Food Agric., 73:237-241.

Matthew, H.W. et al., 1993, "Complex Coacervate Microcapsules for Mammalian Cell Culture and Artificial Organ Development," BioTechnol. Prog., 9(5):510-519.

McCurdy, J.D., 1992, "FDA and the Use of Chitin and Chitosan Derivatives," in *Advances in Chitin and Chitosan*, Brine, C.J. et al., eds., Elsevier Publishers, Ltd., pp. 659-662.

McLachlan and Craigne, 1966, "Chitin Fibers in Cyclotella cryptica and Growth of C. cryptica and Thalassiosira fluviatilis," Some Contemp. Stud. Mar. Sci., pp. 511-517.

McLachlan, A.G. et al., 1965, "Studies on the Chitin (chitin: poly-N-acetylglucosamine) Fibers of the Diatom Thalassiosira fluviatilis hustedt," Can. J. Botany, 43:707-713.

Mezzana, 2008, "Clinical Efficacy of a New Chitin Nanofibrils-based Gel in Wound Healing," Acta Chirurgiae Plasticae 50(3):81-84.

Middleton, J.C. and Tipton, A.J., 1998, "Materials: Synthetic Biodegradable Polymers as Medical Devices," http://www.devicelink.com/mpb/archive/98/03/002.html.

Min, B.M. et al., 2004, "Chitin and Chitosan Nanofibers: Electrospirming of Chitin and Deacetylation of Chitin Nanofibers," Polymer, 45:7137-7142.

Minami, S. et al., 1996, "Chitosan-Inducing Hemorrhagic Pneumonia in Dogs," Carb. Polymers., 29:241-246.

Mireles, C. et al., 1992, "Complex Formation of Chitosan and Naturally Occurring Polyanion," in *Advances in Chitin and Chitosan*, Brine, C.J. et al., eds., Elsevier Publishers, Ltd., pp. 506-515.

Moraitis, S. et al., 1997, "Endothelin Expression and Responsiveness in Human Ovarian Carcinoma Cell Lines," Eur. J. Cancer, 33:661-668.

Morbidelli, L. et al., 1995, "Proliferation and Migration of Endothelial Cells is Promoted by Endothelins via Activation of $ET_B$ Receptors," Am. J. Physiol., 269:H686-H695.

Morganti & Morganti, 2008, "Chitin Nanofibrils for Advanced Cosmeceuticals," Clinics in Dermatology 26:334-340.

Morganti et al., 2011, "Transforming Nanostmctured Chitin from Crustacean Waste into Beneficial Health Products: a Must for our Society," Nanotechnology, Science and Applications 4:123-129.

Nelson, J.B. et al., 1996, "Endothelin-1 Production and Decreased Endothelin B Receptor Expression in Advanced Prostate Cancer," Cancer Res., 56:663-668.

Nishi, N. et al., 1986, "Preparation and Characterization of Phosphorylated Chitin and Chitosan," in *Chitin in Nature and Technology*, Muzzarelli et al., Plenum Press, New York, pp. 297-299.

No et al., 2002, "Antibacterial activity of chitosans and chitosan oligomers with different molecular weights," Intl J Food Microbiol. 74:65-72.

Noguchi, J. et al., 1969, "Chitosan Epichlorohydrin Anion Exchange Resin with Primary Amines as Absorption Site," Kogyo Kagaku Zasshi, 72:796-799.

Obara, K. et al., 2005, "Acceleration of Wound Healing in Healing-Impaired db/db Mice with a Photocrosslinkable Chitosan Hydrogel Containing Fibroblast Growth Factor-2," Wound Repair Regen., 13(4):390-397.

Office Action dated Aug. 30, 2011 issued in U.S. Appl. No. 12/033,670 (now U.S. Pat. No. 8,871,247).

Office Action dated Dec. 6, 2010 issued in U.S. Appl. No. 12/033,670 (now U.S. Pat. No. 8,871,247).

Office Action dated Sep. 17, 2014 issued in U.S. Appl. No. 13/956,012 (now U.S. Pat. No. 9,139,663).

Office Action dated Sep. 18, 2014 issued in U.S. Appl. No. 13/956,035 (now U.S. Pat. No. 9,139,664).

Ohlstein, E.H. et al., 1996, "Endothelin Receptors: Receptor Classification, Novel Receptor Antagonists, and Potential Therapeutic Targets," Medicinal Res. Rev., 16:365-390.

Oikawa, T. et al., 1994, "Production of Endothelin-1 and Thrombomodulin by Human Pancreatic Cancer Cells," Br. J. Cancer, 69:1059-1064.

Parris, R.J. and Webb, D.L., 1997, "The Endothelin System in Cardiovascular Physiology and Pathophysiology," Vascular Med., 2:31-43.

Patel, K.V. and Schrey, M.P., 1995, "Human Breast Cancer Cells Contain a Phosphoramidon-Sensitive Metalloproteinase which Can Process Exogenous Big Endothelin-1 to Endothelin-1: A Proposed Mitogen for Human Breast Fibroblasts," Brit. J. Cancer, 71:442-447.

(56) References Cited

OTHER PUBLICATIONS

Paul, W. and Sharma, C.P., 2004, "Chitosan and Aiginate Wound Dressings: A Short Review," Trends Biomater. Artif. Organs, 18(1):18-23.
Perkins et al., 2010, "Poly-N-acetylglucosamine nanofibers from a marine diatom promote wound healing and defensin expression in an AKT1-dependent manner," Abstracts of Papers American Chemical Society 239:527.
Pietramaggiori et al., 2008, "Effects of poly-N-acetyl glucosamine (pGlcNAc) patch on wound healing in db/db mouse," The Journal of Trauma Injury, Infection, and Critical Care 64(3):803-808.
Polk, A. et al., 1994, "Controlled Release of Albumin from Chitosan-alginate Microcapsules," J. Pharma. Sci., 83 (2): 178-185.
Rabea et al., 2003, "Chitosan as antimicrobial agent: applications and mode of action," BioMacromolecules, American Chemical Society 4(6):1457-1465.
Reid, K. et al., 1996, "Multiple Roles for Endothelin in Melanocyte Development: Regulation of Progenitor Number and Stimulation of Differentiation," Development, 122:3911-3919.
Response and Amendment dated Jul. 10, 2015 filed in U.S. Appl. No. 14/210,054.
Rosiak, J. et al., 1992, "Radiation Sterilization of Chitosan Sealant for Vascular Prostheses," J. Radioan. and Nucl. Chem., 159(1):87-96.
Roux, S. et al., 1997, "Ro 61-1790, a New Hydrosoluble Endothelin Antagonist: General Pharmacology and Effects on Experimental Cerebral Vasospasm," J. Pharm. Exp. Ther., 283(3):1110-1118.
Sangui Biotech Witten, 2004, "New Wounds Pads Based on Chitosan and Chitosan-Glucan-Complex," SanguiBioTech GmbH, pp. 1-5.
Scherer et al., 2009, "Poly-N-Acetyl glucosamine nanofibers," Annals of Surgery 250(2):322-330.
Schorigin, P. and Hait, E., 1934, "Über die Nitrierung von Chitin," Chem. Ber., 67:1712-1714.
Schweiger, R.G., 1972, "Polysaccharide Sulfates I. Cellulose Sulfate with a High Degree of Substitution," Carbohydrate Res., 21:219-228.
Shichiri, M. et al., 1991, "Endothelin-1 is an Autocrine/Paracrine Growth Factor for Human Cancer Cell Lines," J. Clin. Invest., 87:1867-1871.
Shirley et al., 2012, "Ehlers-Danlos Syndrome in Orthopaedics," Sports Health, 4(5):394-403.
Staros, J.V. et al., 1986, "Enhancement by N-hydroxysulfosuccinate of Water Soluble Carbodiimide Mediated Coupling Reactions," Anal. Biochem., 156:220-222.
Steen et al., 2001, "Improvement in Skin Thickening in Systemic Sclerosis Associated with Improved Survival," Arthritis & Rheumatism, 44(12):2828-35.
Supplementary European Search Report for European Application No. 11769676.5-1453, dated Sep. 25, 2013.
Supplementary European Search Report for European Application No. 12771138, dated Oct. 1, 2014.
Suzuki, N. et al., 1989, "Production of Endothelin-1 and Big-Endothelin-1 by Tumor Cells with Epithelial-Like Morphology," J. Biochem., 106:736-741.
Tanaka, Y. et al., 1997, "Effects of Chitin and Chitosan Particles on BALB/c Mice by Oral and Parenteral Administration," Biomaterials, 18(8):591-595.
Technical Insights, Inc., 1989, "Barriers to Commercialization," Ch. 4 in *Chitin and Chitosan: Specialty Biopolymers for Foods, Medicine, and Industry*, Technical Insights, Inc., Ft. Lee, NJ.
Thanoo, B.C. et al., 1992, "Cross-linked Chitosan Microspheres: Preparation and Evaluation as a Matrix for the Controlled Release of Pharmaceuticals," J. Pharm. Pharmacol., 44:283-286.
Tokura, S. et al., 1983, "Studies on Chitin VIII. Some properties of Water Soluble Chitin Derivatives," Polym. J., 15:485-489.
TSI Mason Laboratories, 1995, "Efficacy Study of a Test Article in Preventing Peritoneal Adhesion in Sprague-Dawley Rats," Final Report Amendment Supplement to the Final Report, Study No. 2-T35.
US Pharmacopeia XXII, 1990, pp. 1415-1497.
US Pharmacopeia XXII, 1990, pp. 1497-1500.
US Pharmacopeia XXII, 1991, Suppl. 5, pp. 2702-2703.
US Pharmacopeia XXVIII, 2004, "The Biocompatibility of Materials Used in Drug Containers," General Information, pp. 2529-2536.
Vahouny, G.V., 1983, "Comparative Effects of Chitosan and Cholestyramine on Lymphatic Absorption of Lipids in the Rat," Am. J. Clin. Nutr., 38(2):278-284.
Vandevord, P.J. et al., 2003, "The Long-term Immune Response to Chitosan Scaffolds," Society for Biomaterials $29^{th}$ Annual Meeting Transactions, p. 165.
Vasconcelos et al., 2013, "Macrophage polarization following chitosan implantation. Biomaterials," 34(38):9952-9959.
Veleirinho et al., 2014, "Foreign body reaction associated with PET and PET/chitosan electrospun nanofibrous abdominal meshes," PLoS One. 9(4):e95293.
Vournakis, J.N. et al., 1994, "Isolation & Characterization of Pure Poly-N-acetylglucosamine: Controlled Enzymatic Deacetylation and Formulation for Tissue Engineering Applications," J Cell Biochem. Suppl. O(18C): 283 (Abstract PZ 313), Keystone Symposium on Tissue Engineering.
Vournakis, J.N. et al., 2008, "Poly-N-acetyl glucosamine nanofibers regulate endothelial cell movement and angiogenesis: dependency on integrin activation of Ets1," J Vasc Res. 45(3):222-32.
Waknine, Y., 2005, "International Approvals: Taxus Express(2), Nexstent, Chitoskin," http://www.medscape.com/viewarticle/503573.
Webb, M.L. and Meek, T.D., 1997, "Inhibitors of Endothelin," Medicinal Res. Rev., 17:17-67.
Weiner, M.L., 1992, "An Overview of the Regulatory Status and of the Safety of Chitin and Chitosan as Food and Pharmarceutical Ingredients," in *Advances in Chitin and Chitosan*, Brine, C.J. et al., eds., Elsevier Publishers, Ltd., pp. 663-670.
Wollina, U. et al., 2003, "Functional Textiles in Prevention of Chronic Wounds, Wound Healing and Tissue Engineering," *Textiles and the Skin. Curr. Probl. Dermatol.*, Elsner et al., eds., Basel, Karger, 31:82-97.
Written Opinion for International App. No. PCT/US2011/032709 (published as WO 2011/130646), dated Aug. 15, 2011.
Written Opinion for International App. No. PCT/US2012/033782 (published as WO 2012/142581), dated Aug. 20, 2012.
Written Opinion for International App. No. PCT/US2014/025623 (published as WO 2014/165302), dated Jul. 10, 2014.
Written Opinion of the International Searching Authority for International App. No. PCT/US2008/002172 (published as WO 2008/103345), dated Aug. 7, 2009.
Wu et al., 2005, "High efficient fabrication of chitosan micropowder by combination of gamma radiation and jet pulverization," Carbohydrate Polymers 60:61-5.
Yamamoto, A. et al., 2003, "Microfabrication of a Biodegradable Polymer by Ion Beam Irradiation for a New Co-Culture System of Cells," Eur. Cells Mater., 6(Suppl. 1): 77.
Yamashita, J. et al., 1991, "A Large Amount of Endothelin-1 is Present in Human Breast Cancer Tissues," Res. Comm. Chem. Pathol. Pharmacol., 74:363-369.
Yanagisawa, M. et al., 1988, "A Novel Potent Vasoconstrictor Peptide Produced by Vascular Endothelial Cells," Nature, 332:411-415.
Yang, F. et al., 2002, "Performance Modification of Chitosan Membranes Induced by Gamma Irradiation," J. Biomater. Appl., 16:215-226.
Yasin et al., 2004, "Theta defensins protect cells from infection by herpes simplex virus by inhibiting viral adhesion and entry," J Virol. 78(10):5147-56.
Yeo, Y. et al., 2006, "Peritoneal Application of Chitosan and UV-cross-linkable Chitosan," J. Biomed. Mater. Res., 78A:668-675.
Yohn, J.J. et al., 1994, "Human Melanoma Cells Express Functional Endothelin-1 Receptors," Biochem. Biophys. Res. Comm., 201:449-457.
Yoksan, R. et al., 2004, "γ-Ray Irradiation Practical Conditions for Low Molecular Weight Chitosan Material Production," Mat. Res. Soc. Symp. Proc., 792:R5.10.1-R5.10.6.

(56) References Cited

OTHER PUBLICATIONS

Yoshioka, T. et al., 1990, "Encapsulation of Mammalian Cell with Chitosan-CMC Capsule," Biotechnol. Bioeng., 35:66-72.
Zheng et al., 2003, "Study on antimicrobial activity of chitosan with different molecular weights," Carbohydrate Polymers 54:527-530.
Ziche, M. et al., 1995, "$ET_B$ Receptors Promote Proliferation and Migration of Endothelial Cells," J. Cardiovasc. Pharmacol., 26 (Suppl. 3):S284-S286.
Zielinski, B.A. and Aebischer, P., 1994, "Chitosan as a Matrix for Mammalian Cell Encapsulation," Biomaterials, 15(13):1049-1056.
Klokkevold et al., 1999, "The Effect of Chitosan (poly-N-Acetyl Glucosamine) on Lingual Hemostasis in Heparanized Rabbits," J Oral Maxillofac Surg 57:49-52.
Azuma, 2014, "Preparation and Biomedical Applications of Chitin and Chitosan Nanofibers," J. Biomed. Nanotechnol., 10(10): 2891.
Azuma, 2015, "Anti-inflammatory effects of orally administered glucosamine oligomer in an experimental model of inflammatory bowel disease," Carbohydrate Polymers, 115:448.
Azuma, 2015, "Anticancer and Anti-Inflammatory Properties of Chitin and Chitosan Oligosaccharides," J. Funct. Biomater., 6:33-49.
Barouch et al., 2003, "Viral escape from dominant Simian Immunodeficiency Virus epitope-specific cytotoxic T lymphocytes in DNA-vaccinated rhesus monkeys," J Virol. 77(13):7367-75.
Chen et al., 2004, "Transfection of mEpo gene to intestinal epithelium in vivo mediated by oral delivery of chitosan-DNA nanoparticles", World J. Gastroenterol. 10(1): 112-116.
Cho et al., Biomaterials, 1999, "Water-soluble chitin as a wound healing accelerator", Biomaterials, 20(22): 2139-2145.
Cole et al., 1997, "Characterization of a sustained-release delivery system for combined cytokine/peptide vaccination using a poly-N-acetyl glucosamine-based polymer mix", Clin. Cancer Res., 3(6): 867-873.
Fischer et al., 2008, "Non-classical processes in surface hemostasis: mechanisms for the poly-N-acetyl glucosamine-induced alteration of red blood cell morphology and surface prothrombogenicity", Biomed Mater., 3(1):015009.
Forrest and Pack, 2002, "On the kinetics of polyplex endocytic trafficking: implications for gene delivery vector design," Mol Ther. 6(1):57-66.
Fulco et al., 2015, "Poly-N-glucosamine nanofibers for negative-pressure wound therapies", Wound Repair Regen., 23 (2):197-202.
Gorapalli et al., 2012, "Evaluation of a novel poly N-acetyl glucosamine (pGlcNAc) hydrogel for treatment of the degenerating intervertebral disc", Life Sci., 91(25-26):1328-1335.
Hama et al., 2006, "Quantitative comparison of intracellular trafficking and nuclear transcription between adenoviral and lipoplex systems," Mol Ther. 13(4):786-94.
Harmenberg et al., 2010, "Prevention of ulcerative lesions by episodic treatment of recurrent herpes labialis: a literature review", Act. Derm. Venereol 90:122-130.
Harrington et al., 2002, "Recombinant vaccinia virus-induced T-cell immunity: quantitation of the response to the virus vector and the foreign epitope," J Virol. 76(7):3329-37.
Jayakumar et al., 2011, "Biomaterials based on chitin and chitosan in wound dressing applications", Biotechnol. Adv., 29:322-337.
Jean et al., 2009, "Chitosan-plasmid nanoparticle formulations for IM and SC delivery of recombinant GFG-2 and PDGF-BB or generation of antibodies," Gene Therapy, 16: 1097-1110.
Kang et al., 2005, "Arterial embolization using poly-N-acetyl glucosamine gel in a rat kidney model", Anat Rec A Discov Mol Cell Evol Biol, 284(1):454-459.
Kim et al., 2000, "Modulation of Antigen-Specific Humoral Responses in Rhesus Macaques by Using Cytokine cDNAs as DNA Vaccine Adjuvants," J Virol, 74(7): 3427-3429.
Leff, 1998, "DNA motif gooses immune antigenicity response in mice CpG outstrips classic vaccine adjuvant 5-Fold; clinical trial to begin shortly," Bioworld Today 9(214).

Lindner et al., 2015, "pGlcNAc Nanofiber Treatment of Cutaneous Wounds Stimulate Increased Tensile Strength and Reduced Scarring via Activation of Akt1," PLoS One 10(5): e0127876. DOI: 10.1371/journal.pone.0127876.
Mansouri et al., 2004, "Chitosan-DNA nanoparticles as non-viral vectors in gene therapy: strategies to improve transfection efficacy," Eur J Pharm Biopharm. 57(1):1-8.
Muise-Helmericks et al., 2011, "Poly-N-acetyl glucosamine fibers activate bone regeneration in a rabbit femur injury model", J Trauma, 71(2 Suppl 1):S194-6.
Muzyczka, 1992, "Use of adeno-associated virus as a general transduction vector for mammalian cells," Curr. Top Microbiol Immunol. 158:97-129.
Muzzarelli et al., 1999, "Biochemistry, histology and clinical uses of chitins and chitosans in wound healing", Chitin and Chitinases:251-264.
Nagatani et al., 2008, "739 Oral Chitin Administration Ameliorates Chronic Colitis in TCRa Knockout Mice by Upregulating IFN-g Production and Downregulating Chitinase 3-Like-1 Expression in Mucosal Tissues," Gastroenterology 134: A-106.
Nakamura et al, J. Oral. Biosci, 2007, "Nicotine increases expression of beta defensin", vol. 49, Suppl., p. 135, P-105 (English translation provided).
Neurath et al., 2017, "Current and emerging therapeutic targets for IBD", Nature Reviews, vol. 14: 269-278.
Nuss et al., 2017, "Poly-N-Acetyl Glucosamine (sNAG) Enhances Early Rotator Cuff Tendon Healing in a Rat Model", Ann Biom Eng., 45(12):2826-2836.
Pan et al., 2006, Medical Immunology, Zhejiang University Press p. 163.
Premenko-Lanier et al., 2003, "DNA vaccination of infants in the presence of maternal antibody: a measles model in the primate," Virology 307(1):67-75.
Ramírez et al., 2000, "Attenuated modified vaccinia virus Ankara can be used as an immunizing agent under conditions of preexisting immunity to the vector," J Virol. 74(16):7651-5.
Ramírez et al., 2000, "Biology of attenuated modified vaccinia virus Ankara recombinant vector in mice: virus fate and activation of B- and T-cell immune responses in comparison with the Western Reserve strain and advantages as a vaccine," J Virol. 74(2):923-33.
Salem et al., 2004, "Paracrine release of IL-12 stimulates IFN-gamma production and dramatically enhances the antigen-specific T cell response after vaccination with a novel peptide-based cancer vaccine," J Immunol. 172(9):5159-67.
Salem et al., 2006, "Novel nonviral delivery approaches for interleukin-12 protein and gene systems: curbing toxicity and enhancing adjuvant activity," J Interferon Cytokine Res. 26(9):593-608.
Salem et al., 2008, "$T_H1/T_H2$ Cytokine Fingerprinting for Probing Diseases: From the Bench to the Clinic," J. Med. Sci. 1(2):61-67.
Salem et al., 2010, "Using poly-N-acetyl glucosamine gel matrix to deliver IL-12 with anti-schistosomasis vaccination", J. Infect Dev Countries, 4(5):318-328.
Salem et al., 2010, "Poly-N-acetyl glucosamine gel matrix as a non-viral delivery vector for DNA-based vaccination," Anticancer Res. 30(10):3889-3894.
Salem et al., 2014, "Immunomodulatory effects of IL-12 released from poly-N-acetyl glucosamine gel matrix during schistosomiasis infection", Cytotechnology, 66(4):667-675.
Schlee et al., 2008, "Probiotic Lactobacilli and Vsl#3 induce enterocyte beta-defensin 2", Clinical and Experimental Immunology, 151(3): 528-535.
Schorigin, P. and Hait, E. 1934, "Über die Nitrierung von Chitin," Chem. Ber., 67:1712-1714 (English abstract provided).
Spruance et al., 1992, "The Natural History of Recurrent Oral-Facial Herpes Simplex Virus Infection," Seminars in Dermatology 11(3):200-206.
Stoute et al., 1997, "A preliminary evaluation of a recombinant circumsporozoite protein vaccine against *Plasmodium falciparum* malaria. RTS,S Malaria Vaccine Evaluation Group." N Engl J Med.336(2):86-91.

(56) References Cited

OTHER PUBLICATIONS

Tewary et al., 2005, "A heterologous prime-boost vaccination regimen using ORFF DNA and recombinant ORFF protein confers protective immunity against experimental visceral leishmaniasis," J Infect Dis. 191(12):2130-7.
Thatte et al., 2004, "Poly-N-Acetyl Glucosamine-Mediated Red Blood Cell Interactions," J. Trauma 57:S7-S12.
Varmus, 1988, "Retroviruses," Science 240(4858):1427-35.
Vournakis et al., 2004, "Isolation, purification, and characterization of poly-N-acetyl glucosamine use as a hemostatic agent," J Trauma 57(1 Suppl):S2-6.
Wang, 2007, "Transport and Delivery System for Medicament", China Medical Science Press, p. 95.
Wasungu and Hoekstra, 2006, "Cationic lipids, lipoplexes and intracellular delivery of genes," J Control Release 116(2):255-64.
Wasungu et al., 2006, "Lipoplexes formed from sugar-based gemini surfactants undergo a lamellar-to-micellar phase transition at acidic pH. Evidence for a non-inverted membrane-destabilizing hexagonal phase of lipoplexes," Biochim Biophys Acta. 1758(10):1677-84.
Yousef et al., 2012, "Chitosan oligosaccharide as potential therapy of inflammatory bowel disease: Therapeutic efficacy and possible mechanisms of action," Pharmacological Res., 66:66-79.

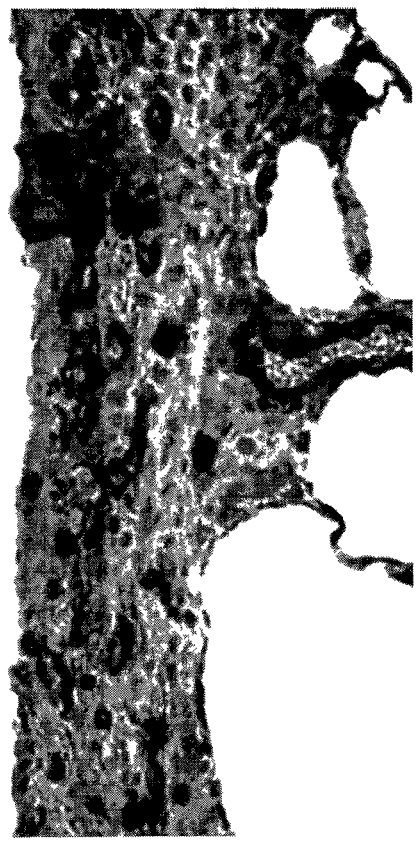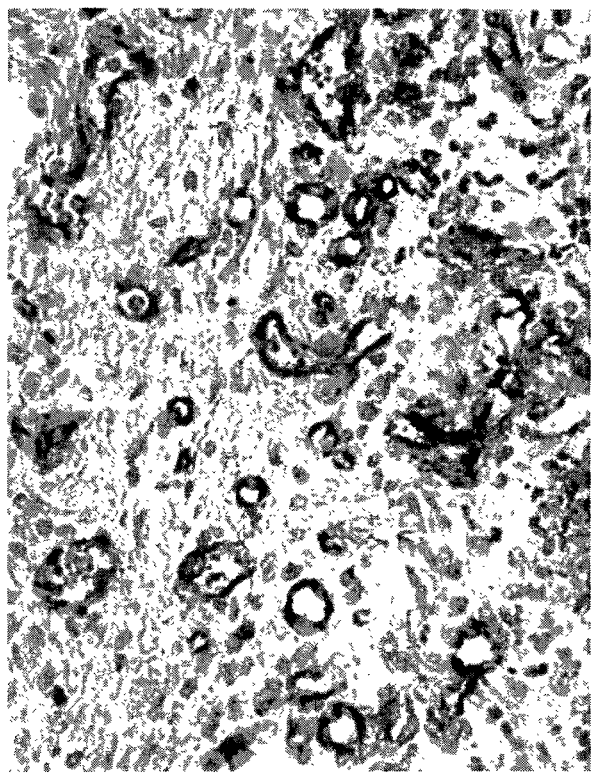
Fig. 19

HEMOSTATIC COMPOSITIONS AND THERAPEUTIC REGIMENS

This application is a divisional of U.S. patent application Ser. No. 13/956,012, filed on Jul. 31, 2013, now U.S. Pat. No. 9,139,663, which is a divisional of U.S. patent application Ser. No. 12/033,670, filed on Feb. 19, 2008, now U.S. Pat. No. 8,871,247, which claims the benefit of U.S. Provisional Application No. 60/901,826, filed on Feb. 19, 2007; each of the foregoing applications is incorporated by reference in its entirety.

1. FIELD

The application relates generally to the field of hemostasis, including methods, compositions, and devices that can be employed to achieve hemostasis at an increased rate or in a reduced period of time. More specifically, the application describes hemostatic compositions that can be applied to wounds and therapeutic regimens for wound treatment. The hemostatic compositions can comprise one or more biocompatible polymers or fibers, such as poly $\beta$-1→4-N-acetylglucosamine dressings. Optionally, the poly $\beta$-1→4-N-acetylglucosamine dressings comprise irradiated poly $\beta$-1→4-N-acetylglucosamine of reduced molecular weight and length.

2. BACKGROUND

Wound healing, or wound repair, is the body's natural process of regenerating dermal and epidermal tissue. After a wound occurs, a set of complex biochemical events takes place in a closely orchestrated cascade to repair the damage. These events overlap in time and may be artificially categorized into separate steps: the inflammatory, proliferative, and maturation and remodeling phases. In the inflammatory phase, bacteria and debris are phagocytized and removed, and factors are released that cause the migration and division of cells involved in the proliferative phase. The proliferative phase is characterized by angiogenesis (formation of new blood vessels from endothelial cells), fibroplasia, collagen deposition, granulation tissue formation, epithelialization, and wound contraction. In the maturation and remodeling phase, collagen is remodeled and realigned along tension lines and cells that are no longer needed are removed by apoptosis.

There are two types of wounds, open and closed. Open wounds are classified according to the object that caused the wound. For example, incisions or incised wounds (including surgical wounds) are caused by a clean, sharp-edged object such as a knife, a razor or a glass splinter. Lacerations are irregular wounds caused by a blunt impact to soft tissue which lies over hard tissue (e.g., laceration of the skin covering the skull) or tearing of skin and other tissues such as caused by childbirth. Abrasions or grazes are superficial wounds in which the topmost layer of the skin (the epidermis) is scraped off. Puncture wounds are caused by an object puncturing the skin, such as a nail or needle. Penetration wounds are caused by an object such as a knife entering the body. Gunshot wounds are caused by a bullet or similar projectile driving into (e.g., entry wound) and/or through the body (e.g., exit wound). In a medical context, all stab wounds and gunshot wounds are considered major wounds. Open wounds also include burn wounds induced by thermal, chemical, or electrical injury.

Closed wounds include contusions (more commonly known as a bruise, caused by blunt force trauma that damages tissue under the skin), hematoma (also called a blood tumor, caused by damage to a blood vessel that in turn causes blood to collect under the skin), and crushing injuries (caused by a great or extreme amount of force applied over a long period of time).

Chronic wounds are wounds that have failed to proceed through an orderly and timely series of events to produce a durable structural, functional, and cosmetic closure. Many chronic wounds are cutaneous wounds or ulcers, caused by factors such as diabetes, venous stasis, arterial insufficiency, or pressure. Certain cutaneous wounds are burn wounds, induced by thermal, chemical, or electrical injury. Chronic wounds are the source of significant pain and suffering. If left without treatment they can cause life threatening complications, reduce the rate of recovery or worsen other health conditions. Intensive and effective treatment can help restore skin integrity, and avoid unwanted health problems. While these wounds are inflicted by different causes, the wound healing process and the wound treatment strategies are similar in many respects.

Bed sore are one type of pressure ulcers which may significantly reduce the quality of life and negatively affect general prognosis. Bed sores are localized areas of skin injury that develop when soft tissue is compressed between a bony prominence and an hard surface for a long time. Bed sores usually develop from laying or sitting for a prolonged period without changing the body posture. For those who are bed-bound, pressure sores are most likely to form on or around the heels, the hip-bone, and the lower back or tailbone. Pressure ulcers may also develop in a variety of other areas, including the spine, ankles, knees shoulders, and head, depending upon the position of the patient. If left without treatment, bedsores may degenerate to the stage of decay of epithelial tissue, with inflammation, bacterial infection and other serious complications. The body's response to the infection often results in fever, shaking chills, changes in mental status, rapid pulse, and respiratory rate.

Temporary dressings, including interactive temporary dressings, are intended to provide supportive care until definitive closure can be accomplished. Temporary dressings are expected to function as a barrier, much like human skin. Available wound dressings are effective to a degree, but have significant shortcomings, such as high frequency of dressing changes, wound drying or dressing adherence, high treatment costs, development of a foreign body reaction, and a low rate of improvement, especially in elderly patients. The foreign body reaction begins as wound healing, including accumulation of exudate at the site of injury, infiltration of inflammatory cells to debride the area, and the formation of granulation tissue. However, the persistent presence of a foreign body can inhibit full healing. Rather than the resorption and reconstruction that occurs in wound healing, the foreign body reaction is characterized by the formation of foreign body giant cells, encapsulation of the foreign object, and chronic inflammation. Encapsulation refers to the firm, generally avascular collagen shell deposited around a foreign body, effectively isolating it from the host tissues. This response was developed as a protective measure. The foreign body reaction can lead to chronic pain.

Healing time of a chronic wound can range from a few weeks to a year, depending on the size and type of wound. Wound treatment involves many direct and indirect costs. According to the International Committee on Wound Management (ICWM), wound dressings comprise only 10 percent to 15 percent of the total direct treatment cost (International Committee on Wound Management, 1994, Wounds 6(3):94-100). In contrast, a significant percentage of total cost is attributed to care provider salary and staff expenses (International Committee on Wound Management, 1994, Wounds 6(3):94-100).

There is a need in the art for wound dressings that do not induce foreign body reactions or do so at a lower rate than traditional wound dressings. Such wound dressings would need to be changed on a less frequent basis and reduce healing time to closure, and thus may translate into more effective therapy for the patient and a reduced cost of care.

3. SUMMARY

The application is based, in part, on the inventors' discovery of the improved wound healing and reduced need for wound dressing changes when poly-β-1→4-N-acetylglucosamine ("pGlcNAc" or "NAG") is administered to wounds in a diabetic mouse model. These studies indicate that pGlcNAc can be advantageously used as a wound dressing for wounds without the need for frequent wound dressing changes that are required of other wound dressings that are currently in use. Other polymers or fibers with similar characteristics to pGlcNAc may also be used in accordance with the methods described herein.

The improved wound healing characteristics of pGlcNAc together with the reduced need for pGlcNAc wound dressing changes are especially pronounced when the pGlcNAc is irradiated to reduce its molecular weight and length. The inventors have discovered that irradiation reduces the molecular weight and length of pGlcNAc without disturbing the microstructure of the fibers, such that the infrared spectrum of the irradiated pGlcNAc is substantially similar or equivalent to that of the non-irradiated pGlcNAc.

This reduced molecular weight pGlcNAc, referred to herein as "sNAG" (for short N-Acetyl Glucosamine), shows improved activity in promoting wound healing and no detectable foreign body reaction in treated animals. Thus, this polymer or fiber is particularly useful for treatment of wounds at a greater efficacy and reduced cost.

Accordingly, described herein are methods for treating a wound in a patient, preferably a human subject, said method comprising topically applying a dressing to a wound in the patient, thereby treating the wound in the patient. Preferably, the application is repeated every 3 to 35 days (a significant improvement over the methods presently used in the clinic, in which the application is repeated every 2 days). The dressing materials are preferably polymers or fibers, as described in Section 5.2 below. Preferably, the polymers or fibers are irradiated to improve their efficacy, as described in Section 5.3 below. Preferably, the dressing is a dressing of biocompatible and/or immunoneutral poly-β-1→4-N-acetylglucosamine or a derivative thereof, as described in Section 5.2.1 below. Alternative frequencies of wound dressing changes or reapplications are described in Section 5.4 below.

Described herein is a poly-β-1→4-N-acetylglucosamine composition comprising biocompatible poly-β-1→4-N-acetylglucosamine fibers, wherein (i) the majority of the fibers are less than about 15 µm in length, and (ii) the composition (a) increases metabolic rate of serum-starved human umbilical cord vein endothelial cells in a MTT assay and/or does not rescue apoptosis of serum-starved human umbilical cord vein endothelial cells in a trypan blue exclusion test, and (b) is non-reactive when tested in an intramuscular implantation test. In certain embodiments, the composition increases metabolic rate of serum-starved human umbilical cord vein endothelial cells in a MTT assay and does not rescue apoptosis of serum-starved human umbilical cord vein endothelial cells in a trypan blue exclusion test. In one embodiment, the majority of the fibers have a thickness or diameter of about 1-2 µm. In one embodiment, at least 50% of the fibers are about 4 µm in length.

Also described herein is a method for treating a wound in a human subject, comprising: (a) topically applying a dressing to a wound in a human subject in need thereof, wherein the dressing comprises a poly-β-1→4-N-acetylglucosamine composition comprising biocompatible poly-β-1→4-N-acetylglucosamine fibers, thereby treating the wound in said human subject. In certain embodiments, the majority of the fibers are less than about 15 µm in length, and the composition (a) increases metabolic rate of serum-starved human umbilical cord vein endothelial cells in a MTT assay and/or does not rescue apoptosis of serum-starved human umbilical cord vein endothelial cells in a trypan blue exclusion test, and (b) is non-reactive when tested in an intramuscular implantation test. In certain other embodiments, the method further comprises: (b) repeating said application every 5 to 35 days. In one embodiment, the wound is a chronic wound. In one embodiment, the chronic wound is a diabetic ulcer, a venous stasis ulcer, an arterial insufficiency ulcer, or a pressure ulcer. In one embodiment, the chronic wound is a venous stasis ulcer. In another embodiment, the wound is a surgical wound or a burn wound.

In addition, described herein is a method for producing a poly-β-1→4-N-acetylglucosamine composition, said method comprises irradiating biocompatible poly-β-1→4-N-acetylglucosamine fibers, such that (i) the majority of the irradiated fibers are less than about 15 µm in length, and (ii) the composition (a) increases metabolic rate of serum-starved human umbilical cord vein endothelial cells in a MTT assay and/or does not rescue apoptosis of serum-starved human umbilical cord vein endothelial cells in a trypan blue exclusion test, and (b) is non-reactive when tested in an intramuscular implantation test, thereby producing the poly-β-1→4-N-acetylglucosamine composition. In certain embodiments, the poly-β-1→4-N-acetylglucosamine fibers are irradiated as dried fibers. In one embodiment, the poly-β-1→4-N-acetylglucosamine fibers are irradiated by gamma irradiation at 500-2,000 kgy. In certain other embodiments, the poly-β-1→4-N-acetylglucosamine fibers are irradiated as wet fibers. In one embodiment, the poly-β-1→4-N-acetylglucosamine fibers are irradiated by gamma irradiation at 100-500 kgy.

Furthermore, described herein is a method for treating a wound in a human subject, comprising: (a) topically applying a dressing to a wound in a human subject in need thereof, wherein the dressing comprises biocompatible poly-β-1→4-N-acetylglucosamine, and (b) repeating said application every 5 to 35 days, thereby treating the wound in said human subject, wherein the human subject is a diabetic, a smoker, a hemophiliac, an HIV-infected person, an obese person, a person undergoing radiation therapy, or a person with venous stasis ulcer. In certain embodiments, the human subject is a person with venous stasis ulcer. In one embodiment, the wound is a chronic wound. In certain embodiments, the chronic wound is a diabetic ulcer, a venous stasis ulcer, an arterial insufficiency ulcer, or a pressure ulcer. In one embodiment, the chronic wound is a venous stasis ulcer. In other embodiments, the wound is a surgical wound or a burn wound.

Furthermore, described herein is a method for treating a chronic wound in a human subject, comprising: (a) topically applying a dressing to a chronic wound in a human subject in need thereof, wherein the dressing comprises biocompatible poly-β-1→4-N-acetylglucosamine, and (b) repeating said application every 5 to 35 days, thereby treating the chronic wound in said human subject, wherein the chronic wound is a diabetic ulcer, a venous stasis ulcer, an arterial insufficiency ulcer, or a pressure ulcer. In certain embodiments, the chronic wound is a venous stasis ulcer.

In certain embodiments, the dressing of step (a) is removed prior to step (b). In certain other embodiments, the dressing of step (b) is not removed prior to step (b).

In certain embodiments, the poly-β-1→4-N-acetylglucosamine is a microalgal poly-β-1→4-N-acetylglucosamine. In certain embodiments, the poly-β-1→4-N-acetylglucosamine is not a crustacean poly-β-1→4-N-acetylglucosamine.

In certain embodiments, the poly-β-1→4-N-acetylglucosamine comprises fibers, and wherein the poly-β-1→4-N-acetylglucosamine have been irradiated to reduce the length of the fibers.

In certain embodiments, at least 75% of the dressing consists of poly-β-1→4-N-acetylglucosamine.

In certain embodiments, the poly-β-1→4-N-acetylglucosamine comprises deacetylated poly-β-1→4-N-acetylglucosamine. In one embodiment, the deacetylated poly-β-1→4-N-acetylglucosamine is 20-70% deacetylated.

4. BRIEF DESCRIPTION OF THE FIGURES

FIG. 1. Wound closure analysis of pGlcNAc treated and non-treated wounds. Standardized photographs were taken on the day of wounding (day 0) and twice a week during the follow-up. Wound contraction (C), reepithelialization (E), and open wound (O) were studied as a percentage of the original wound area.

Figure 2B:
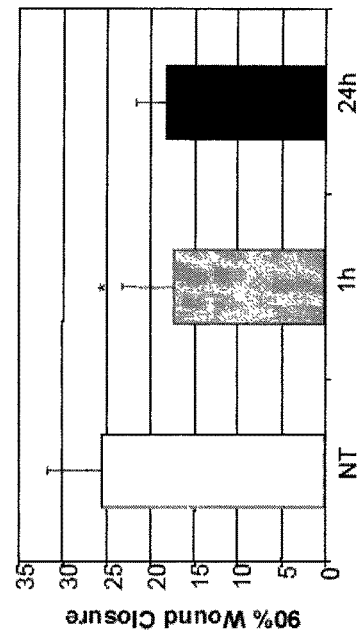
Figure 2C:
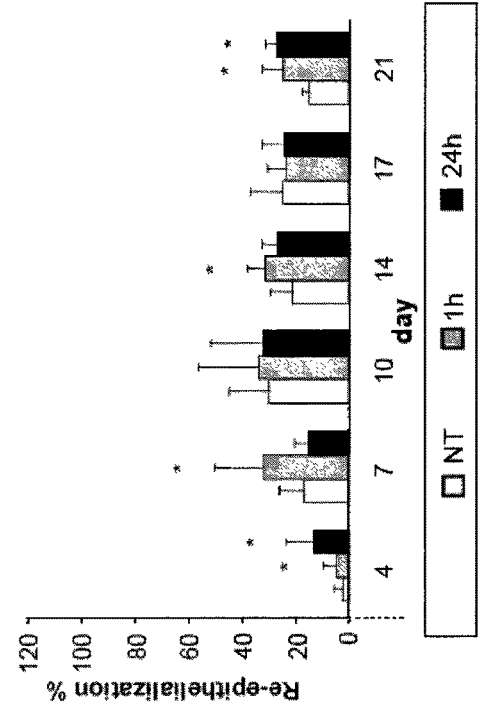
Figure 2A:
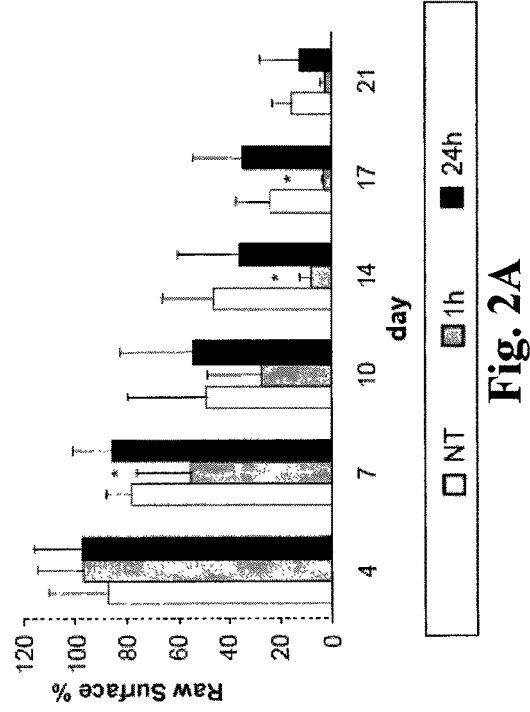
Figure 2D:
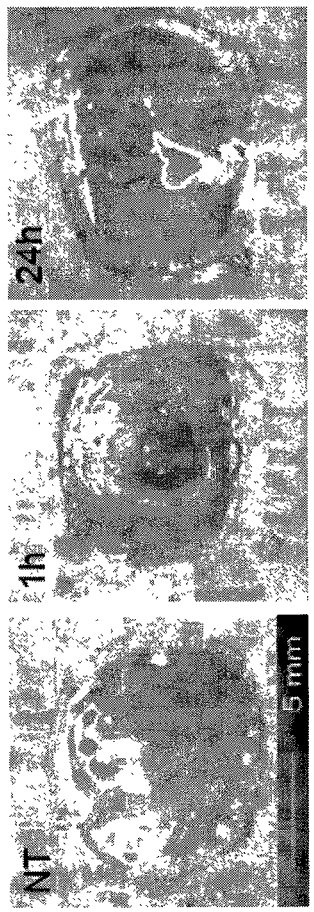
Figure 2E:
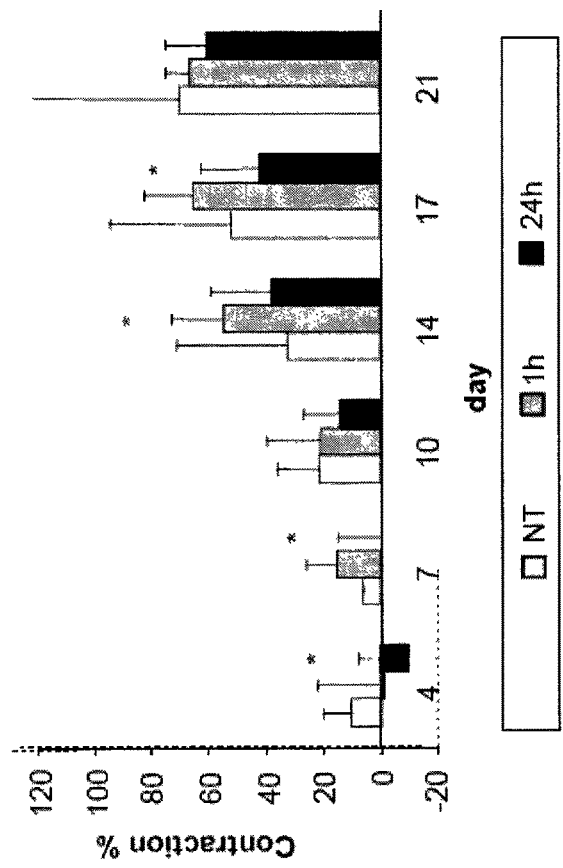

FIGS. 2A-E. pGlcNAc induced faster wound closure. FIG. 2A: The application of the pGlcNAc patch for 1 hour induced faster reduction of raw surface. FIG. 2B: The 1 h group reached 90% wound closure faster than the NT group. FIG. 2C: Reepithelialization was enhanced after 1 h patch application. FIG. 2D: The 1 h group showed enhanced reepithelialization on day 14. FIG. 2E: The application of the patch for 24 h decreased wound contraction when compared to non-treated wounds. Mean values and standard deviations are shown. *$p<0.01$.

Figure 3A:
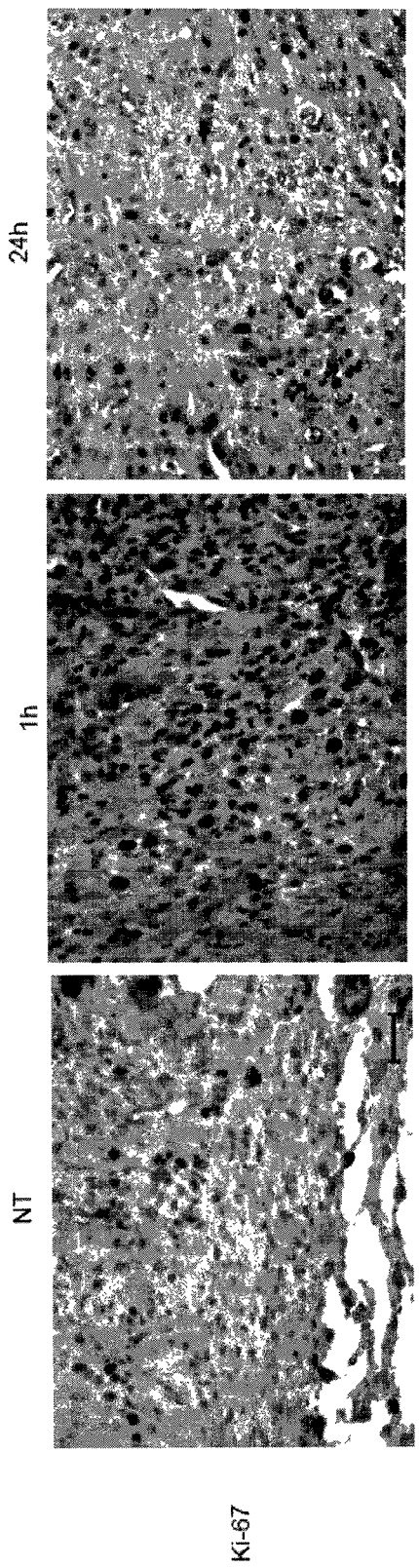
Figure 3B:
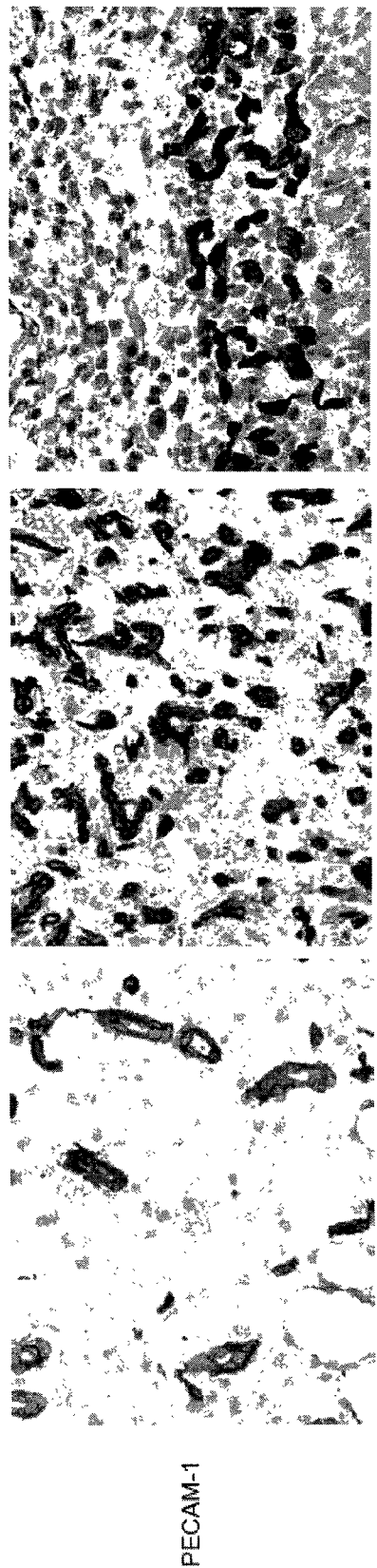
Figure 3C:
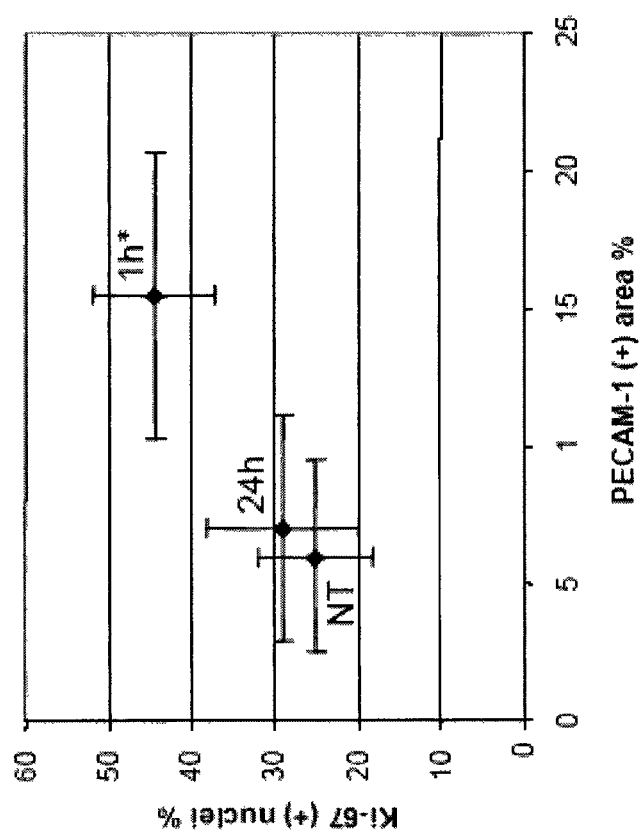

FIGS. 3A-C. The Wound Watch staging system. FIG. 3A: Ki-67 staining: the 1 h group showed enhanced cell proliferation on day 10 compared to the other groups. FIG. 3B: PECAM-1 staining: the 1 h group showed enhanced neo-vascularization on day 10 compared to the other groups. FIG. 3C: The plot combines the quantification of the two immunohistochemical markers, visually showing the difference between groups on study. The 1 h group dramatically differed from both the 24 h and NT groups. Mean values and standard deviations are shown. *$p<0.01$.

Figure 4A:
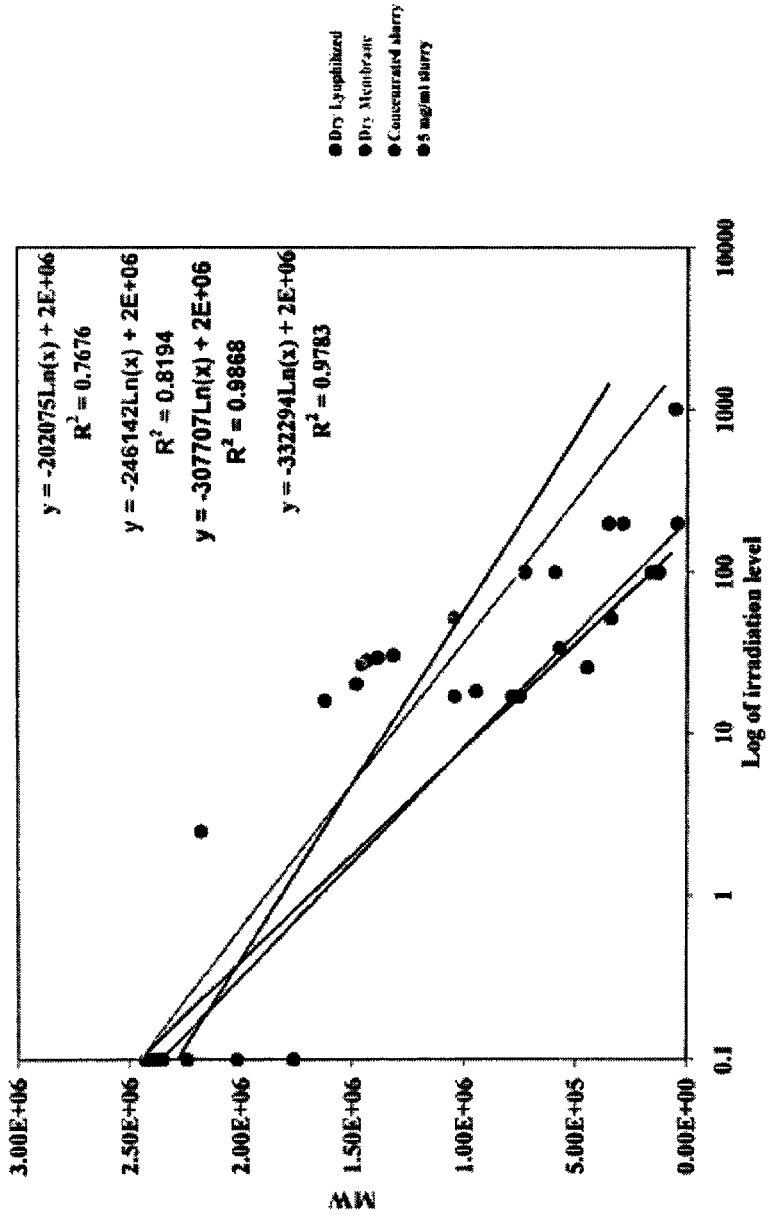
Figure 4B:
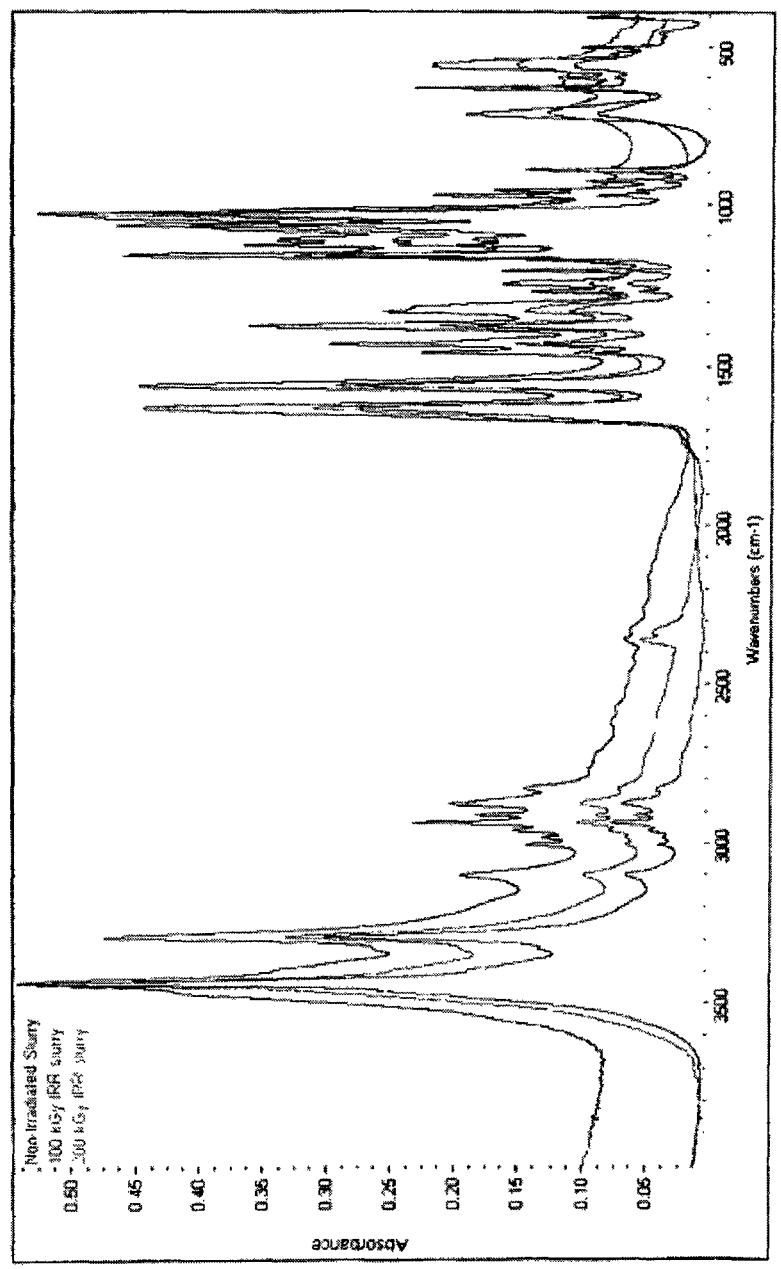
Figure 4C:
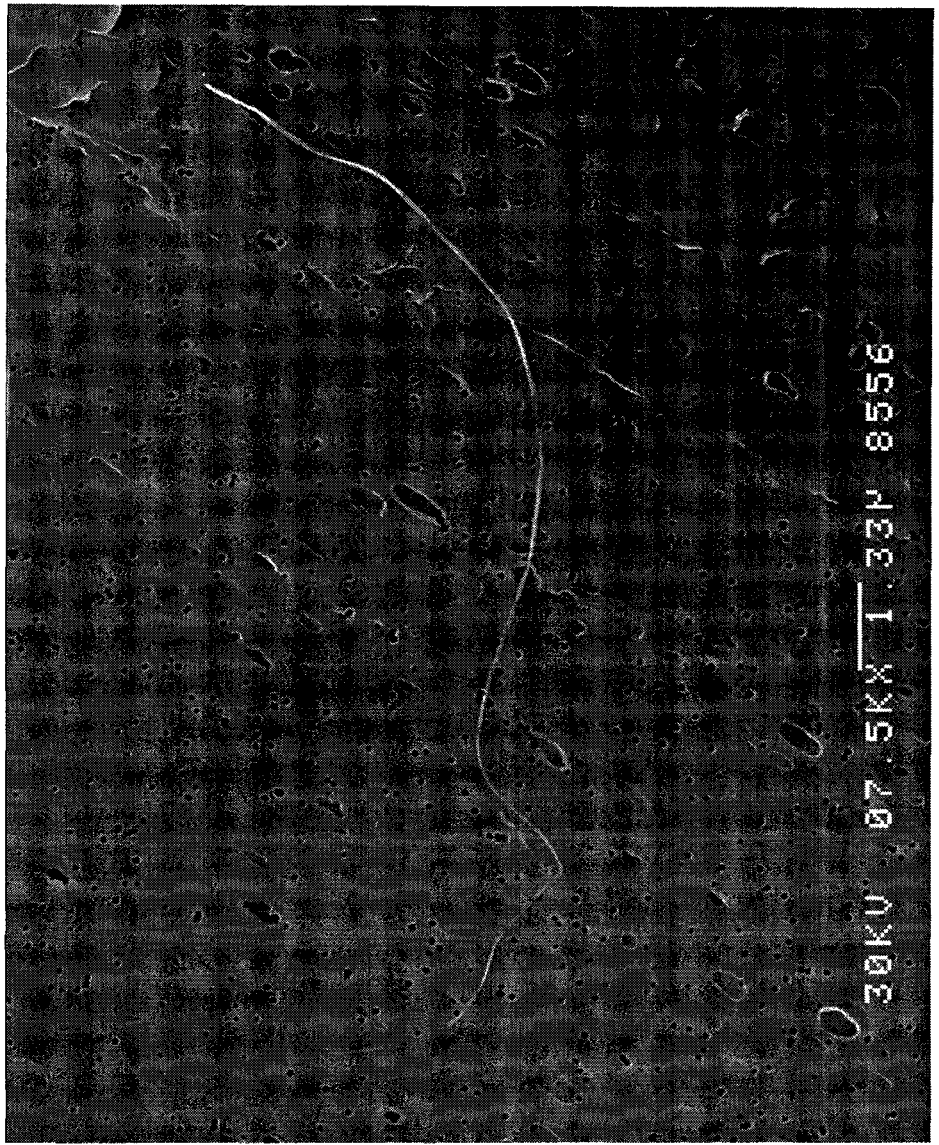
Figure 4D:
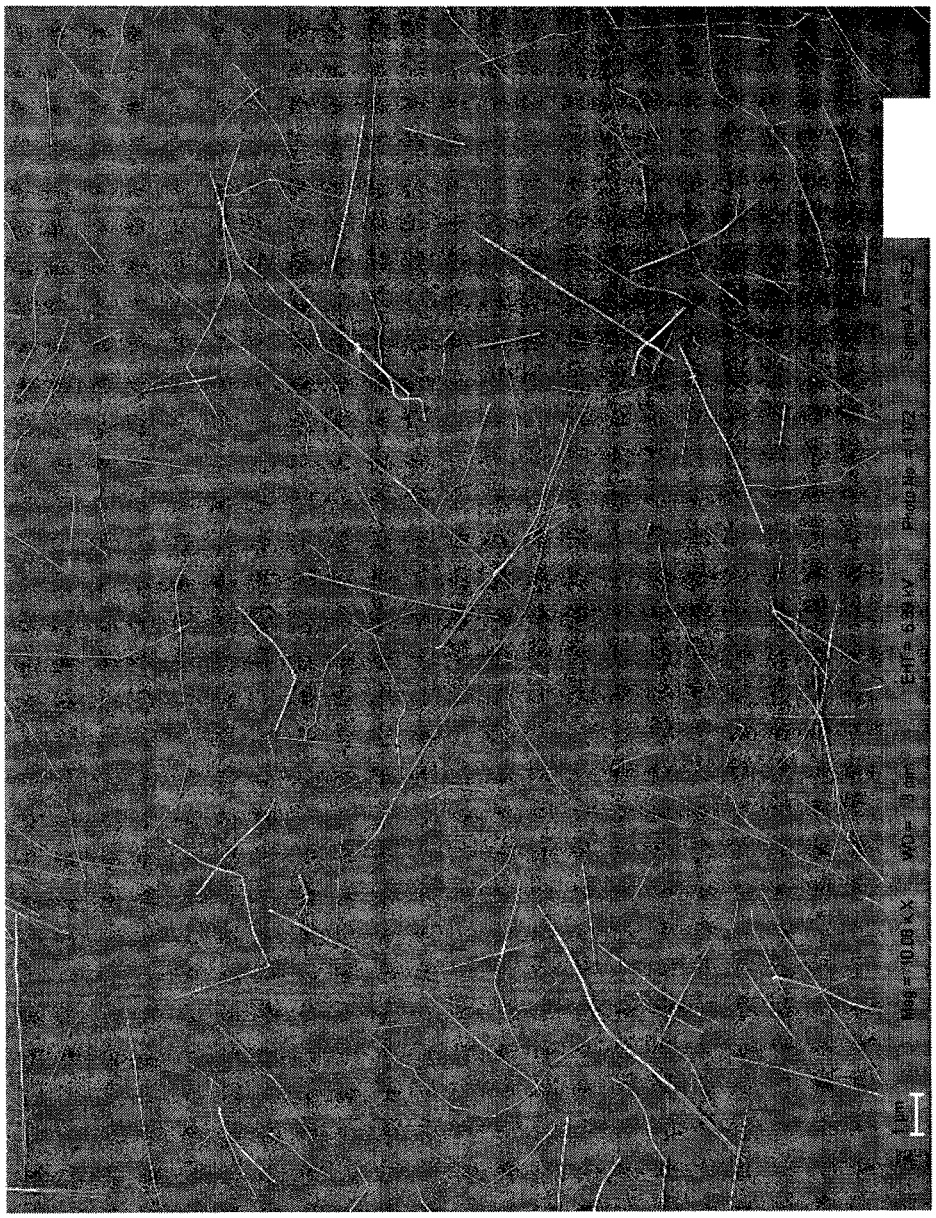

FIGS. 4A-D. Effect of irradiation on chemical and physical structure of pGlcNAc fibers. FIG. 4A: Correlation between molecular weight of pGlcNAc and irradiation level. FIG. 4B: Infrared (IR) spectrum of non-irradiated pGlcNAc slurry (top line), pGlcNAc slurry irradiated at 100 kGy (bottom line), and pGlcNAc slurry irradiated at 200 kGy (middle line). FIG. 4C: Scanning electron microscopic (SEM) analyses of pGlcNAc. FIG. 4D: Scanning electron microscopic (SEM) analyses of sNAG.

Figure 5:
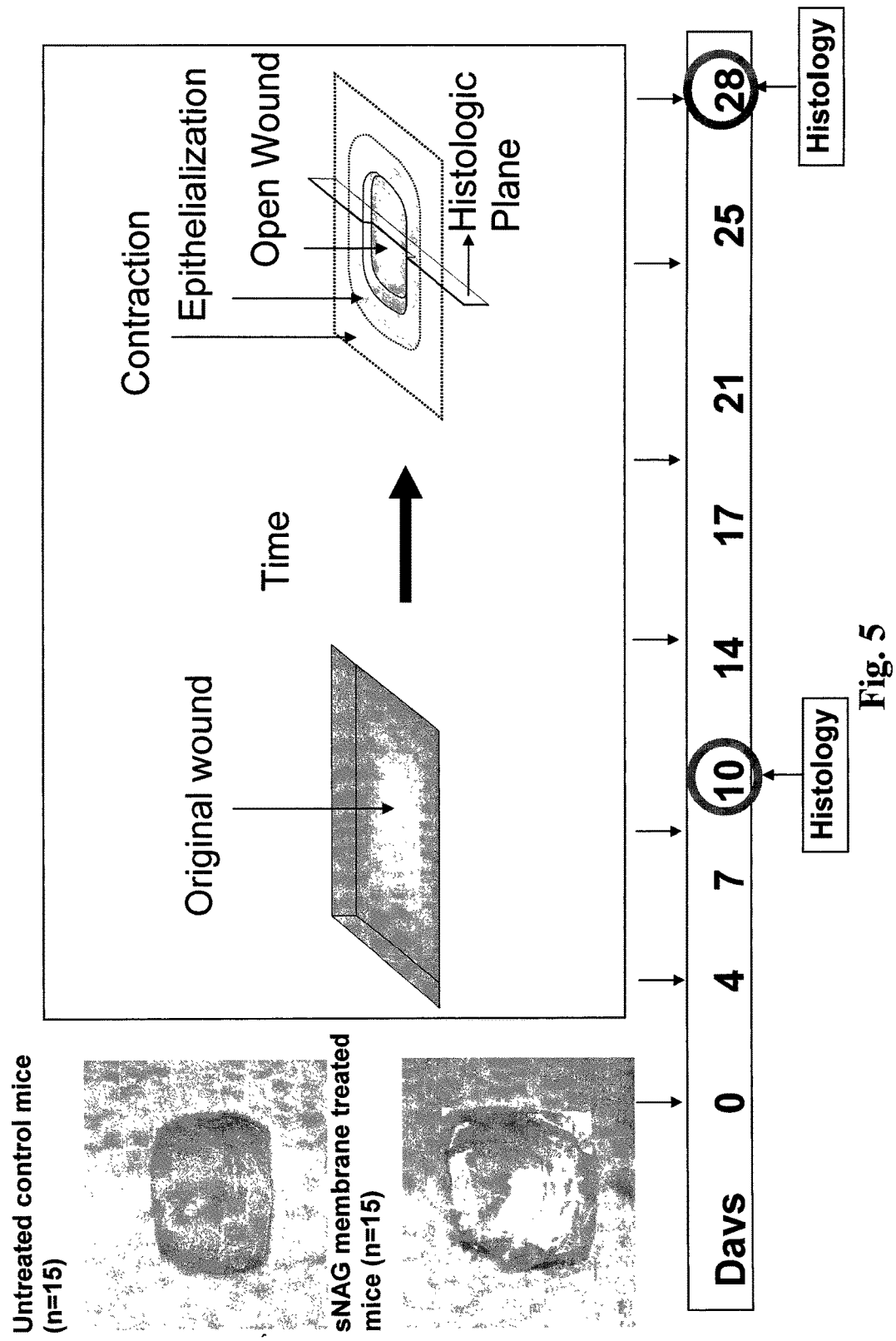
Figure 6:
Figure 7:
Figure 8:
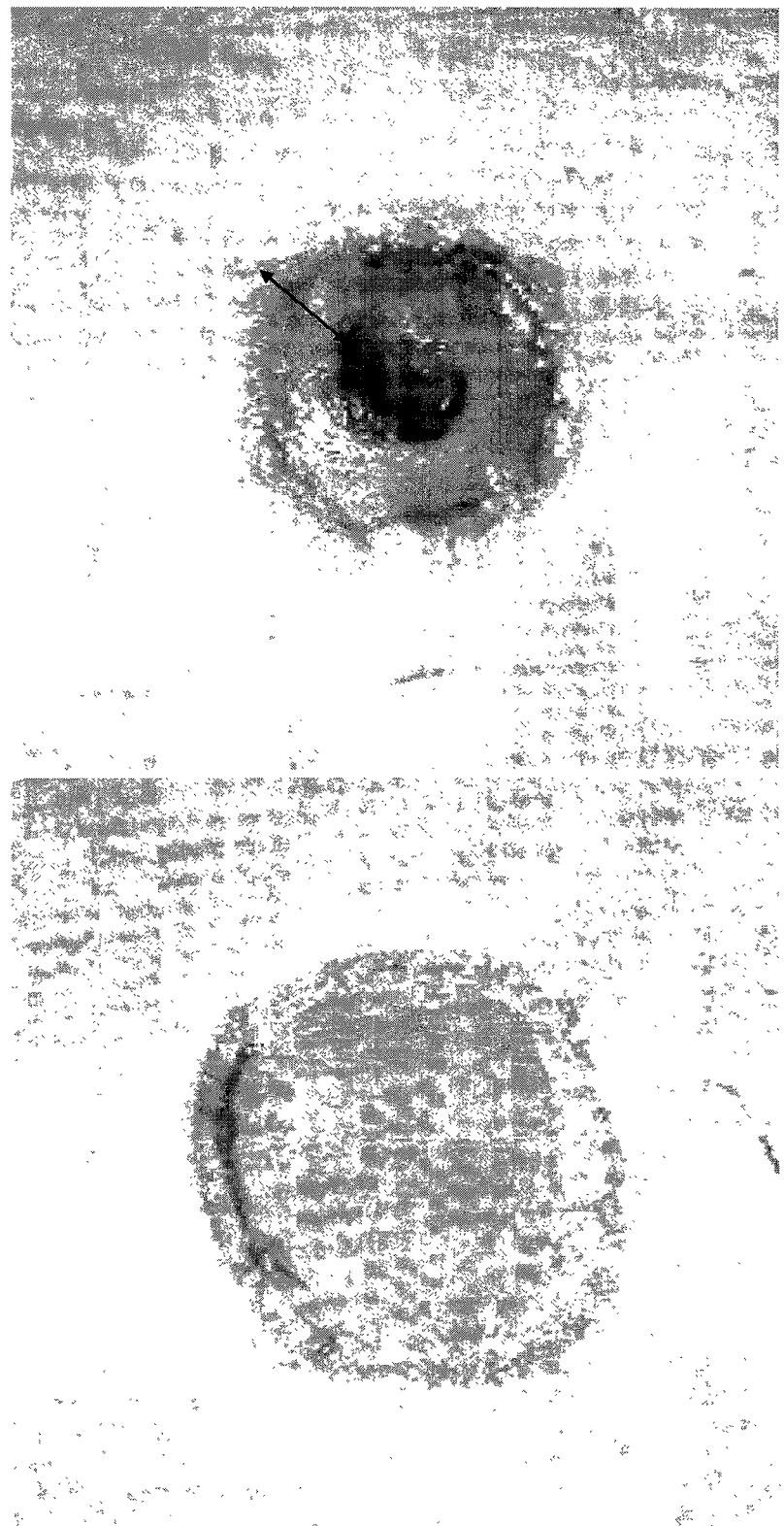
Figure 9:
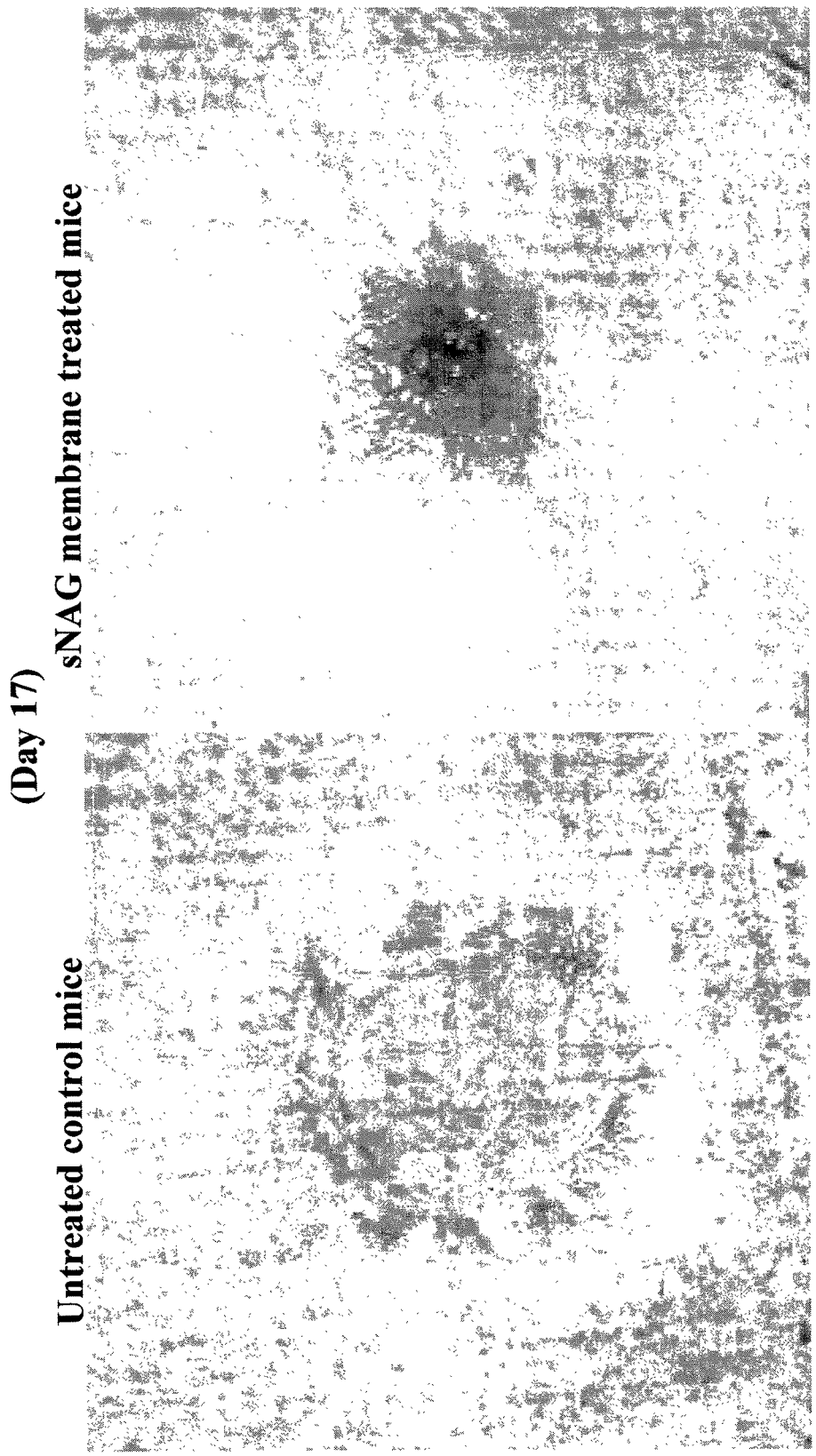

FIG. 5. Wound closure analysis of sNAG (irradiated pGlcNAc, see Sections 5.3 and 6.2.1 below) membrane treated and untreated control wounds. Standardized photographs were taken on day 0, 4, 7, 10, 14, 17, 21, 25, and 28. Wound contraction (C), reepithelialization (E), and open wound (O) were studied as a percentage of the original wound area.

Figure 10:
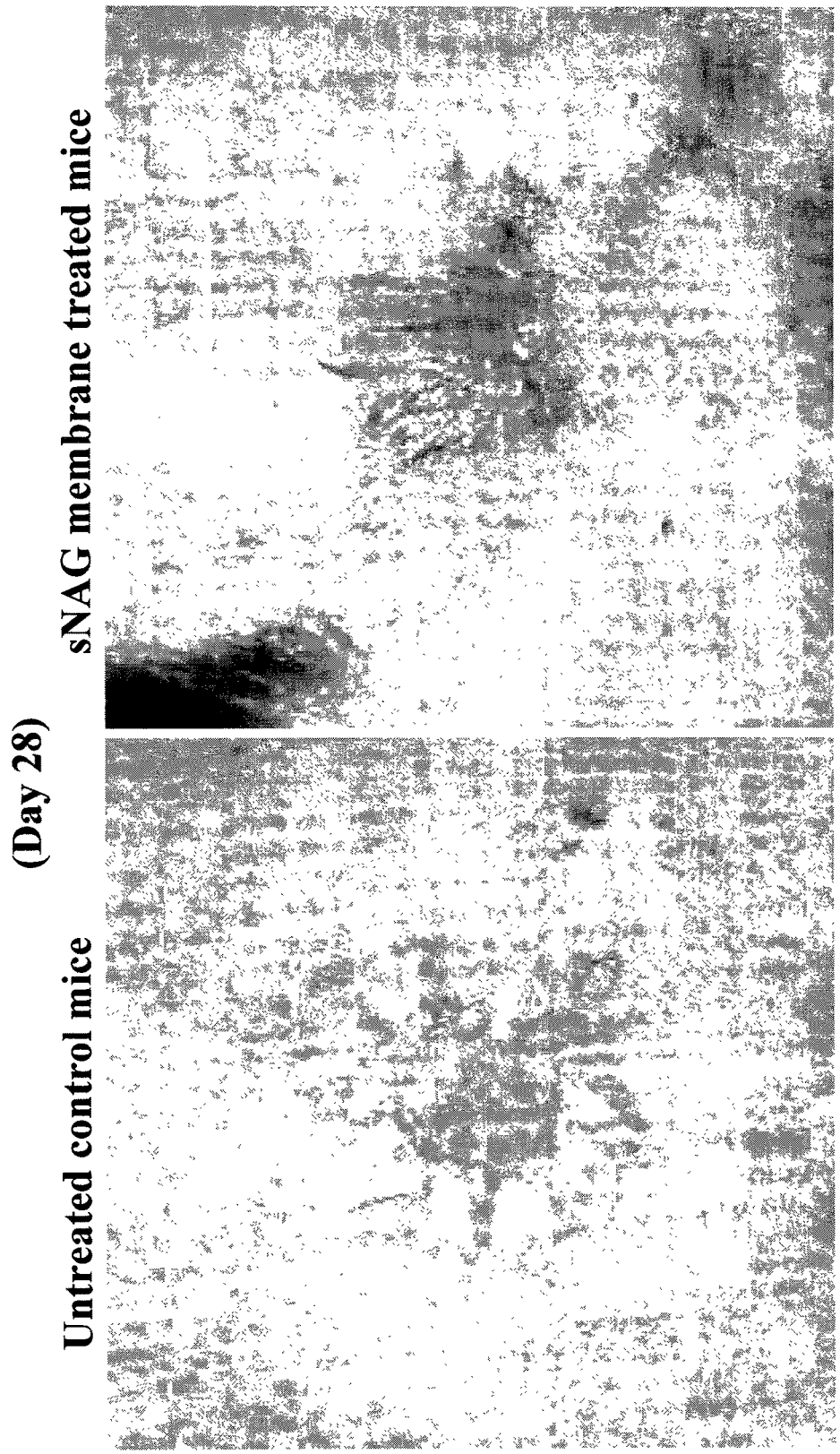

FIGS. 6-10. Macroscopic photograph of a wound of a sNAG membrane treated mice and a wound of an untreated control mice at day 0 (FIG. 6), 4 (FIG. 7), 10 (FIG. 8), 17 (FIG. 9), and 28 (FIG. 10).

Figure 11:
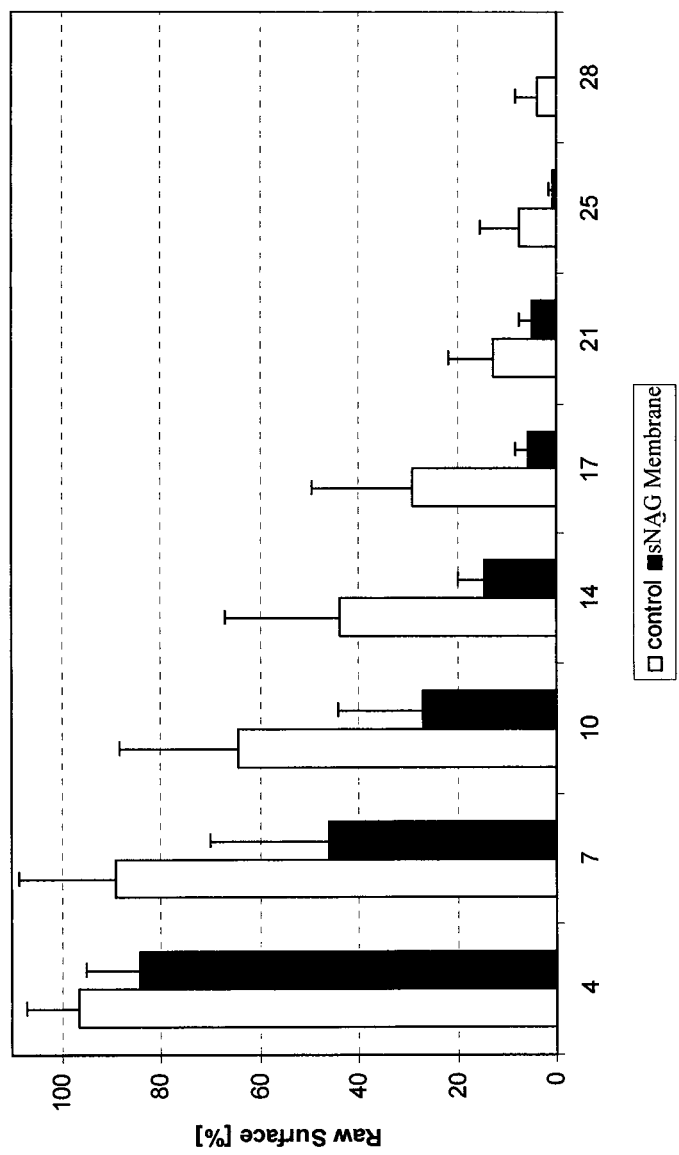
Figure 12:
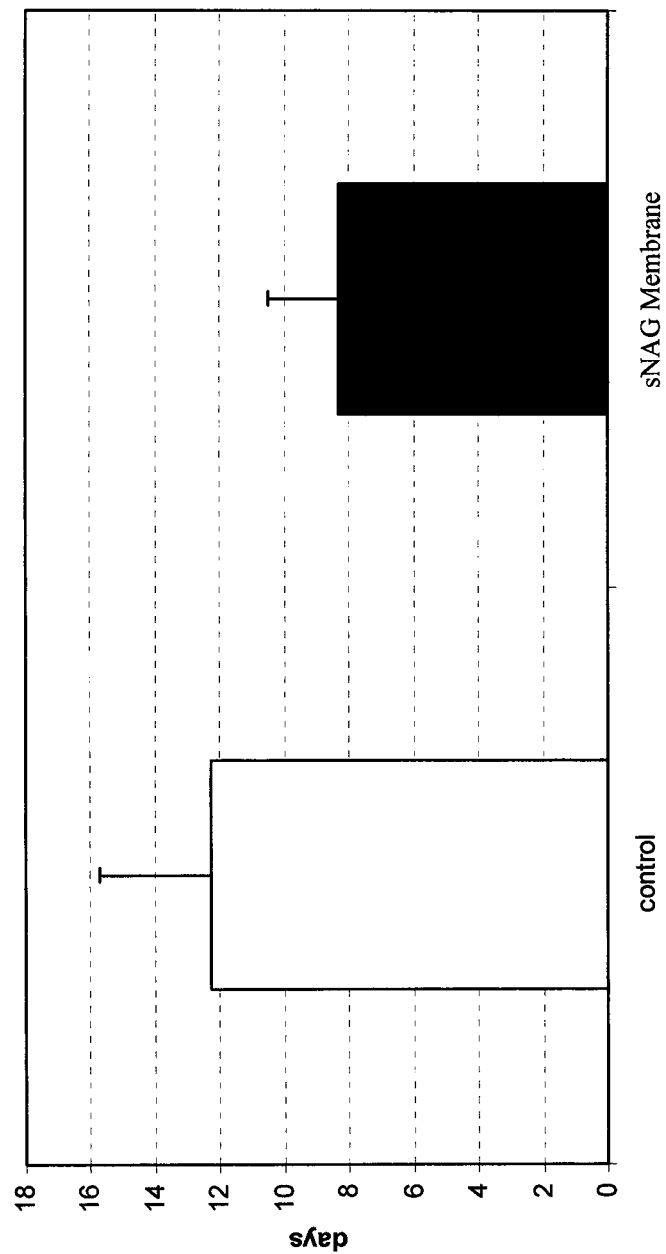
Figure 13:
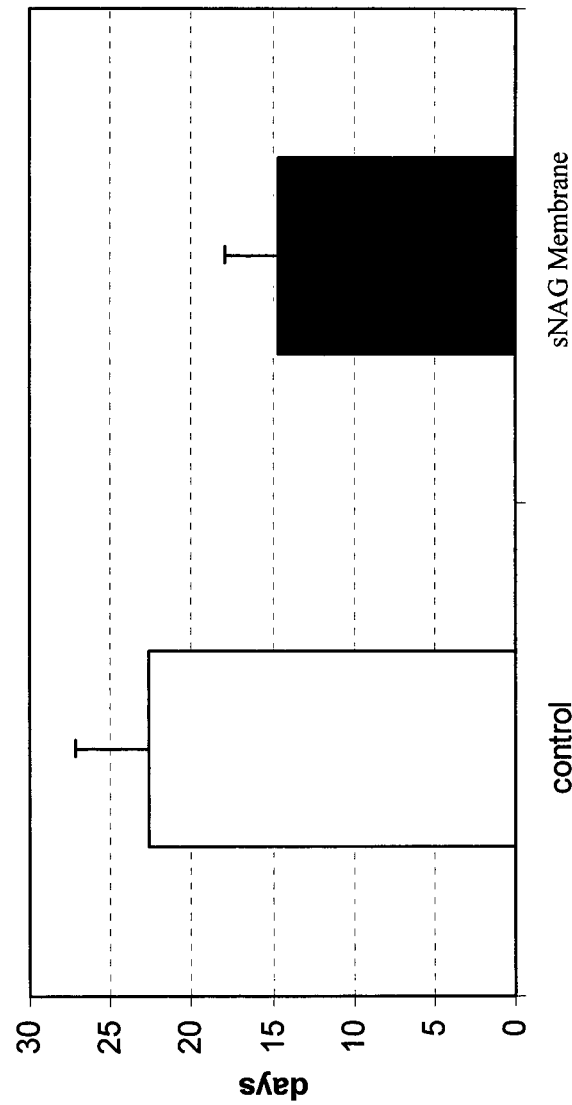
Figure 14:
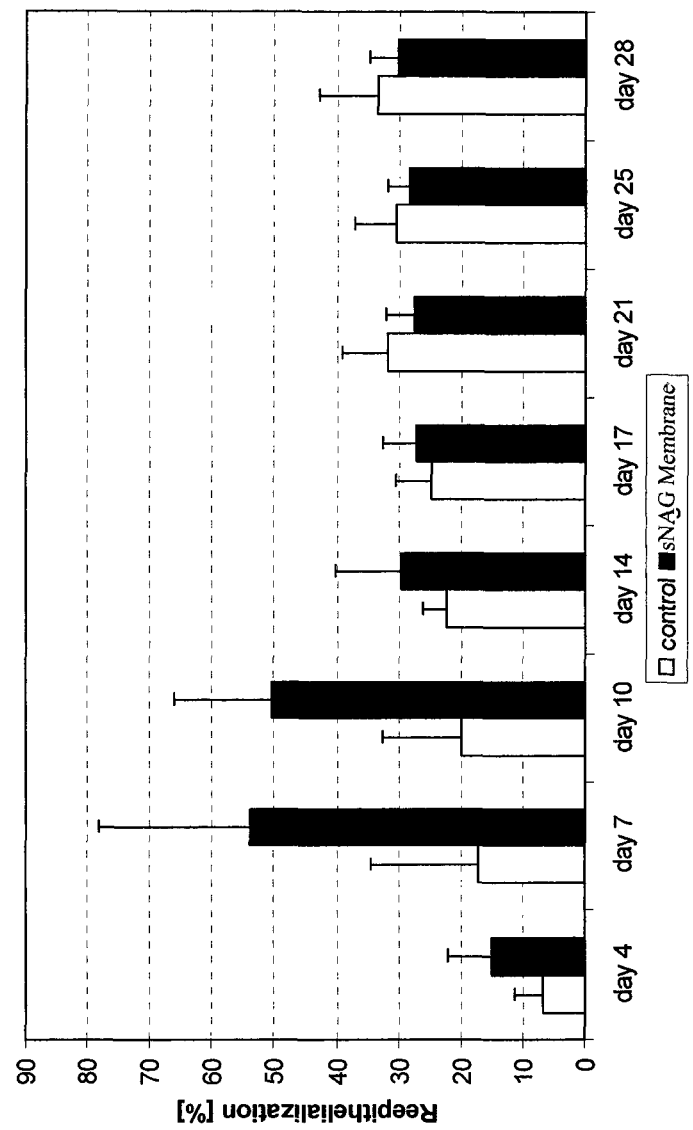
Figure 15:
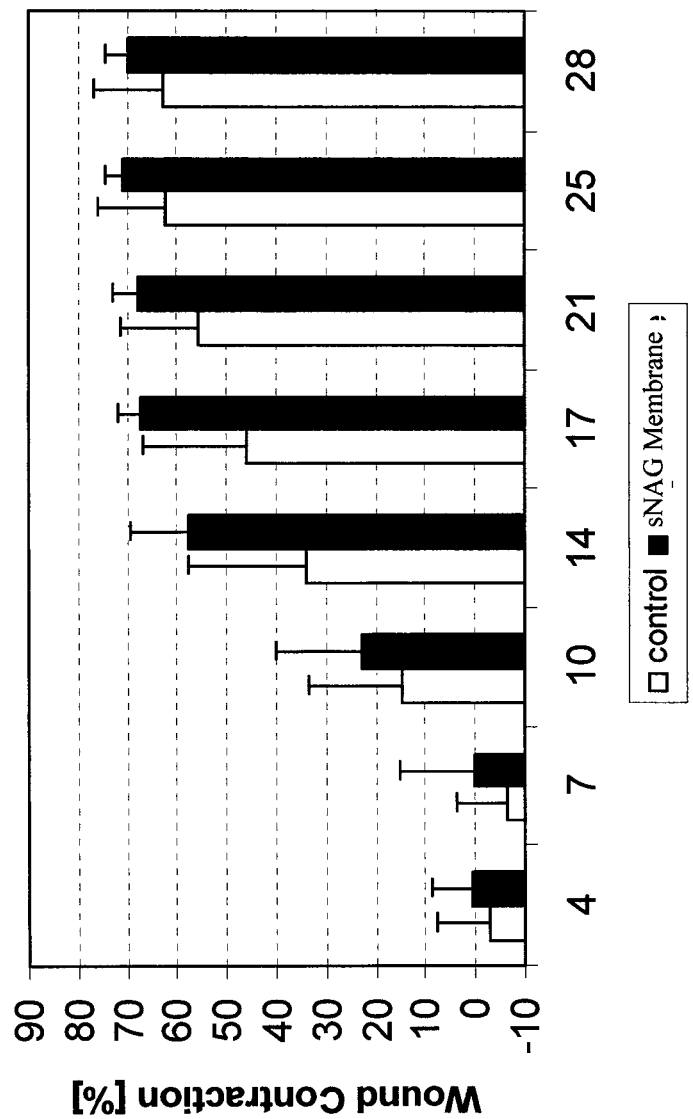

FIGS. 11-15. sNAG induced faster wound closure. The application of the sNAG membrane induced faster reduction of raw surface (FIG. 11). The sNAG membrane treated mice reached 50% (FIG. 12) and 90% (FIG. 13) wound closure faster than the untreated control mice. The sNAG membrane treated mice showed enhanced reepithelialization on day 4, 7 and 10 (FIG. 14). The sNAG membrane treated mice showered greater wound contraction on day 14 and 17 (FIG. 15).

Figure 16:
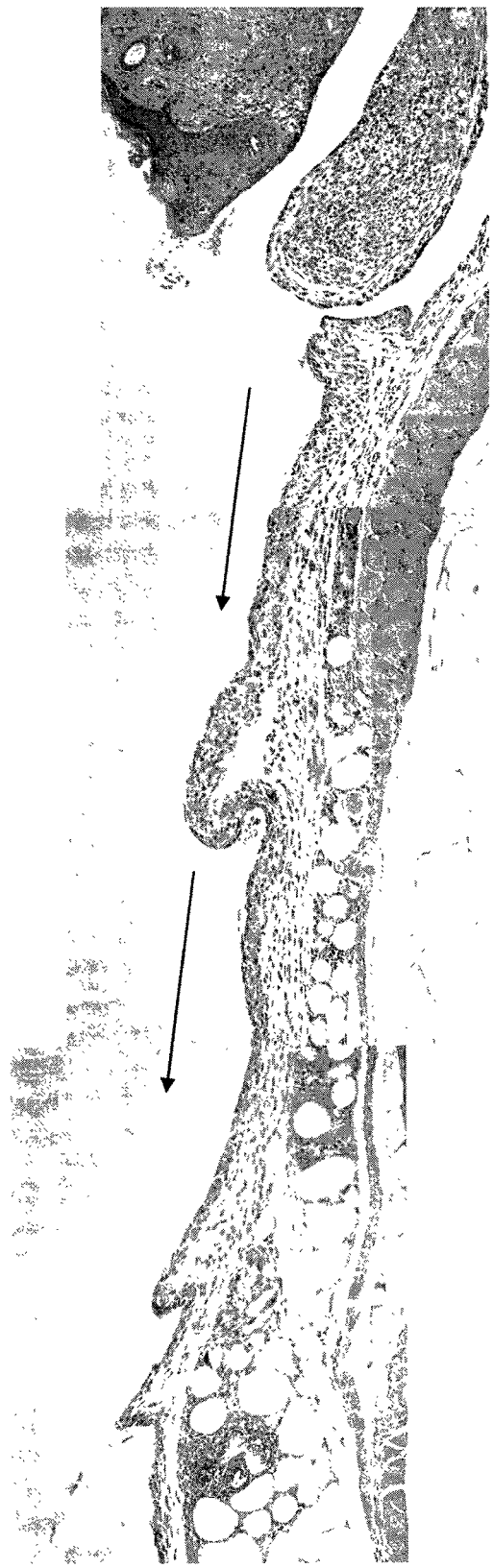
Figure 17:
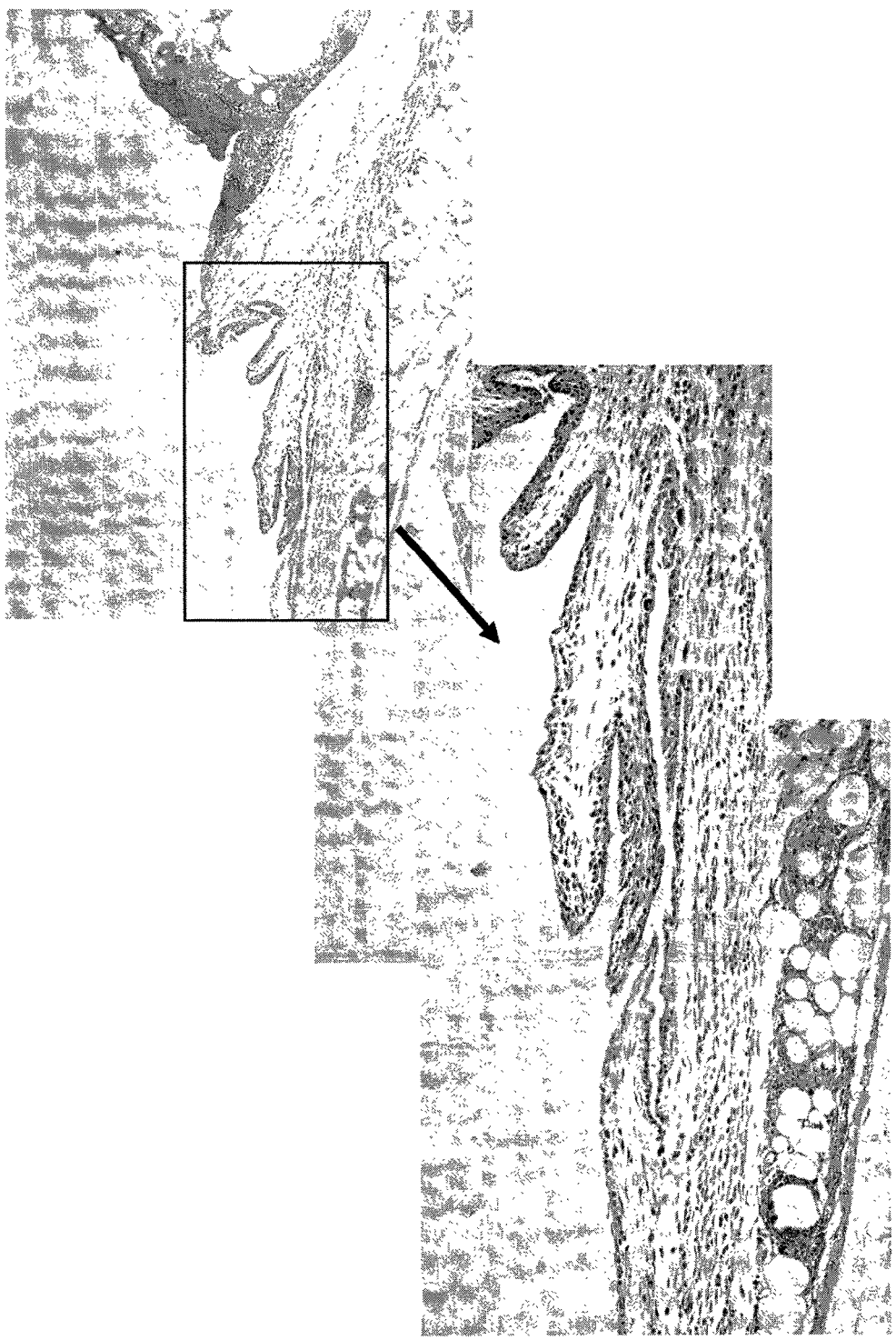

FIGS. 16-17. Histology of the wound edge in a sNAG membrane treated mouse (FIG. 17) and an untreated control mouse (FIG. 16).

Figure 18:
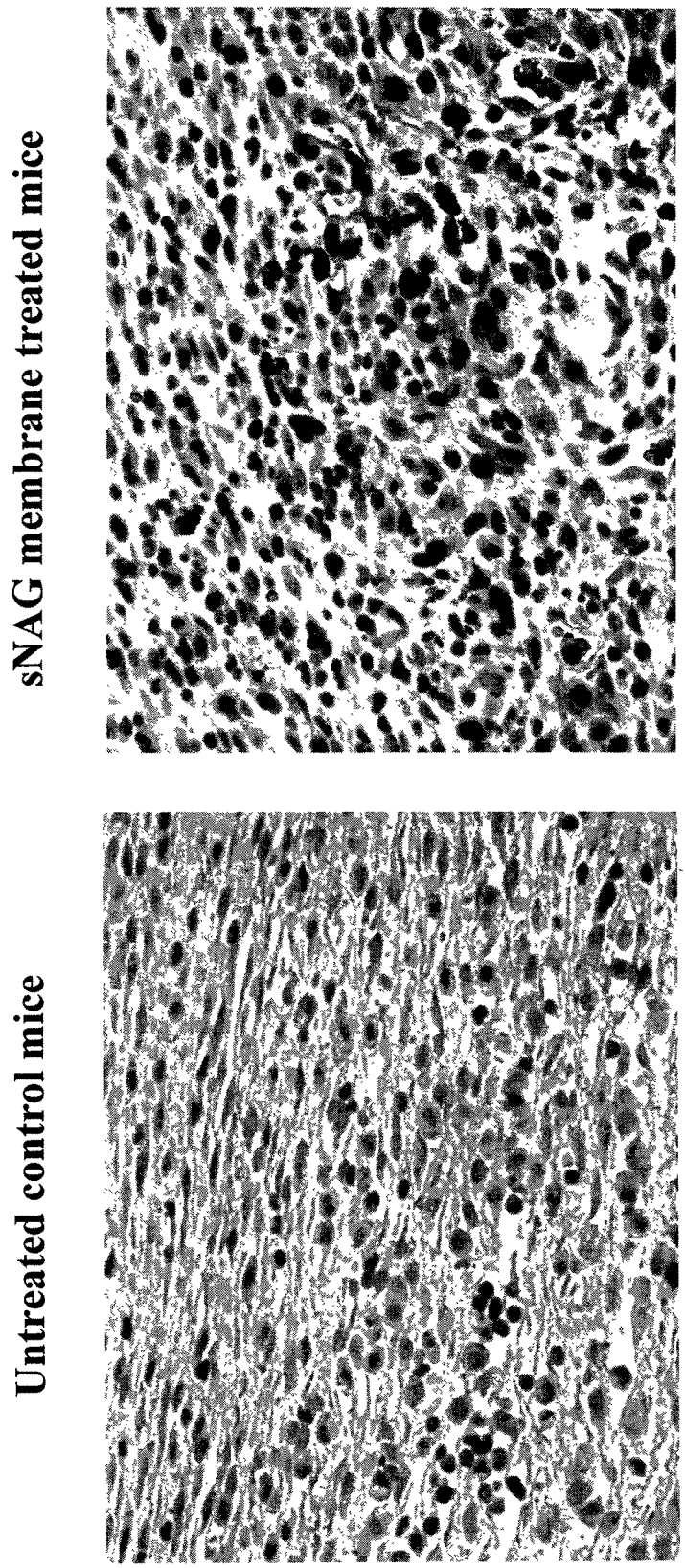

FIG. 18. Ki-67 staining: the sNAG membrane treated mice showed enhanced cell proliferation on day 10 compared to the untreated control mice.

FIG. 19. PECAM-1 staining: the sNAG membrane treated mice showed enhanced neo-vascularization on day 10 compared to the untreated control mice.

Figure 20:
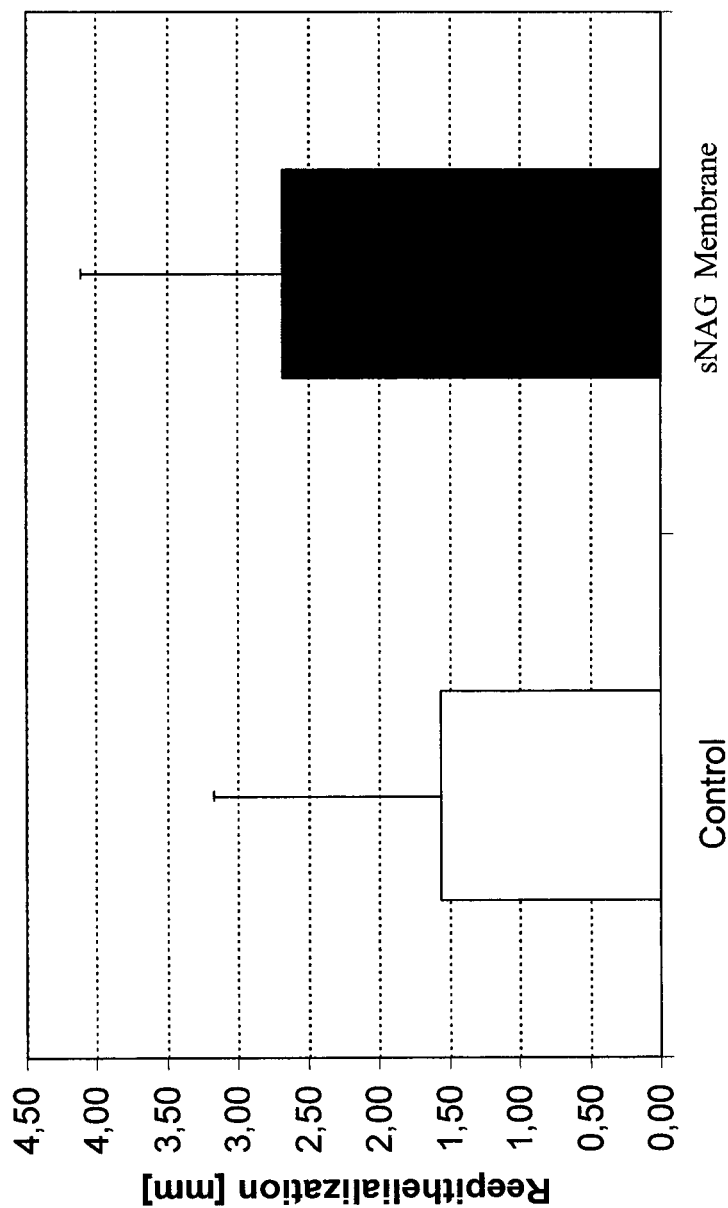

FIG. 20. Degree of wound reepithelialization for sNAG membrane treated mice and untreated control mice measured at day 10.

Figure 21:
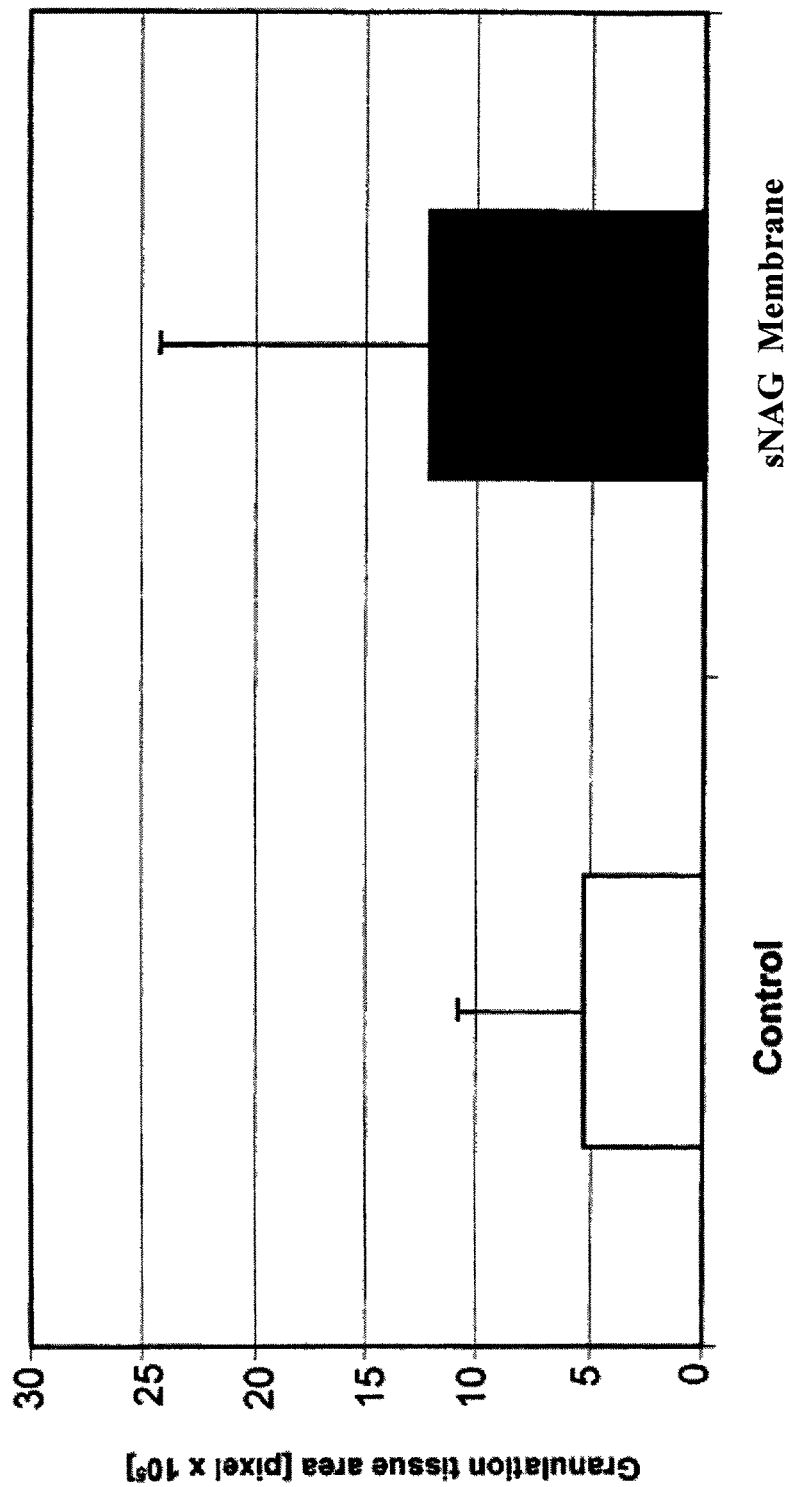

FIG. 21. Degree of granulation tissue formation for sNAG membrane treated mice and untreated control mice measured at day 10.

Figure 22:
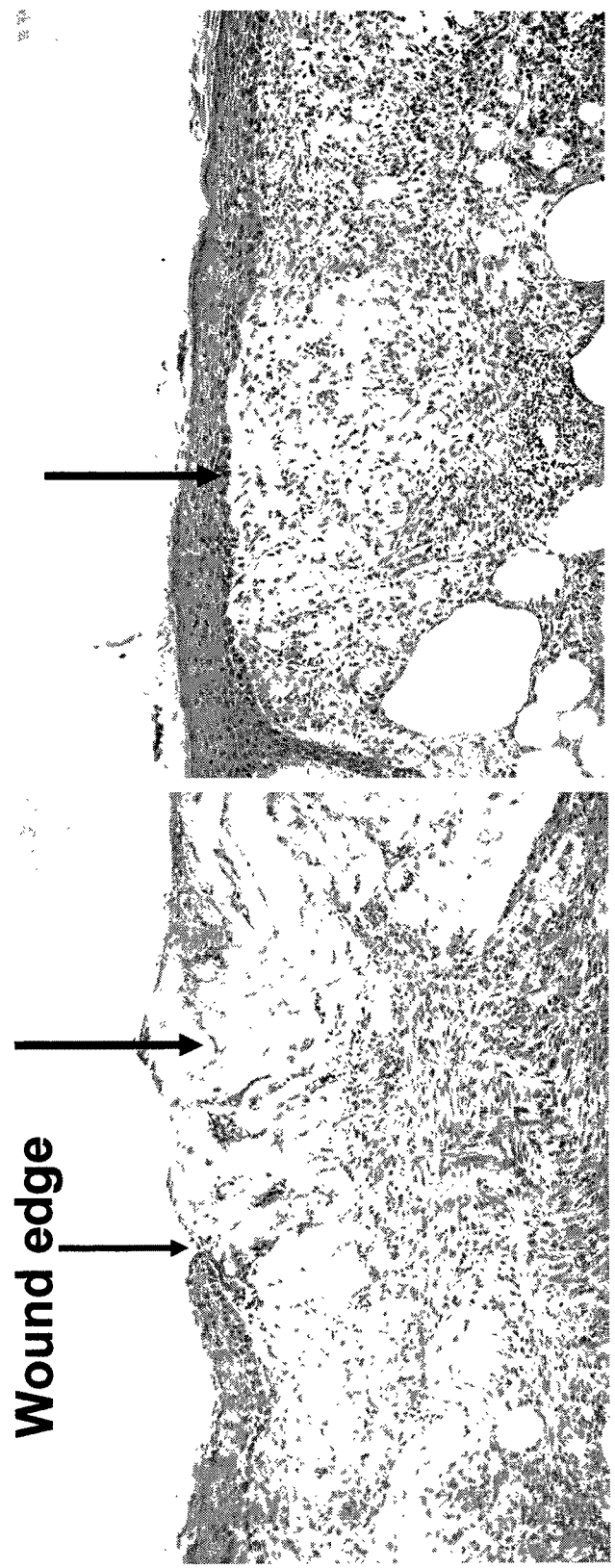

FIG. 22. Histological analysis of untreated control vs. sNAG membrane treated wound at day 10. Note that there is no foreign body reaction in the sNAG membrane treated mice.

Figure 23:

FIG. 23. Collagen staining of untreated control vs. sNAG membrane treated wound at day 10. No foreign body encapsulations can be observed in the sNAG membrane treated mice.

Figure 24:
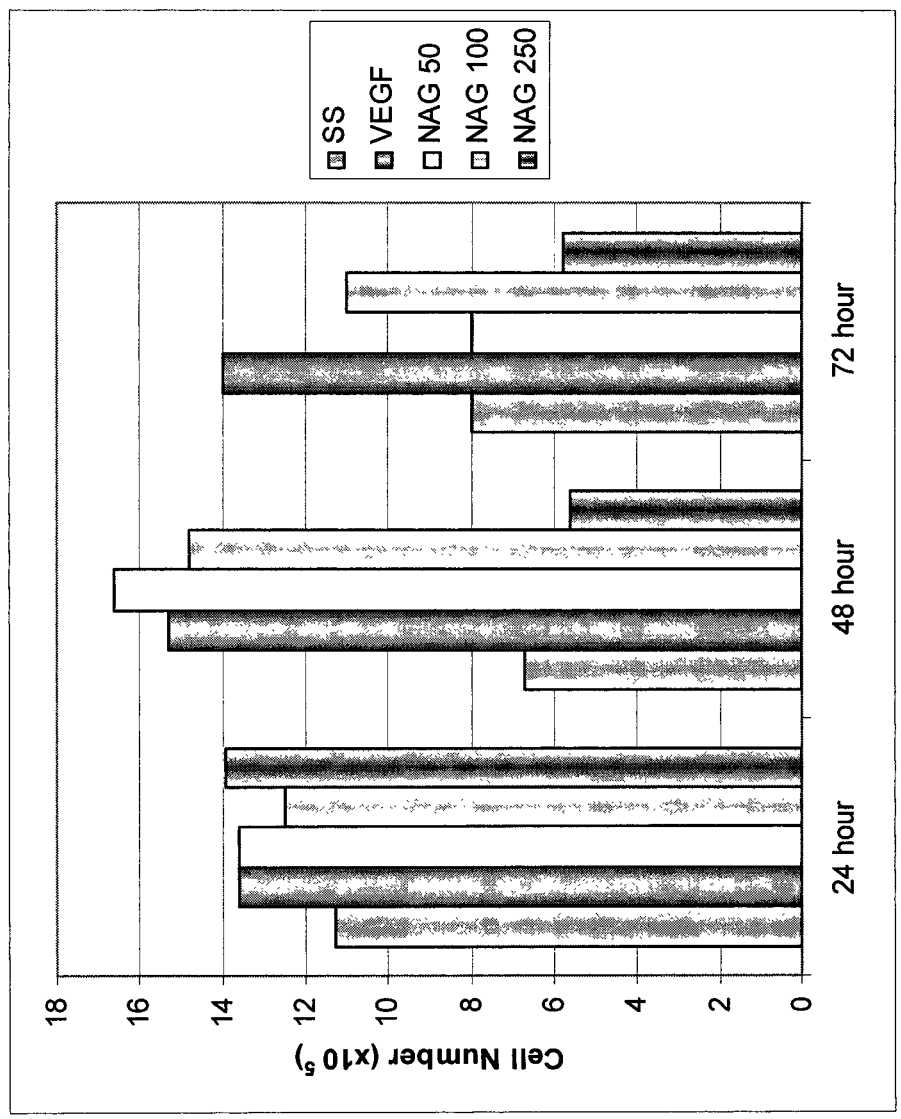

FIG. 24. pGlcNAc protected human umbilical vein endothelial cell (EC) from cell death induced by serum deprivation. For each time period (i.e., at 24, 48 and 72 hours), the identity for each of the five bars (from left to right) is as follows: serum starvation (SS), VEGF, and pGlcNAc (NAG) at 50, 100, and 250 µg/ml.

Figure 25:
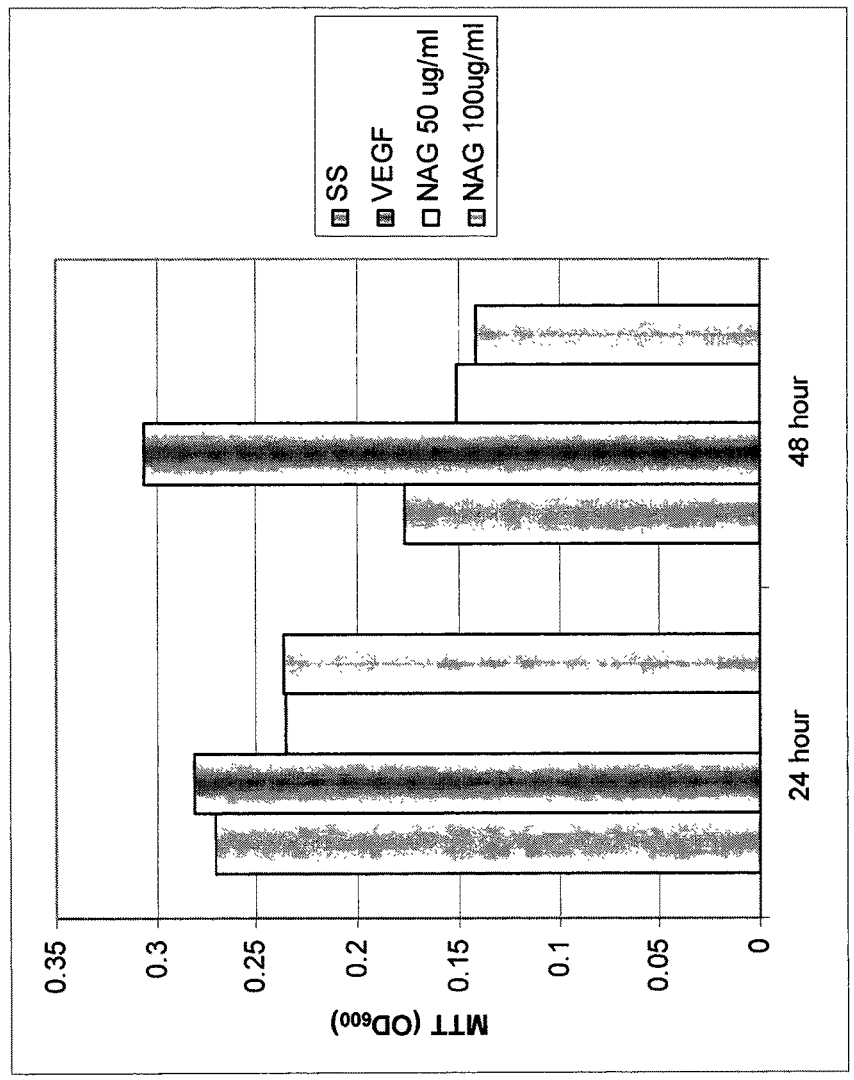

FIG. 25. pGlcNAc did not effect metabolic rate. For each time period (i.e., at 24 and 48 hours), the identity for each of the four bars (from left to right) is as follows: serum starvation (SS), VEGF, and pGlcNAc (NAG) at 50 and 100 µg/ml.

Figure 26:
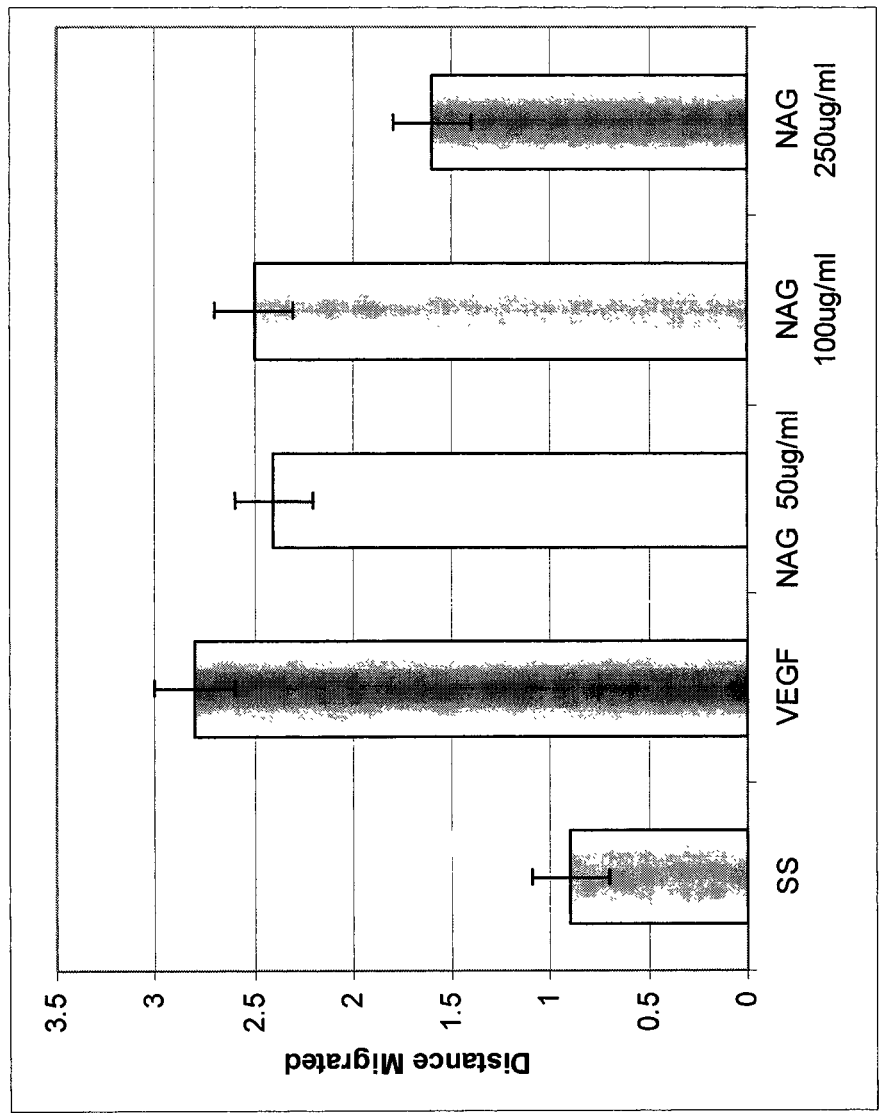

FIG. 26. pGlcNAc increased cell migration.

Figure 27:
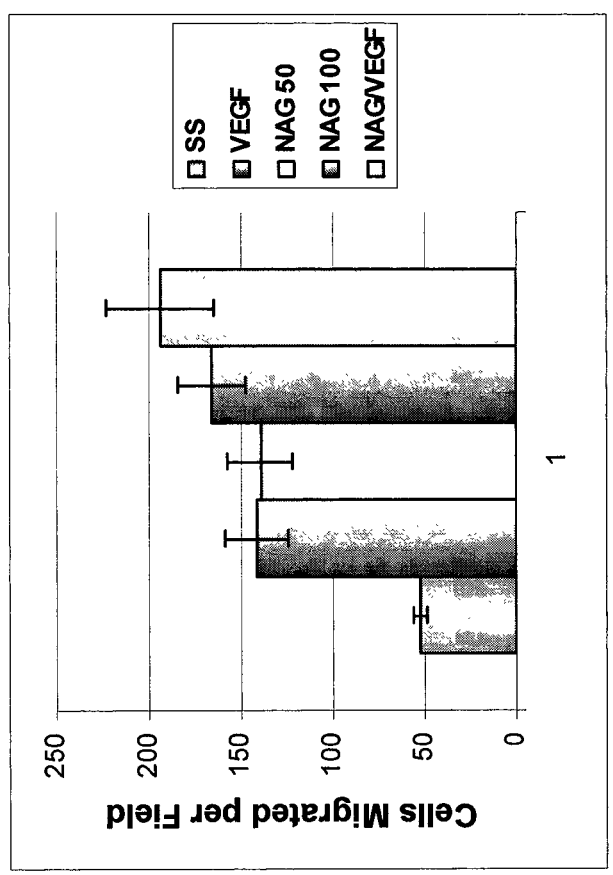

FIG. 27. pGlcNAc caused an increase in migration toward fibronectin. Identity for each of the five bars (from left to right) is as follows: serum starvation (SS), VEGF, pGlcNAc (NAG) at 50 and 100 250 µg/ml, and NAG/VEGF.

Figure 28:
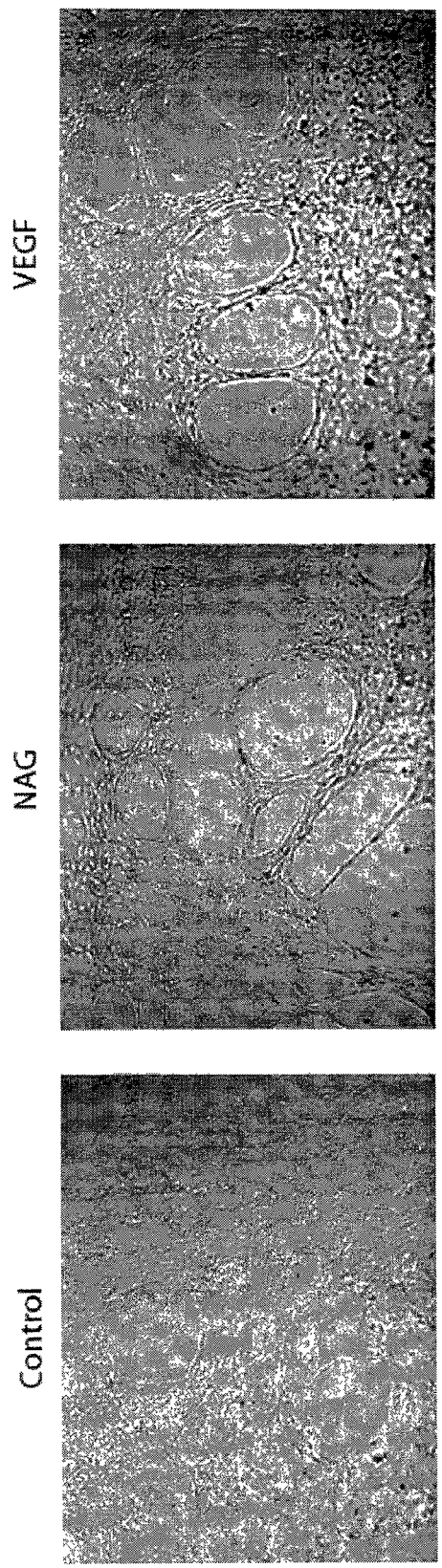

FIG. 28. pGlcNAc increased cord formation.

Figure 29A:
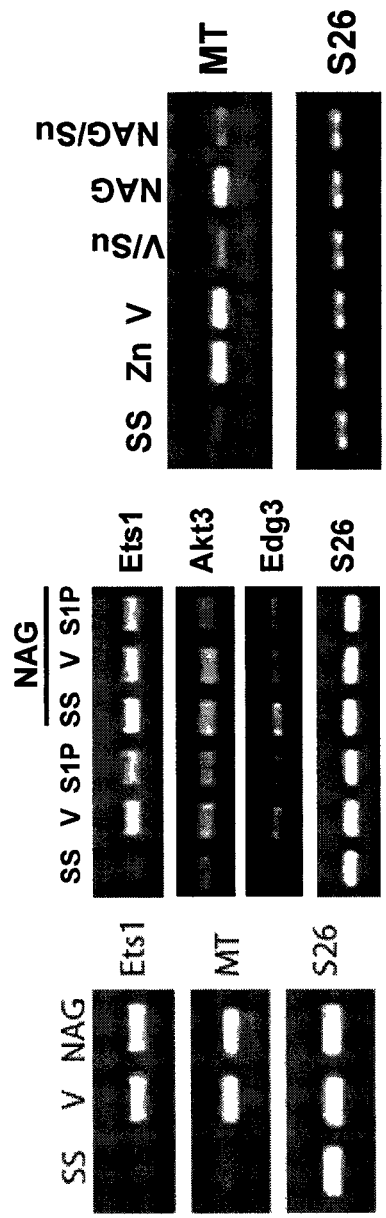
Figure 29C:
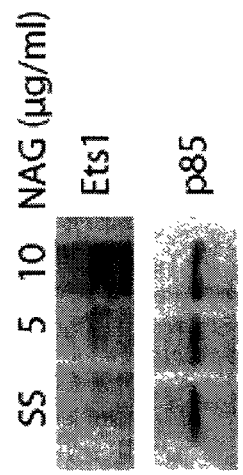
Figure 29B:
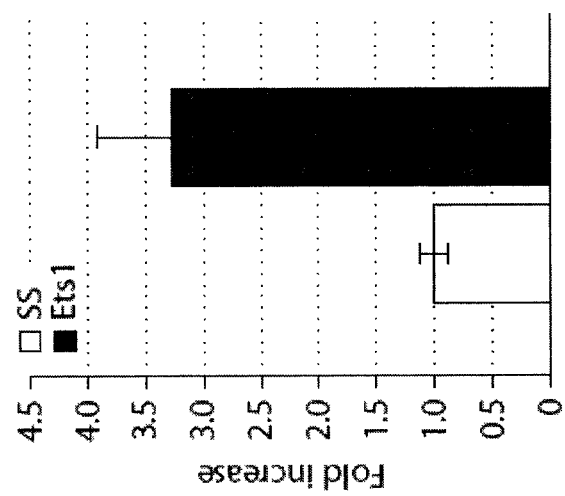

FIGS. 29A-C. pGlcNAc induced effectors involved in cell motility FIG. 29A: pGlcNAc treatment stimulated the expression of Ets1, metallothionein 2A (MT), Akt3 and Edg3. FIG. 29B: Real-time PCR demonstrates that Ets1 was induced approximately 2-fold by pGlcNAc treatment. FIG. 29C: Ets1 increase in message was accompanied by a higher protein expression as shown in the Western blot analysis.

Figure 30A:
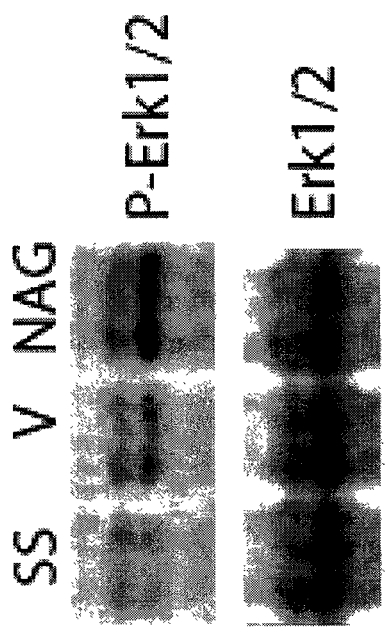
Figure 30B:
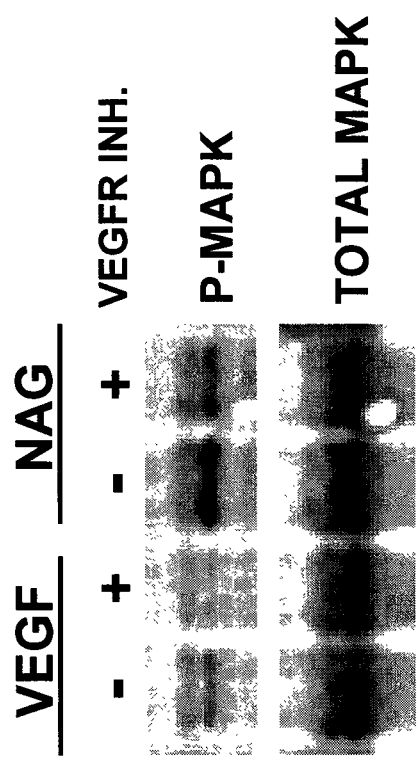

FIGS. 30A-B. pGlcNAc's induction of phospho-MAPK was VEGFR2-dependent FIG. 30A: pGlcNAc treatment resulted in a marked increase in the phosphorylation of MAPK. FIG. 30B: pGlcNAc's induction of phosphor-MAPK was dependent on VEGFR2.

Figure 31:
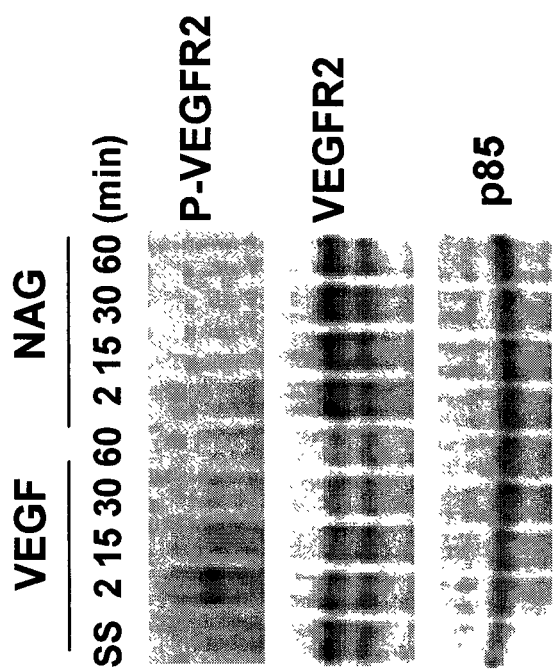

FIG. 31. pGlcNAc did not activate VEGFR2.

Figure 32A:
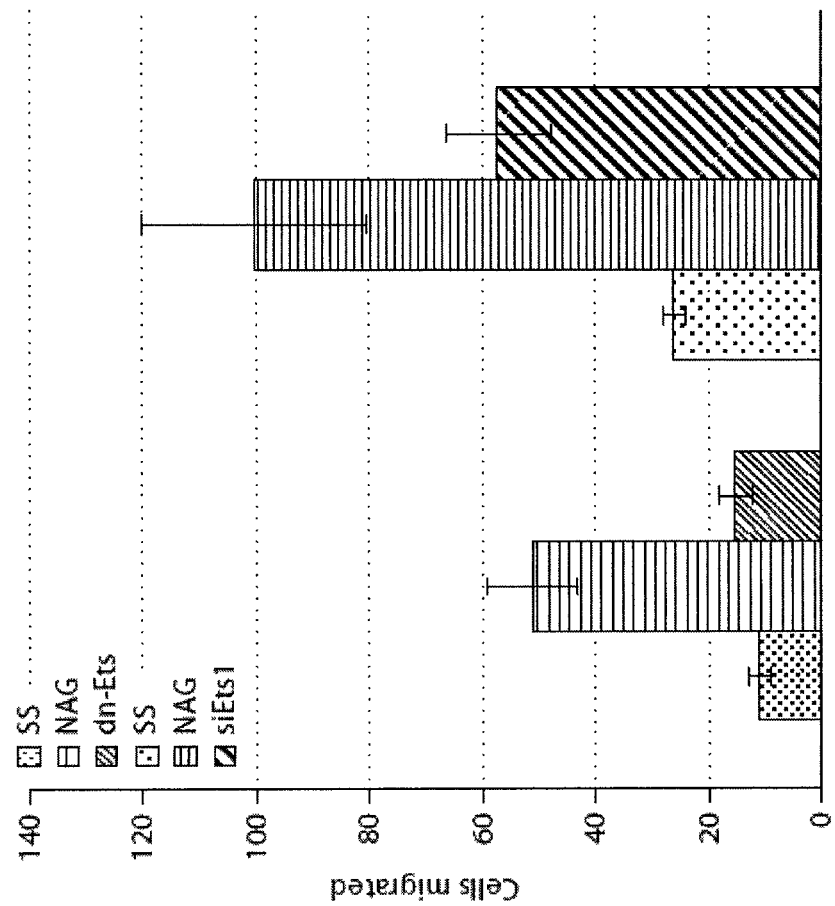
Figure 32B:
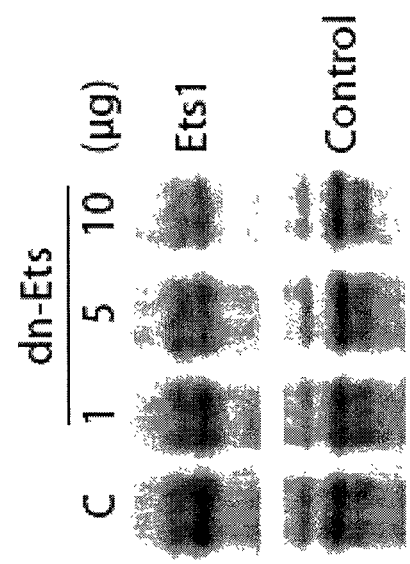
Figure 32C:
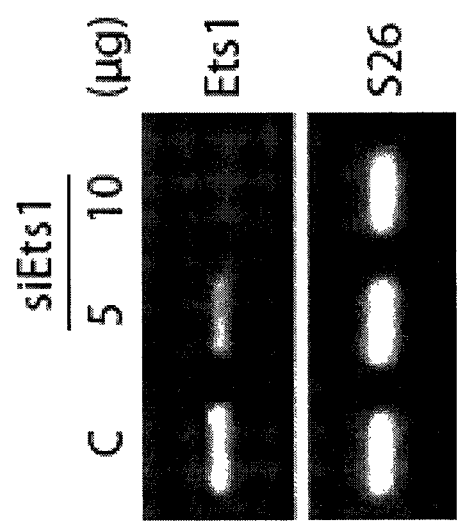

FIGS. 32A-B. pGlcNAc induced migration was Ets1 dependent. FIG. 32A: Inhibition of Ets1 activity in EC resulted in a marked decrease in EC migration in response to pGlcNAc. FIG. 32B: Ets1 protein expression decreased with the amount of dn-Ets construct. FIG. 32C: The resultant expression levels of Ets1 in EC transfected with 2 amounts of plasmid-containing RNAi directed against Ets1.

Figure 33A:
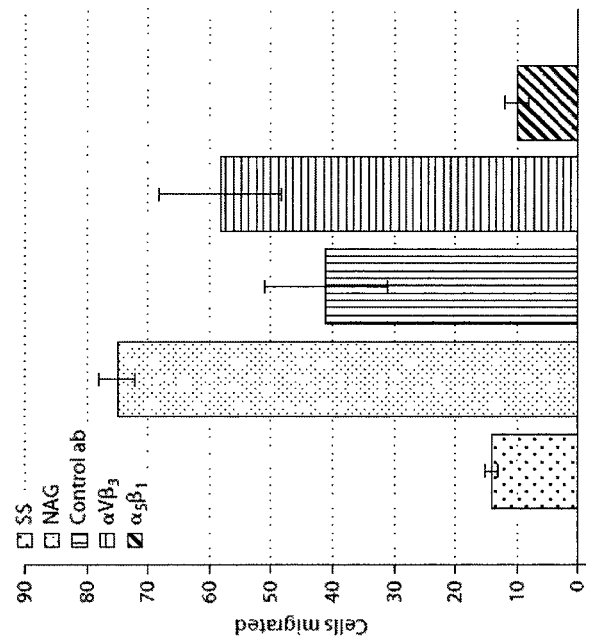
Figure 33B:
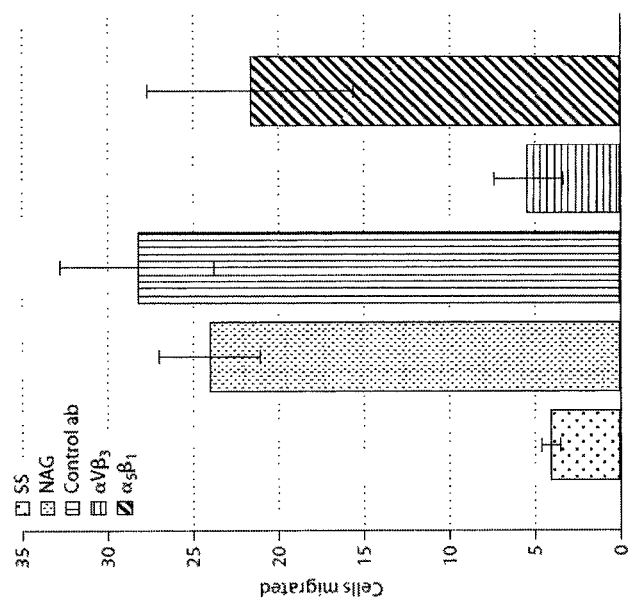

FIGS. 33A-B. pGlcNAc induced cell motility required integrin. FIG. 33A: The results when using antibodies directed against $\alpha V\beta_3$ or $\alpha_5\beta_1$ (CD49e) integrin in migration assays toward fibronectin (the $\alpha V\beta_3$ receptor). FIG. 33B: A similar experiment as in FIG. 33A using antibodies directed against $\alpha V\beta_3$ or $\alpha_5\beta_1$ (CD49e) in transwells coated with vitronectin.

Figure 34:
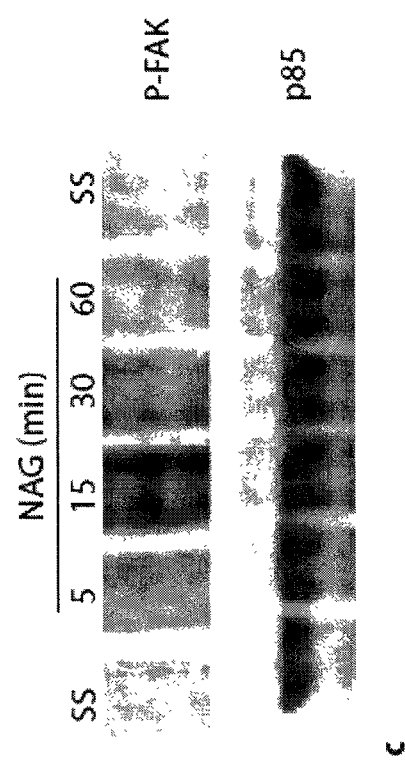

FIG. 34. pGlcNAc-induced cell motility and activation of FAK via integrin engagement.

Figures 35A, 35B:

FIGS. 35A-B. pGlcNAc can activate an integrin→Ets1 pathway leading to angiogenesis in a wound-healing model. FIG. 35A: Antibody blockade of $\alpha_5\beta_1$ integrin results in a reduction in pGlcNAc-induced Ets1 expression. FIG. 35B: This inhibition of Ets1 expression using a blockade of $\alpha_5\beta_1$ integrin is recapitulated on the protein level.

Figure 36A:
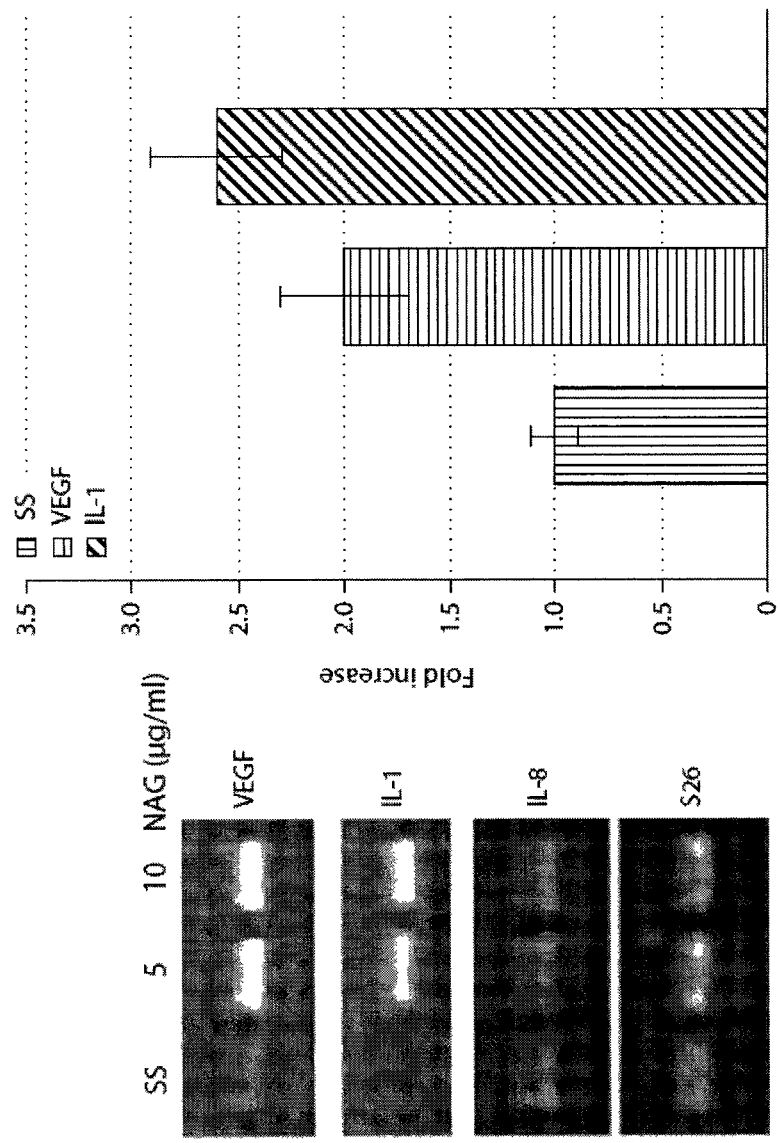
Figure 36B:
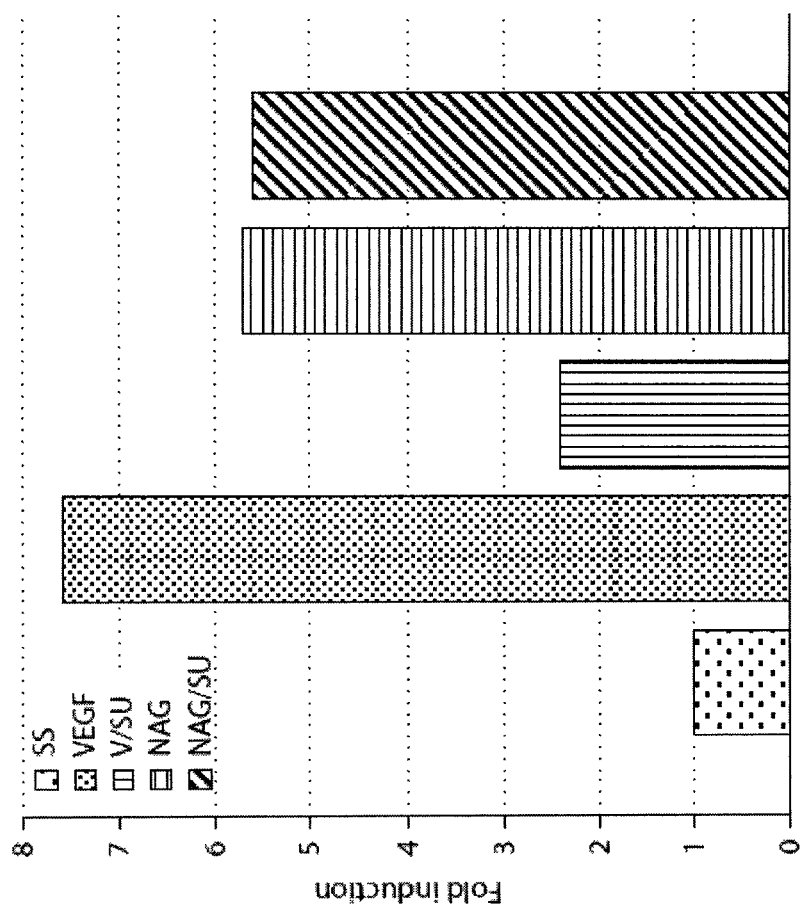

FIGS. 36A-B. pGlcNAc induced the expression of VEGF and IL-1. FIG. 36A: pGlcNAc increased expression of both VEGF and IL-1. FIG. 36B. Treatment of EC with its inhibitor blocked the induction of Ets1 by VEGF but had no effect on the induction of Ets1 by pGlcNAc.

Figure 37:
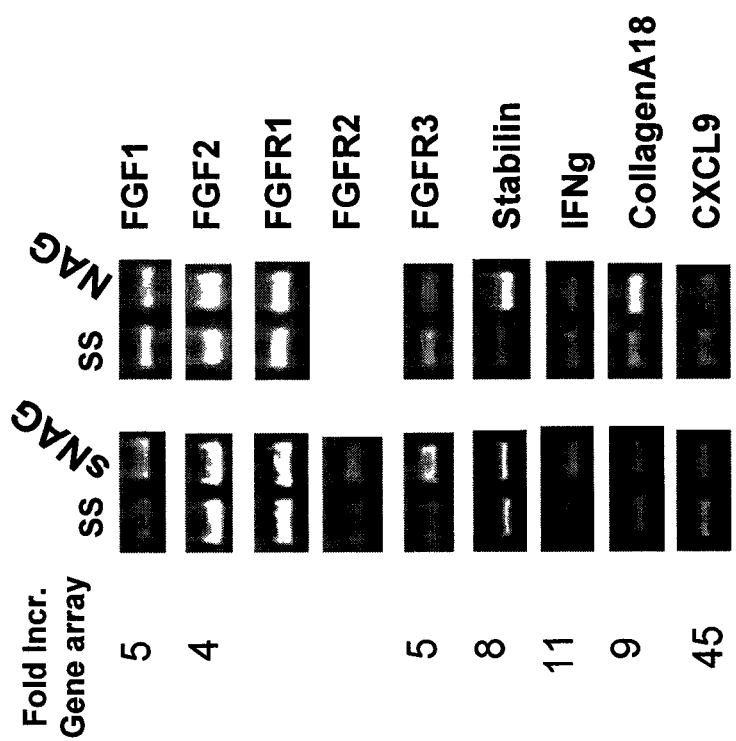

FIG. 37. sNAG induced the expression of FGF1, FGFR3, Stabilin, IFNg, CollagenA18, and CXCL9.

Figure 38:
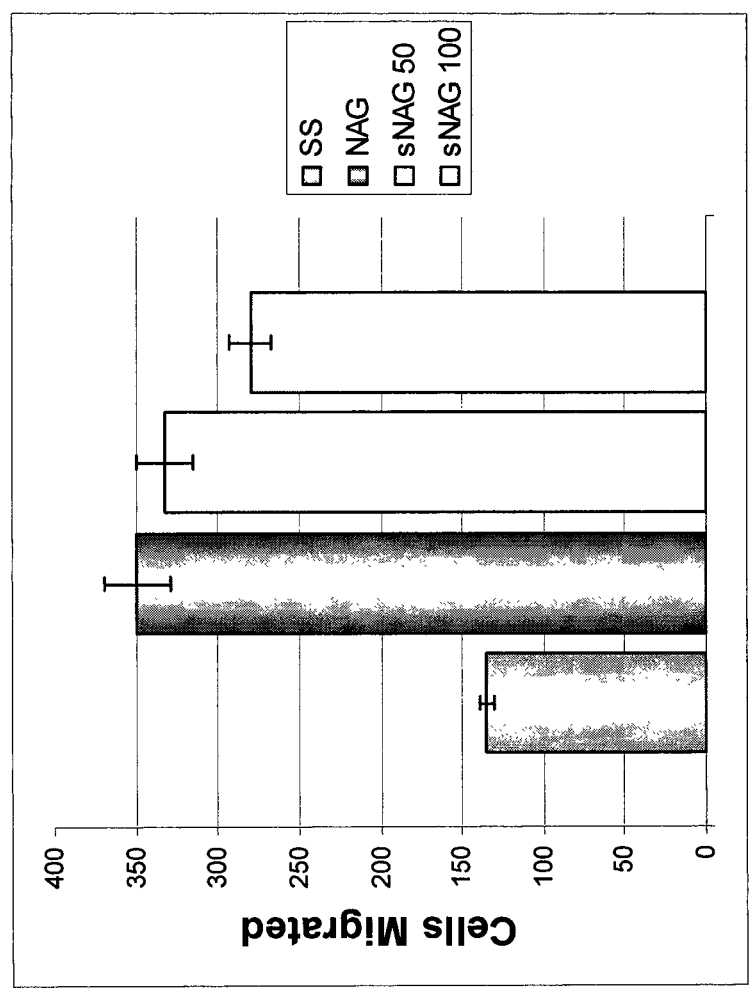

FIG. 38. sNAG increased cell migration. Identity for each of the four bars (from left to right) is as follows: serum starvation (SS), and sNAG at 50 and 100 µg/ml.

Figure 39:
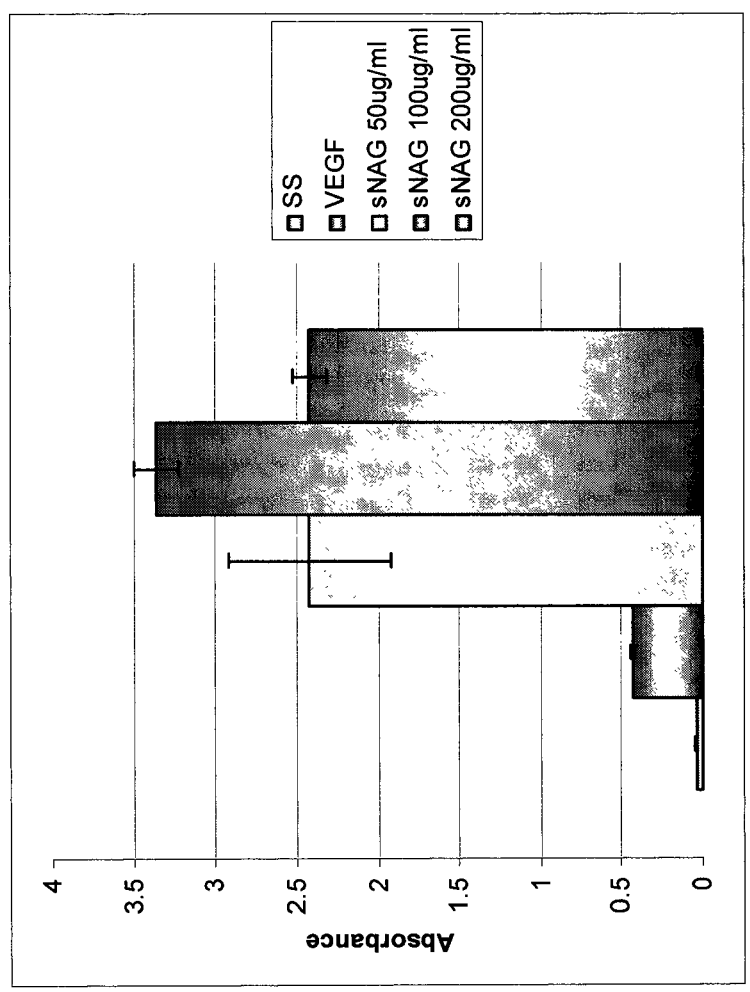

FIG. 39. sNAG induced marked increase in metabolic rate. Identity for each of the five bars (from left to right) is as follows: serum starvation (SS), VEGF, and sNAG at 50, 100 and 200 µg/ml.

Figure 40:
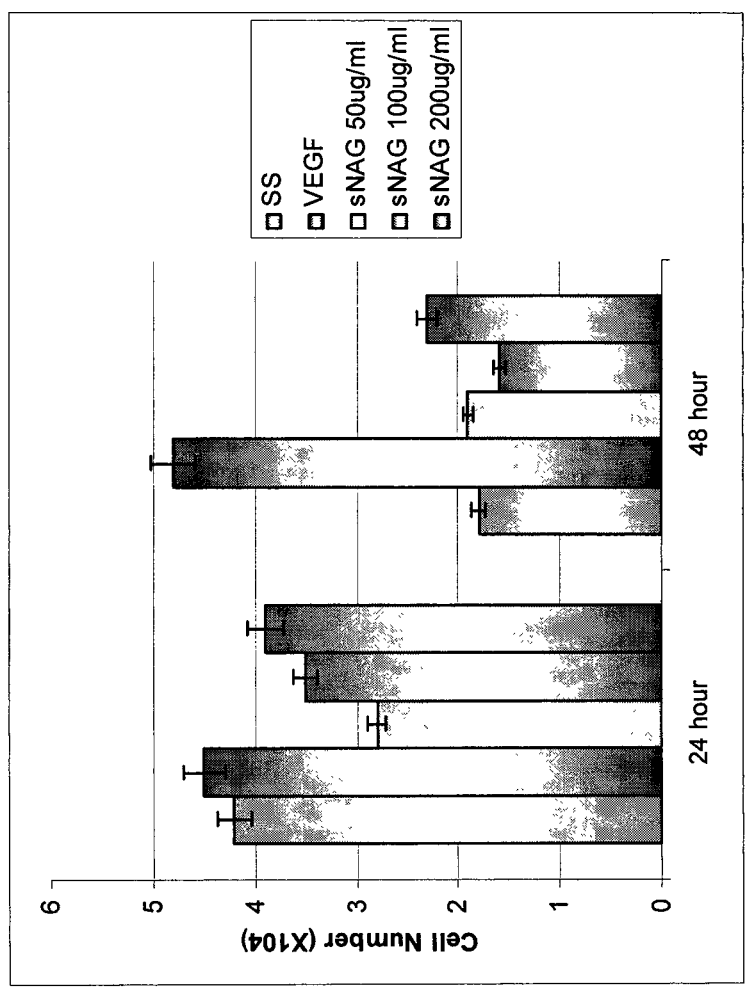

FIG. 40. sNAG did not protect EC from cell death induced by serum deprivation. For each time period (i.e., at 24 and 48 hours), the identity for each of the five bars (from left to right) is as follows: serum starvation (SS), VEGF, and sNAG at 50, 100 and 200 µg/ml.

Figure 41:
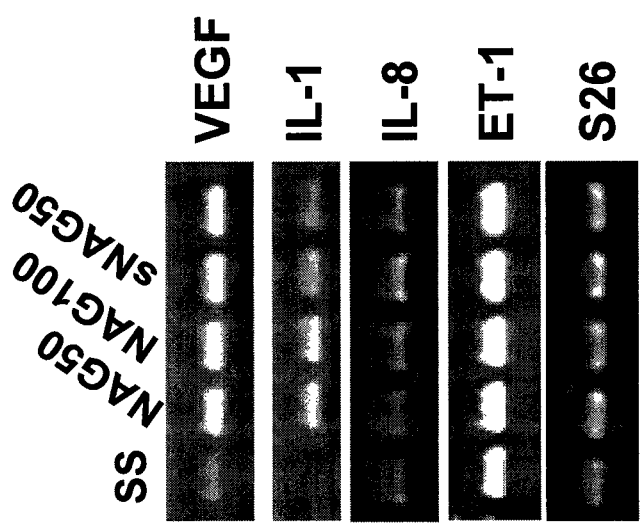

FIG. 41. sNAG induced the expression of VEGF and IL-1.

5. DETAILED DESCRIPTION

Sections 6.1 and 6.2 below clearly show that application of pGlcNAc, and in particular sNAG, to wounds in a diabetic mouse model for impaired wounds healing significantly shorten time for wound closure, wound reepithelialization, and wound contraction. Reepithelialization and granulation tissue were also enhanced in a shorter time for sNAG membrane treated mice. Application of the sNAG membrane also resulted in closure of all wounds in the treated animals in 28 days, compared to 85% in the untreated controls. Immunohistology data are consistent with the increased cell proliferation and appearance of new blood vessels (angiogenesis) in sNAG membrane treated mice. No foreign body response was observed throughout the study in any animal treated with the sNAG membrane.

These findings suggest that the pGlcNAc and sNAG membrane have clinical applications in the treatment of chronic wounds including diabetic ulcers, venous stasis ulcers, arterial insufficiency ulcers, and pressure ulcers. The pGlcNAc and sNAG membrane also have clinical utilities in the treatment of other open wounds, such as, but not limited to, surgical wounds and burn wounds.

5.1 Injuries for Treatment by the Present Methods and Compositions

The methods and compositions described herein are useful for treating wounds such as open wounds caused by incision (i.e., incision or incised wound), laceration, abrasion, puncture, penetration, gunshot, burning, etc. The methods and compositions described herein are particularly useful for treating chronic wounds, or patients who fail to heal normally, or in an orderly or timely fashion as in other human subjects.

A chronic wound is a wound that has failed to proceed through an orderly and timely series of events to produce a durable structural, functional, and cosmetic closure. Chronic wounds can be any wound that fail to heal properly, including a surgical wound (e.g., a skin graft donor site), a cutaneous ulcer (e.g., a diabetic ulcer, a venous stasis ulcer, an arterial insufficiency ulcer, or a pressure ulcer), or a burn wound.

Identifying the type of chronic wound being treated (e.g., diabetic, venous stasis, arterial insufficiency, and pressure) usually can be determined by considering the patient's history and performing a physical examination. Objective tools to confirm the diagnosis can include Doppler sonography to qualify and quantify vascular insufficiency: arterial or venous (deep, superficial, or mixed); transcutaneous oxygen tension (tcpO$_2$) measurements; ankle/brachial index; filament testing to quantify sensory neuropathy; measurement of laboratory markers for diabetes mellitus; histopathology of ulcer biopsies. In addition, there widely accepted criteria used to classify the stages of ulcers (e.g., National Pressure Ulcer Advisory Panel (NPUAP) for Pressure Ulcers: NPUAP Classification, Wagner's Classification for foot ulcers). Such methods are routinely practiced by the skilled artisan.

Identifying a patient who fails to heal normally, or in an orderly or timely fashion as in other human subjects can routinely be determined by, for example, considering the patient's history and performing a physical examination. Such determinations are routinely made by the skilled artisan.

5.2 Hemostatic Composition Materials

The hemostatic compositions are preferably formulated into wound dressings. The wound dressings can be made of any suitable natural or synthetic polymers or fibers. Examples of suitable polymers or fibers from which dressings can be prepared for practicing the methods and compositions described herein include cellulose polymers, xanthan, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. Other suitable classes of polymers or fibers include polyvinyledene fluorides and polyacrylonitriles. Examples of these polymers or fibers include those described in U.S. Pat. Nos. RE 30,351; 4,705,540, 4,717,393; 4,717,394; 4,912,197; 4,838,900; 4,935,490; 4,851,505; 4,880,442; 4,863,496; 4,961,539; and European Patent Application 0 219 878, all of which are incorporated by reference. The polymers or fibers can include at least one of either of cellulose polymers, polyamides, polyaramides, polyamide/imides or polyimides. In certain embodiments, the polymers or fibers include polyaramides, polyester, urethan and polytetrafluoroethylene. In preferred embodiments, polymerized N-acetylglucosamine fibers or derivatives thereof are used. In a most preferred embodiment, the polymer or fiber is poly-N-acetylglucosamine polymer or fiber or a derivative thereof. In certain embodiments, the poly-N-acetylglucosamine polymer or fiber has a β-1→4 configuration. In other embodiments, the poly-N-acetylglucosamine polymer or fiber has a α-1→4 configuration.

In specific embodiments, the polymer or fiber is chitin, chitosan, cellulose, nylon or PET (polyethylene terepthlate).

In a preferred embodiment, the polymer or fiber is biocompatible and/or biodegradable. Biocompatibility may be determined by a variety of techniques, including, but not limited to such procedures as the elution test, intramuscular implantation, or intracutaneous or systemic injection into animal subjects. Such tests are described in U.S. Pat. No. 6,686,342, which is incorporated by reference herein in its entirety. Biodegradable polymers preferably degrade within about 1 day, 2 day, 5 day, 8 day, 12 day, 17 day, 25 day, 30 day, 35 day, 40 day, 45 day, 50 day, 55 day, 60 day, 65 day, 70 day, 75 day, 80 day, 85 day, 90 day, 95 day, or 100 days after administration or implantation into a patient.

In certain aspects, the polymer or fiber is immunoneutral, in that they do not elicit an immune response.

Generally, the polymers or fibers are non-reactive in an intramuscular implantation test. In certain embodiments, the compositions comprise fibers as described in this section, wherein the fibers increases metabolic rate of serum-starved human umbilical cord vein endothelial cells in a MTT assay and/or does not rescue apoptosis of serum-starved human umbilical cord vein endothelial cells in a trypan blue exclusion test, and is non-reactive when tested in an intramuscular implantation test. In certain embodiments, the fibers increases metabolic rate of serum-starved human umbilical cord vein endothelial cells in a MTT assay and does not rescue apoptosis of serum-starved human umbilical cord vein endothelial cells in a trypan blue exclusion test, and is non-reactive when tested in an intramuscular implantation test In one embodiment, the hemostatic compositions comprise purified polymers or fibers, which may be about 100%, 99.9%, 99.8%, 99.5%, 99%, 98%, 95%, 90%, 80%, 70%, 60%, 50%, 40%, 30%, or 20% pure. In a preferred embodiment, the polymers or fibers used in the compositions and methods described herein are 90-100% pure.

In certain embodiments, the polymer or fiber that is used in a wound dressing is not one or more of the following: an ionic synthetic hydrogel such as, but not limited to, cross-linked poly(AAn-acrylic acid) and poly(AAm-dimethylaminoethyl methacrylate), poly(vinyl alcohol) (PVA), poly(ethylene glycol) (PEG), poly(N-vynl pyrrolidone), poly(methoxy-PEG methacrylate). In certain embodiments, the polymer or fiber is not one or more of: a poly-L-amino acid, such as poly-L-lysine, poly-L-arginine, poly-L-glutamic acid, poly-L-histidine, poly-D-glutamic acid or a mixture thereof. In certain embodiments, the polymer or fiber is not one or more of the following: an alginate polymer, such as sodium alginate, calcium alginate, strontium alginate, barium alginate, magnesium alginate or any other alginate or a mixture thereof. In certain embodiments, the polymer or fiber is not derived from one or more of the following: a shell fish, a crustacean, insect, fungi or yeasts. In certain embodiments, the compositions do not comprise collagen fibers. In certain embodiments, the compositions do not comprise elastin fibers. In other embodiments, these polymers or fibers are included in the compositions.

The polymers described herein are generally in the form of fibers comprising, polymers described herein. Thus, the polymers described herein can be in the form of fibers. Fibers are preferably about 2, 3, 4, 5, 8, 10, 20, 30, 40, 50, 60, 70, 80, 90, 100, 110, 120, 130, 140 or 150 microns in average length as determined by electron microscopy, or any range in between (e.g., 10-150 microns or 20-100 microns or 50-120 microns on average). The fibers are preferably nanofibers, with dimensions averaging 0.5-100 nm in thickness and/or diameter as determined by electron microscopy. In specific embodiments, the nanofibers are about 0.5, 1, 2, 5, 10, 20, 50 or 100 nm in thickness and/or diameter on average, or any range in between (e.g., 0.5-4 nm, 0.5-5 nm, 1-4 nm, 1-5 nm, 1-10 nm, 2-20 nm, 4-15 nm, 5-15 nm, 4-20 nm, 5-20 nm, 5-50 nm, etc.). In other embodiments, the fibers are preferably microfibers, with dimensions of about 0.20, 0.25, 0.30, 0.35, 0.40, 0.45, 0.50, 0.55, 0.60, 0.65, 0.75, 0.85 and 1 micron in thickness and/or diameter on average, or any range in between (e.g., 0.2-0.5 micron, 0.3-0.75 micron, 0.5-1 micron, and so on and so forth). As used herein, the metes and bound of the term "about" would readily be appreciated by those of skill in the art; generally, the term as used herein refers to a range of values 10% greater than and 10% less than the stated value.

In specific embodiments, the majority (greater than 50%, e.g., 60%, 70%, 80%, 90%, 95%, 98%, 99%, 99.5%, 99.8%, 99.9%, or 100%) of the fibers are less than about 30, 25, 20, 15, 10, 5, 4, or 3 microns in length. In specific embodiments, at least 50%, 60%, 70%, 80%, 90%, 95%, 98%, 99%, 99.5%, 99.8%, or 99.9% of the fibers are less than about 15 microns in length. In specific embodiments, all (100%) of the fibers are less than about 15 microns in length. In specific embodiments, the majority (greater than 50%, e.g., 60%, 70%, 80%, 90%, 95%, 98%, 99%, 99.5%, 99.8%, 99.9%, or 100%) of the fibers are about 5, 4, 3, 2, or 1 microns in length. In specific embodiments, at least 50%, 60%, 70%, 80%, 90%, 95%, 98%, 99%, 99.5%, 99.8%, or 99.9% of the fibers are less than about 4 microns in length. In specific embodiments, all (100%) of the fibers are about 4 microns in length.

Fibers are preferably about 0.1, 0.5, 1, 2, 3, 4, 5, 8, or 10 microns in average thickness or diameter as determined by electron microscopy, or any range in between (e.g., 0.1-10 microns or 0.5-5 microns or 1-2 microns on average). In specific embodiments, the majority (greater than 50%, e.g., 60%, 70%, 80%, 90%, 95%, 98%, 99%, 99.5%, 99.8%, 99.9%, or 100%) of the fibers have a thickness or diameter of about 1-2 microns. In specific embodiments, at least 50%, 60%, 70%, 80%, 90%, 95%, 98%, 99%, 99.5%, 99.8%, or 99.9% of the fibers have a thickness or diameter of about 1-2 microns. In specific embodiments, all (100%) of the fibers have a thickness or diameter of about 1-2 microns.

In certain embodiments, the majority (greater than 50%, e.g., 60%, 70%, 80%, 90%, 95%, 98%, 99%, 99.5%, 99.8%, 99.9%, or 100%) of the fibers are less than about 15 microns in length and have a thickness or diameter of about 1-2 microns.

In certain preferred embodiments, the polymers or fibers are formulated as wound dressings, which can be in the form of barriers, membranes, or films. Alternatively, the polymers or fibers are added to dressing backings, such as barriers, membranes, or films. A barrier, membrane, or film can be supplied in a variety of standard sizes, which can be further cut and sized to the area being treated. The backing can be a conventional dressing material, such as a bandage or gauze to which a polymer or fiber is added or coated on, prior to application to the patient. Alternatively, the polymer or fiber can be formulated as a barrier, membrane, or film made out of strings, microbeads, microspheres, or microfibrils, or the composition can be formulated as a barrier-forming mat. As pointed out herein, the polymers can be present in the form of fibers. As such, throughout the specification, whether or not explicitly recited, it is understood that any embodiments referring to polymers described herein, the polymers can be present in the form of fibers.

In certain embodiments, at least 75%, at least 85%, at least 90%, or at least 95% of a dressing is composed of one or more of the polymers listed above.

In certain aspects, a dressing does not contain a conventional dressing material such as a gauze or bandage. In such embodiments, the polymer itself if formulated as the wound dressing.

In one embodiment, the compositions described herein comprise more than one type of polymer (e.g., poly-β-1→4-N-acetylglucosamine and cellulose).

In certain aspects, the polymer (e.g., the poly-β-1→4-N-acetylglucosamine or derivative thereof) is the only active ingredient in a dressing. In other embodiments, the dressing comprises additional active ingredients to promote wound healing, such as growth factors. In specific embodiments, the growth factor is PDGF-AA, PDGF-AB, PDGF-BB, PDGF-CC, PDGF-DD, FGF-1, FGF-2, FGF-5, FGF-7, FGF-10, EGF, TGF-α, (HB-EGF), amphiregulin, epiregulin, betacellulin, neuregulins, epigen, VEGF-A, VEGF-B, VEGF-C, VEGF-D, VEGF-E, placenta growth factor (PLGF), angiopoietin-1, angiopoietin-2, IGF-I, IGF-II, hepatocyte growth factor (HGF), or macrophage-stimulating protein (MSP).

However, in other aspects, a dressing does not comprise a significant amount of protein material. In specific embodiments, the protein content of a dressing is no greater than 0.1%, 0.5% or 1% by weight. In other embodiments, the protein content of a dressing is undetectable by Coomassie staining.

A dressing may contain collagen, although in certain aspects a dressing does not contain collagen.

The dressing may also contain antimicrobial agents to prevent infection of the wounds.

In a preferred embodiment, zinc is also included in a dressing. In addition to its antimicrobial properties, zinc also plays a role in wound healing (see Andrews et al., 1999, Adv Wound Care 12:137-8). The zinc is preferably added in the form of a salt, such as zinc oxide, zinc sulphate, zinc acetate or zinc gluconate.

5.2.1 Poly-β-1→4-N-acetylgulcosamine ("pGlcNAc" or "NAG")

This section incorporates by reference U.S. Pat. Nos. 5,622,834; 5,623,064; 5,624,679; 5,686,115; 5,858,350; 6,599,720; 6,686,342; and 7,115,588 that describe in detail the structure of poly-β-1→4-N-acetylglucosamine polymer that is a preferred embodiment, each of which is incorporated by reference herein in its entirety.

In preferred embodiments, poly-β-1→4-N-acetylglucosamine is derived from a process comprising a) treating a microalga comprising a cell body and a poly-β-1→4-N-acetylglucosamine polymer fiber with a biological agent (such as hydofluoric) capable of separating the N-acetylglucosamine polymer fiber from the cell body for a sufficient time so that the poly-β-1→4-N-acetylglucosamine polymer fiber is released from the cell body; b) segregating the poly-β-1→4-N-acetylglucosamine polymer fiber from the cell body; and c) removing contaminants from the segregated poly-β-1→4-N-acetylglucosamine polymer fiber, so that the poly-β-1→4-N-acetylglucosamine polymer is isolated and purified.

As used herein derivatives of a poly-β-1→4-N-acetylglucosamine polymer include: a semi-crystalline form of a poly-β-1→4-N-acetylglucosamine polymer; a poly-β-1→4-N-acetylglucosamine polymer comprising about 50 to about 150,000 N-acetylglucosamine monosaccharides covalently attached in a β-1→4 conformation, and said polymer has a molecular weight of about 10,000 daltons to about 30 million daltons; a poly-β-1→4-N-acetylglucosamine polymer comprising about 50 to about 50,000 N-acetylglucosamine monosaccharides covalently attached in a β-1→4 conformation, and said polymer has a molecular weight of about 10,000 daltons to about 10 million daltons; a poly-β-1→4-N-acetylglucosamine polymer comprises about 50 to about 10,000 N-acetylglucosamine monosaccharides covalently attached in a β-1→4 conformation, and said polymer has a molecular weight of about 10,000 daltons to about 2 million daltons; a poly-β-1→4-N-acetylglucosamine polymer comprising about 50 to about 4,000 N-acetylglucosamine monosaccharides covalently attached in a β-1→4 conformation, and said polymer has a molecular weight of about 10,000 daltons to about 800,000 daltons; a semi-crystalline poly-β-1→4-N-acetylglucosamine polymer comprising at least one N-acetylglucosamine monosaccharide that is deacetylated, and wherein at least 10%, 20%, 30%, 40%, 50%, 60%, 70%, 80%, 90%, or 100% of said N-acetylglucosamine monosaccharides are acetylated; and a semi-crystalline poly-β-1→4-N-acetylglucosamine polymer comprising at least one N-acetylglucosamine monosaccharide that is deacetylated, and wherein at least 20-70% (or any range in between the foregoing embodiments) of said N-acetylglucosamine monosaccharides are deacetylated.

Derivatives of a poly-β-1→4-N-acetylglucosamine polymer also include compositions that are 100%, 90%, 80%, 70%, 60%, 50%, 40%, 30%, 20%, 10% or less poly-β-1→4-N-acetylglucosamine.

Other derivatives of poly-β-1→4-N-acetylglucosamine may also be used in the composition described herein. For example, sulfated poly-β-1→4-N-acetylglucosamine derivatives, phosphorylated poly-β-1→4-N-acetylglucosamine derivatives, or nitrated poly-β-1→4-N-acetylglucosamine derivatives may be used. Additionally, one or more of the monosaccharide units of the poly-β-1→4-N-acetylglucosamine may contain one or more sulfonyl groups one or more O-acyl groups. In addition, one or more of the monosaccharides of the deacetylated poly-β-1→4-N-acetylglucosamine may contain an N-acyl group. One or more of the monosaccharides of the poly-β-1→4-N-acetylglucosamine or of its deacetylated derivative, may contain an O-alkyl group. One or more of the monosaccharide units of the poly-β-1→4-N-acetylglucosamine may be an alkali derivative. One or more of the monosaccharide units of the deacetylated derivative of poly-β-1→4-N-acetylglucosamine may contain an N-alkyl group. One or more of the monosaccharide units of the deacetylated derivative of poly-β-1→4-N-acetylglucosamine may contain at least one deoxyhalogen derivative. One or more of the monosaccharide units of the deacetylated derivative of poly-β-1→4-N-acetylglucosamine may form a salt. One or more of the monosaccharide units of the deacetylated derivative of poly-β-1→4-N-acetylglucosamine may form a metal chelate. Preferably, the metal is zinc. One or more of the monosaccharide units of the deacetylated derivative of poly-β-1→4-

N-acetylglucosamine may contain an N-alkylidene or an N-arylidene group. Methods of making such derivatives are described in U.S. Pat. No. 5,623,064, which is incorporated by reference herein in its entirety.

5.3 Irradiation to Reduce Molecular Weight and Length

The polymers or fibers can be in irradiated as dry polymers or fibers or polymer or fiber membranes, as described above. Alternatively, the polymers or fibers can be irradiated when wet.

In preferred embodiments, the polymers or fibers are formulated into a suspension/slurry or wet cake for irradiation. Irradiation can be performed prior to, concurrently with or following the formulation of the polymers or fibers into a dressing. Generally, the polymer or fiber content of suspensions/slurries and wet cakes can vary, for example from about 0.5 mg to about 50 mg of polymer or fiber per 1 ml of distilled water are used for slurries and from about 50 mg to about 1000 mg of polymer or fiber per 1 ml of distilled water are use for wet cake formulations. The polymer or fiber may first be lyophilized, frozen in liquid nitrogen, and pulverized, to make it more susceptible to forming a suspension/slurry or wet cake. Also, the suspensions/slurries can be filtered to remove water such that a wet cake is formed. In certain aspects, the polymer or fiber is irradiated as a suspension comprising about 0.5 mg, 1 mg, 2 mg, 3 mg, 4 mg, 5 mg, 6 mg, 7 mg, 8 mg, 9 mg, 10 mg, 12 mg, 15 mg, 18 mg, 20 mg, 25 mg or 50 mg of polymer or fiber per ml of distilled water, or any range in between the foregoing embodiments (e.g., 1-10 mg/ml, 5-15 mg/ml, 2-8 mg/ml, 20-50 mg/ml, etc.). In other aspects, the polymer or fiber is irradiated as a wet cake, comprising about 50-1,000 mg polymer or fiber per 1 ml of distilled water. In specific embodiments, the wet cake comprises about 50, 100, 200, 300, 400, 500, 600, 700, 800, 900 or 1000 mg of polymer or fiber per 1 ml distilled water, or any range in between (e.g., 100-500 mg/ml, 300-600 mg/ml, 50-1000 mg/ml, etc.).

The irradiation is preferably in the form of gamma radiation, e-beam radiation, or x-rays. Two sources of irradiation are preferred: radioactive nuclides and electricity. In specific embodiment, the radioactive nuclides are cobalt-60 and cesium-137. Both of these nuclides emit gamma rays, which are photons containing no mass. The gamma rays have energies from 0.66 to 1.3 MeV. Using electricity, electrons are generated and accelerated to energies up to 10 MeV or higher. When irradiating polymers or fibers to reduce their size, a consideration to take into account is that the depth of penetration of materials with densities similar to water by 10 MeV electrons is limited to about 3.7 cm with one-sided exposure or about 8.6 cm with two-sided exposure. Depth of penetration decreases at lower electron energies. Electron energy can be converted to x-rays by placing a metal (usually tungsten or tantalum) target in the electron beam path. Conversion to x-rays is limited to electrons with energies up to 5 MeV. X-rays are photons with no mass and can penetrate polymers or fibers similar to gamma rays. There is only about 8% efficiency in the conversion of electron energy to x-ray energy. High powered electron beam machines are needed in x-ray production facilities to account for the low conversion efficiency.

Preferably, the irradiation is gamma irradiation.

The absorbed dose of radiation is the energy absorbed per unit weight of product, measured in gray (gy) or kilogray (kgy). For dried polymers or fibers, the preferred absorbed dose is 500-2,000 kgy of radiation, most preferably 750-1,250 kgy of radiation, while for wet polymers or fibers, the preferred absorbed dose is about 100-500 kgy of radiation, most preferably about 150-250 kgy of radiation.

The dose of radiation can be described in terms of its effect on the length of the polymers or fibers. In specific embodiments, the dose of radiation used preferably reduces the length of the polymer or fiber by anywhere from about 10% to 90% of the starting length of the polymer or fiber, respectively. In specific embodiments, the average length is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the length of the polymer or fiber to anywhere from 30 to 100 microns. In specific embodiments, and depending on the starting fiber length, the average length of the polymer or fiber is reduced to less than about 15 microns, less than about 14 microns, less than about 13 microns, less than about 12 microns, less than about 11 microns, less than about 10 microns, less than about 5 microns, less than about 4 microns, less than about 3 microns, less than 2 microns, or less than 1 microns. In certain embodiments, the length of the majority (greater than 50%, e.g., 60%, 70%, 80%, 90%, 95%, 98%, 99%, 99.5%, 99.8%, 99.9%, or 100%) of the polymers or fibers is reduced to no greater than 40 microns, no greater than about 30 microns, no greater than about 20 microns, no greater than about 15 microns, no greater than about 10 microns, or no greater than about 5 microns. Any ranges between the foregoing length are also encompassed; for example, in certain embodiments, irradiation of the polymers or fibers reduces the length of the majority (greater than 50%, e.g., 60%, 70%, 80%, 90%, 95%, 98%, 99%, 99.5%, 99.8%, 99.9%, or 100%) of the fibers to anywhere between about 1 to 20 microns, between about 2 to 15 microns, between about 4 to 10 microns, and so on and so forth.

The dose of radiation can also be described in terms of its effect on the molecular weight of the polymer or fiber. In specific embodiments, the dose of radiation used preferably reduces the molecular weight of the polymer or fiber by anywhere from about 10% to 90% of the starting weight of the polymer or fiber. In specific embodiments, the average molecular weight is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the molecular weight of the polymer or fiber to anywhere from 1,000 to 1,000,000 daltons. In specific embodiments, and depending on the starting molecular weight, the average molecular weight of the polymer or fiber is reduced to less than 1,000,000 daltons, less than 750,000 daltons, less than 500,000 daltons, less than 300,000 daltons, less than 200,000 daltons, less than 100,000 daltons, less than 50,000 daltons, less than 25,000 daltons, less than 10,000 daltons, or less than 5,000 daltons. In certain embodiments, the average molecular weight is reduced to no less than 500 daltons, no less than 1,000 daltons, no less than 2000 daltons, no less 3,500 daltons, no less than 5,000 daltons, no less than 7,5000 daltons, no less than 10,000 daltons, no less than 25,000 daltons, no less than 50,000 daltons, or no less than 100,000 daltons. Any ranges between the foregoing average molecular weights are also encompassed; for example, in certain embodiments, irradiation of the polymer or fiber reduces the average molecular weight to anywhere between 10,000 to 100,000 daltons, between 1,000 and 25,000 daltons, between 50,000 and 500,000 daltons, and so on and so forth.

In preferred embodiments, the irradiation used is gamma irradiation.

Following irradiation, slurries can be filtered and dried, and wet cakes can be dried, to form dressings that are useful in the practice described herein.

5.3.1 Shortened poly-β-1→4-N-acetylgulcosamine ("sNAG")

The poly-β-1→4-N-acetylgulcosamine as described in Section 5.2 above can be subject to irradiation as described in Section 5.3 above to reduce the length of its fibers to form shortened poly-β-1→4-N-acetylgulcosamine, and thus reducing its molecular weight without disturbing its microstructure. The infrared spectrum (IR) of the shortened poly-β-1→4-N-acetylgulcosamine (sNAG) is substantially similar or equivalent to that of the non-irradiated poly-β-1→4-N-acetylgulcosamine (NAG).

In certain embodiments, the majority (greater than 50%, e.g., 60%, 70%, 80%, 90%, 95%, 98%, 99%, 99.5%, 99.8%, 99.9%, or 100%) of the fibers of sNAG is less than 15 microns in length. In one aspect, the majority of the fibers of sNAG have a thickness or diameter of about 1-2 microns. The length of the fibers can be measured by any method known to one skilled in the art, for example, by scanning electron microscopy (SEM).

In one aspect, sNAG increases the metabolic rate of serum-starved human umbilical cord vein endothelial cell (EC) in a MTT assay. A MTT assay is a laboratory test and a standard colorimetric assay (an assay which measures changes in color) for measuring cellular proliferation (cell growth). Briefly, yellow MTT (3-(4,5-Dimethylthiazol-2-yl)-2,5-diphenyltetrazolium bromide, a tetrazole) is reduced to purple formazan in the mitochondria of living cells. This reduction takes place only when mitochondrial reductase enzymes are active, and therefore conversion can be directly related to the number of viable (living) cells. The metabolic rate of cells may be determined by other techniques commonly known to the skilled artisan.

In another aspect, sNAG does not rescue apoptosis of serum-starved EC in a trypan blue exclusion test. A trypan blue exclusion test is a dye exclusion test used to determine the number of viable cells present in a cell suspension. It is based on the principle that live cells possess intact cell membranes that exclude certain dyes, such as trypan blue, Eosin, or propidium, whereas dead cells do not. The viability of cells may be determined by other techniques commonly known to the skilled artisan.

In another aspect, sNAG is non-reactive when tested in an intramuscular implantation test. In one aspect, an intramuscular implantation test is an intramuscular implantation test—ISO 4 week implantation, as described in Section 6.4.2 below.

In certain embodiments, sNAG comprises fibers, wherein the majority of the fibers are less than about 15 microns in length, and is non-reactive when tested in an intramuscular implantation test.

In certain embodiments, sNAG (i) comprises fibers, wherein the majority of the fibers are less than about 15 microns in length, and (ii) (a) increases the metabolic rate of serum-starved EC in a MTT assay and/or does not rescue apoptosis of serum-starved EC in a trypan blue exclusion test, and (b) is non-reactive when tested in an intramuscular implantation test.

5.4 Methods for Using the Hemostatic Compositions

Described herein are methods for treating a wound in patients. The methods generally comprise applying a dressing to a wound in a patient, wherein the dressing comprises or consists of any of the polymers or fibers listed in Sections 5.2 and 5.3 above.

The patient is preferably a mammal, most preferably a human.

In certain embodiments, the patient is an adult, an adolescent, or an infant. In one embodiment, the patient is a human older than age 45. In one embodiment, the patient is a woman who is not pregnant.

In certain embodiments, the mammal is a livestock mammal (e.g., cow or sheep or pig) or household pet (e.g., cat or dog).

In certain embodiments, methods are described herein for treating a wound in patients who do not normally heal in an orderly or timely fashion as other human subjects. The patient is preferably a human such as a diabetic, a smoker, a hemophiliac, an HIV-infected person, an obese person, a person undergoing radiation therapy, or a person with venous stasis ulcer. In one aspect, the patient is a person with venous stasis ulcer. In certain aspects, the wound is a surgical wound or a burn wound. In certain other aspects, the wound is a chronic wound such as a diabetic ulcer, a venous stasis ulcer, an arterial insufficiency ulcer, or a pressure ulcer.

In certain embodiments, methods are described herein for treating a chronic wound in patients, wherein the chronic wound does not heal in an orderly or timely fashion. In certain embodiments, the wound is a chronic wound such as a diabetic ulcer, a venous stasis ulcer, an arterial insufficiency ulcer, or a pressure ulcer. In one aspect, the chronic wound is a venous stasis ulcer.

The hemostatic compositions and methods described herein advantageously reduces the labor and cost of nursing care associated with wounds, especially chronic wounds. Wound dressings currently available on the market require changing every approximately two days; in contrast, in the present methods the wound dressings are changed or reapplied every 3-35 days. In specific embodiments, the wound dressings are changed or reapplied every 4-35 days, every 5-35 days, every 6-35 days or every 7-35 days. In certain aspect, the wound dressings are changed or reapplied every 3-10 days, every 4-14 days, every 5-12 days, every 7-14 days, every 7-28 days, every 7-21 days, every 14-28 days, or any range between 3, 4, 5, 6, or 7 days at the lower end to every 8, 9, 10, 12, 14, 18, 21, 24, 28, 30 or 35 days on the higher end. In one aspect, the wound dressings are changed or reapplied only one time at the beginning of treatment. In another aspect, the wound dressings are changed or reapplied once per week during treatment. In another aspect, the wound dressings are changed or reapplied every other week during treatment. In another aspect, the wound dressings are changed or reapplied every two weeks, three weeks, or four weeks during treatment. The present methods reduce the frequency of wound dressing changes by at least 50%, and can reduce the frequency of wound dressing changes by 100%, 200%, 500% or even more. The specific frequency for changing or reapplying the wound dressings will vary depending on the needs of the individual; i.e., depending on the size, classification and responsiveness of the wound to the dressing. The frequency can be determined by standard clinical techniques, and need not be at fixed intervals. Rather, the frequency can be varied over time, depending on the needs of the individual. For example, as a chronic wound begins to heal, the frequency of wound dressing changes or reapplications are reduced.

In certain aspects, the wound dressing is applied to the wound, where it may remain until it is removed or biodegrades. More preferably, the wound dressing is reapplied (without removing the previous wound dressing) or changed (by removing the previous wound dressing and applying a new dressing) at least once, but can be reapplied or changed at the frequencies described above for the duration of the wound. Preferably, the wound dressing is reapplied or changed at least twice, at least three times, at least four times or more. The therapeutic regimens can be performed over a period of a few weeks (e.g., 2-8 weeks) to several months (e.g., from 2-4 months up to 6-12 months or longer, and any range in between).

Advantageously, the dressings also reduce overall wound healing time. For example, in the diabetic mouse model described in Section 6 below, the pGlcNAc dressing reduced the time to achieve wound closure one week faster than in control mice. Thus, in addition to reducing the number of dressing changes for a given wound, the methods described herein are useful for reducing wound closure time. Accordingly, in certain aspects, methods for reducing the wound closure time of a chronic wound are provided, comprising topically applying a dressing to a chronic wound in a patient, wherein the dressing comprises or is composed of one or more of the polymers listed in Sections 5.2 and 5.3 above. Optionally, the application is repeated one or more times in accordance with the therapeutic regimens described in this section. In certain aspects, the wound closure time is reduced by at least 10%, by at least 20%, by at least 30%, by at least 40% or by at least 50%.

Most preferably, the polymer from which a dressing is made is a biocompatible and/or immunoneutral polymer, including but not limited to poly-β-1→4-N-acetylglucosamine or a derivative thereof. In a preferred embodiment, the poly-β-1→4-N-acetylglucosamine or a derivative thereof is a microalgal poly-β-1→4-N-acetylglucosamine or a derivative thereof. In certain aspects, the poly-β-1→4-N-acetylglucosamine or a derivative thereof is not from a shellfish or crustacean source.

The aforementioned methods can be used in conjunction with other standard care procedures for chronic wounds. For example, the methods can be used in conjunction with one or more of the following treatments for cutaneous ulcer therapy: removal of necrotic or infected tissue (debridement); off-loading; compression therapy for venous stasis ulcers; establishment of adequate blood circulation; maintenance of a moist wound environment; management of wound infection; wound cleansing; nutritional support, including blood glucose control for subjects with diabetic ulcers; bowel and bladder care for subjects with pressure ulcers at risk for contamination.

For burn wounds, standard care procedures that may be used in conjunction with the methods described herein include: hemodynamic resuscitation; management of co-morbidities; timely burn debridement and excision; wound closure; management of wound infection; pain control; nutritional support; measures to inhibit excessive scar formation; and rehabilitation, including passive range of motion when burns overlie joints.

5.5 Kits

A kit is also provided which comprises any of the above described dressing materials. The dressing is preferably contained within a sealed, water proof, sterile package which facilitates removal of the composition without contamination. Materials from which containers may be made include aluminum foil, plastic, or another conventional material that is easily sterilized. The kit can contain a single dressing or multiple dressings, preferably wherein each is provided in a separate, waterproof, sterile package. The dressing may further comprise wound healing agents or antimicrobials, as described in Sections 5.2 and 5.3 above.

In another embodiment, a container having dual compartments is provided. A first compartment contains the dressing, while the second compartment contains an active agent such as a growth factor or antimicrobial agent. In the field or the clinic, the dressing can be readily dipped into the active agent subsequently applied to the wound.

A kit can comprise a notice regarding FDA approval and/or instructions for use.

Additionally, a kit designed for emergency or military use can also contain disposable pre-sterilized instruments, such as scissors, scalpel, clamp, tourniquet, elastic or inelastic bandages, or the like.

6. EXAMPLES

6.1 Example 1. Effects of Poly-N-Acetylglucosamine (pGlcNAc) Patch on Wound Healing in db/db Mouse

6.1.1 Materials and Methods

Preparation of pGlcNAc Patch.

The pGlcNAc patch SyvekPatch™ (Marine Polymer Technologies, Inc., Danvers, Mass.) consists of microalgal-derived nanofibers produced as previously described (see Vournakis et al. U.S. Pat. Nos. 5,623,064; and 5,624,679, the content of each of which is incorporated herein by reference in its entirety). Briefly, microalgae were cultured in unique bioreactor conditions using a defined growth media. Following the harvest of microalgae from high-density cultures, nanofibers were isolated via a stepwise separation and purification process resulting in batches of pure nanofibers suspended in water for injections (wfi). Fibers were formulated into patches by concentration and oven drying, and were packaged and sterilized by gamma-irradiation. Nanofiber dimensions average 20-50 nm×1-2 nm×~100 μm. Batches of fibers were individually quality controlled using chemical and physical test parameters, and each batch met strict purity criteria prior to release. Final batches were required to be substantially free of proteins, metal ions, and other components.

Wound Model and Study Design.

Homozygous, genetically diabetic 8-12 week-old, Lep/r—db/db male mice (strain C57BL/KsJ-Lepr$^{db}$) were used under an approved animal protocol in an Association for Assessment and Accreditation of Laboratory Animal Care International (AAALAC) accredited facility. The day before surgery, hair was clipped and depilated (Nair®, Church & Dwight Co., Princeton, N.J.). On the day of the surgery, animals were weighed and anesthetized with 60 mg/kg Nembutal (Pentobarbital). A dorsal 1.0 cm² area of skin and panniculus carnosus was excised and the wounds were photographed. Wounds were covered with the pGlcNAc patch for 1 hour (1 h group, n=15), 24 hrs (24 h group, n=15), or left untreated (NT group, n=15). All wounds were covered with semi-occlusive polyurethane dressings (Tegaderm®, 3M, St. Paul, Minn.). At day 10 and 21, 7-8 animals per group were euthanized and the wounds were photographed, excised, and fixed in 10% neutral-buffered formalin solution. N=15 per group were observed from day 1 to 10, and n=7-8 per group were observed from day 14 to day 21.

Wound Closure Analysis.

Three blinded independent observers compared digital photographs captured twice a week with initial photographs at day 0 using planimetric methods. Wound closure was quantified by measuring contraction (C), reepithelialization (E), and open wound (O) as a percentage of the original wound area. The sum of contracted, reepithelialized, and open wound areas equals 100% of the original wound size (FIG. 1) (see Yannas I. Tissue and Organ Regeneration in adults. New York: Springer; 2001).

Central wound cross-sections were embedded in paraffin, sectioned, and stained according to routine Hematoxylin and Eosin (H&E) protocols. Panoramic cross-sectional digital images of each wound were prepared using Adobe Photoshop CS Software (Adobe Systems Incorporated, San Jose, Calif.) in order to analyze granulation tissue area and thickness with digital planimetry (Image J, NIH, Bethesda, Md.).

Immunohistochemistry.

Paraffin-embedded sections were re-hydrated and antigen retrieval for the immuno-histochemical marker of proliferation Ki-67 was accomplished by microwaving in 10 mM sodium citrate (pH 6.0) for ten minutes. Frozen sections were fixed with acetone and stained for the immuno-histochemical marker of vascularization platelet endothelial cell adhesion molecule one (PECAM-1). Ki-67 (LabVision, Freemont, Ca) primary antibody was incubated for 1 hour at room temperature, while PECAM-1 (Pharmingen, San Jose, Calif.) primary antibody was incubated at 4° C. overnight. PECAM-1 signal was intensified using tyramide amplification system (Perkin Elmer, Boston, Mass.).

Vessel Density Quantification.

Digital color images of the wound sections were preprocessed before quantification to ensure uniform contrast of PECAM-1 positive areas relative to the background. A mask of positive staining was created using the color mask function of the program Corel PhotoPaint v.10 (Corel Corporation, Ottawa, Ontario, Canada) by sampling five different chromogen color tones represented in positively stained areas. The masked vessel areas were converted to pure black while the background was made pure white. The black and white representations were used for area quantification in IPLab software (BD Biosciences Bioimaging, Rockville, Md.) by applying the segmentation function. Tissue regions were defined by projecting the original H&E image over the processed image. Blood vessel density, quantified over the entire image, was expressed as the ratio of vessel area to total granulation tissue area. Between 4 and 7 microscopic fields (20×) were used to evaluate vessel density for each wound and treatment modality.

Quantification of Cell Proliferation.

Wounds were analyzed for cell proliferation using image analysis of Ki-67-stained sections in a manner similar to the method of vessel density quantification. High-power digital images of Ki-67 stained wound sections were used to measure the number of Ki-67 positive cells relative to the total number of nuclei. The degree of proliferation was quantified over the entire wound section using 4-6 fields at 20× magnification and expressed as a ratio of proliferating nuclei (Ki-67-positive) to total nuclei.

Statistical Analysis.

Values were expressed as means±standard deviation in the text and figures. One-way analysis of variance and ad hoc LSD tests were used to determine the significance of differences between treatment modes. Multivariate analysis was performed using Statistica v7.0 (StatSoft, Inc, Tulsa, Okla.).

6.1.2 Results

Statistical Analysis.

Values were expressed as means±standard deviation in the text and figures. One-way analysis of variance and ad hoc LSD tests were used to determine the significance of differences between treatment modes. Multivariate analysis was performed using Statistica v7.0 (StatSoft, Inc, Tulsa, Okla.).

pGlcNAc Patch Altered Wound Healing Kinetics. Treatment with pGlcNAc induced faster wound closure over time compared to non-treatment. The 1 h group showed faster ($p<0.01$) decrease of raw surface (open portion of the wound), compared to the NT group on day 7, 14 and 17 (FIG. 2A). The 1 h group also reached 90% closure on average in 16.6 days, which is nine days faster ($p<0.01$) than the NT group (25.6 days) (FIG. 2B). The 24 h group reached 90% closure in 18.2 days (FIG. 2B).

The 1 h group showed augmented ($p<0.01$) reepithelialization, compared to the NT group on day 4, 7, 14 and 21 (FIG. 2C, 2D). The 24 h group showed increased ($p<0.01$) reepithelialization, compared to the NT group on day 4 and 21 (FIG. 2C).

The 24 h group showed decreased ($p<0.01$) contraction, compared to the NT group on day 4 and 17; and decreased ($p<0.01$) contraction, compared to the 1 h group on day 7 (FIG. 2E). The 1 h group showed decreased ($p<0.01$) contraction, compared to the NT group on day 14 (FIG. 2E).

pGlcNAc Patch Increased Blood Vessel Density and Proliferation.

One $cm^2$, full-thickness, untreated wounds in db/db mouse reached 50% closure between 8-12 days post operation (Chan et al. Effect of recombinant platelet-derived growth factor (Regranex) on wound closure in genetically diabetic mice. *J Burn Care Res* 2006; 27(2):202-5). Day 10 was chosen as an intermediate time point for staging wound healing following the treatments.

Proliferating cells were stained for Ki-67 (FIG. 3A). PECAM-1 (CD31) was selected to stain endothelial cells and quantify the blood vessel density in granulation tissue (FIG. 3B). The 1 h group showed significant increases in blood vessel density and cell proliferation, compared to both the NT and 24 h groups (FIG. 3A, 3B). PECAM-1 and Ki-67 results were plotted together give visual correlation of angiogenesis and proliferation among different treatments (FIG. 3C).

Granulation tissue area and thickness were measured in microphotographs at 4× magnification (n=7-8 per group) to assess the level of coverage by the newly formed tissue in response to injury and treatment modality, as shown below:

|    | Granulation tissue area mean ± standard deviation (pixels) | Granulation tissue thickness mean ± standard deviation (pixels) |
|----|---|---|
| NT | $5.5 \times 10^5 \pm 5.3 \times 10^5$ | $3.5 \times 10^2 \pm 3.6 \times 10^2$ |
| 1 h | $1.1 \times 10^6 \pm 6.0 \times 10^5$ | $7.9 \times 10^2 \pm 3.9 \times 10^2$ |
| 24 h | $8.6 \times 10^5 \pm 2.7 \times 10^5$ | $5.7 \times 10^2 \pm 2.5 \times 10^2$ |

No significant differences were observed between the NT, 24 h and 1 h groups in the amount and distribution of granulation tissue.

Time of Application of pGlcNAc Patch Modulated Foreign Body Response.

To study the effects of an extended exposure of the wound bed to the insoluble fibers, the patch was initially left in place for the entire follow-up period (three weeks). The prolonged presence of the insoluble long fibers of the patch induced the formation of a foreign body response, characterized by increased granulation tissue formation and giant multinucleated cells. The application of the patch for 1 or 24 hours did not induce any foreign body reaction.

6.2 Example 2. Effects of Short Poly-N-Acetylglucosamine (sNAG) Membrane on Wound Healing in db/db Mouse

6.2.1 Materials and Methods

Preparation of sNAG Membrane.

The sNAG membrane consists of microalgal-derived nanofibers produced as described in Section 6.1 supra., in which the fibers are shortened by irradiation. Briefly, the starting material contained 60 g of pGlcNAc slurry at a concentration of 1 mg/mL. The concentration of the pGlcNAc slurry was confirmed by filtering 5 mL into a 0.2 um filter. 15 L of pGlcNAc slurry containing 15 g pGlcNAc was filtered until formation of a wet cake. The wake cake was then transferred into a foil pouch, which is a gamma radiation compatible container, and subjected to 200 kGy gamma radiation. Other irradiation conditions were tested for their effects on pGlcNAc compositions, as reflected in FIG. 4A.

Wound Model and Study Design.

The genetically mouse model described in Section 6.1 above was used to test the effect of sNAG membranes on wound healing.

Wound Closure Analysis.

Wound closure analysis was conducted substantially as described in Section 6.1. The sum of contracted, reepithelialized, and open wound areas equals 100% of the original wound size (FIG. 5) (see Yannas I. Tissue and Organ Regeneration in adults. New York: Springer; 2001).

Immunohistochemistry.

Immunochemistry was conducted substantially as described above in Section 6.1.

Vessel Density Quantification.

Vessel density quantification was performed substantially as described above in Section 6.1.

Quantification of Cell Proliferation.

Quantification of cell proliferation was performed substantially as described above in Section 6.1.

Collagen Staining.

Wounds were stained for collagen content using routine methods.

Statistical Analysis.

Statistical analysis of wound closure was performed substantially as described above in Section 6.1.

6.2.2 Results

Statistical Analysis.

Statistical analysis of wound closure was performed substantially as described above in Section 6.1.

Effect of Irradiation on pGlcNAc Membranes.

While irradiation reduces the molecular weight of pGlcNAc, irradiation did not disturb the microstructure of the fibers. pGlcNAc was irradiated under different conditions: as a dry, lyophilized material; as a dry membrane; as a concentrated slurry (30:70 weight by volume); and as a dilute slurry (5 mg/ml). A suitable molecular weight reduction (to a molecular weight of 500,000-1,000,000 daltons) was achieved at an irradiation dose of 1,000 kgy for thy polymer, and 200 kgy for wet polymer (FIG. 4A).

The chemical and physical structure of the fibers was maintained throughout irradiation as verified by infrared (IR) spectrum (FIG. 4B), elemental assay, and scanning electron microscopes (SEMs) analysis. Microscopic observation of irradiated fibers showed a decrease in the particle length (FIGS. 4C and 4D). The majority of the fibers are less than about 15 μm in length, with an average length of about 4 um.

sNAG Membrane Altered Wound Healing Kinetics.

Macroscopic photographs show that the wounds of sNAG membrane treated mice healed faster than the wounds of untreated control mice (see FIG. 6-10). Treatment with sNAG induced faster wound closure over time compared to non-treatment. The sNAG membrane treated mice showed faster ($p<0.05$) decrease of raw surface (open portion of the wound), compared to the untreated control mice on day 4, 7, 10, 14, 17, 21 and 25 (FIG. 11).

The sNAG membrane treated mice also reached 50% closure on average in a little over 8 days, which is four days faster ($p<0.01$) than the untreated control mice (over 12 days) (FIG. 12).

The sNAG membrane treated mice also reached 90% closure on average in less than 15 days, which is eight days faster ($p<0.01$) than the untreated control mice (approximately 23 days) (FIG. 13).

At day 28, all (100%) wounds closed in the sNAG membrane treated mice, whereas only 85% wounds closed in the untreated control mice.

The sNAG membrane treated mice showed augmented ($p<0.05$) reepithelialization, compared to the untreated control mice on day 14 and 17 (FIG. 14).

The sNAG membrane treated mice showed decreased ($p<0.01$) contraction, compared to the untreated control mice on day 4, 7 and 10 (FIG. 15).

sNAG Membrane Increased Blood Vessel Density and Proliferation.

One $cm^2$, full-thickness, untreated wounds in db/db mouse reached 50% closure between 8-12 days post operation (Chan et al. Effect of recombinant platelet-derived growth factor (Regranex) on wound closure in genetically diabetic mice. *J Burn Care Res* 2006; 27(2):202-5). Day 10 was chosen as an intermediate time point for staging wound healing following the treatments.

The histology of the wound edge in an untreated control mouse vs. in a sNAG membrane treated mouse is shown in FIGS. 16 and 17, respectively. Proliferating cells were stained for Ki-67 (FIG. 18). PECAM-1 (CD31) was selected to stain endothelial cells and quantify the blood vessel density in granulation tissue (FIG. 19). The sNAG membrane treated mice showed significant increases in blood vessel density and cell proliferation, compared to the untreated control mice (FIG. 16, 17).

Reepithelialization and granulation tissue area were measured in microphotographs at 4× magnification (n=7-8 per group) to assess the level of coverage by the newly formed tissue in response to injury and treatment modality, as shown in FIGS. 20 and 21.

Time of Application of sNAG Membrane Modulated Foreign Body Response.

To study the effects of an extended exposure of the wound bed to the sNAG fibers, sNAG the membrane was left in place during the entire experiment (four weeks). FIG. 22 shows the lack of foreign body reaction at 10 days. Moreover, no foreign body reaction was observed throughout the study in any of the sNAG membrane treated mice.

sNAG Membrane Modulated Collagen Formation/Arrangement.

Collagen staining was observed in both sNAG-treated and untreated mice, but collagen bundles were denser and more uniform in the treated mice, suggesting increased stimulation of wound fibroblasts and more advanced wound healing in the treated mice (FIG. 22).

6.3 Example 3. Effects of Poly-N-Acetylglucosamine (pGlcNAc) and sNAG on Endothelial Cell (EC) Movement and Angiogenesis

6.3.1 Materials and Methods

Tissue Culture, Growth Factors and Transfection.

Pooled, multiple-donor human umbilical cord vein endothelial cells (EC) (Cambrex) were maintained at 37° C. with 5% $CO_2$ in endothelial basal medium 2 (Cambrex) supplemented with EC growth medium 2 SingleQuots as described by Cambrex procedures. Serum starvation was performed at 80-90% confluency in RPMI-1640 supplemented with 0.1% fetal calf serum (Gibco BRL) for 24 h followed by stimulation with VEGF 165 (20 ng/ml, R&D Systems) or with highly purified pGlcNAc nanofibers or sNAG nanofibers in sterile water (provided by Marine Polymer Technologies, Inc., Danvers, Mass., USA) with the amounts indicated in the text. For inhibition using the VEGFR inhibitor SU5416 (10 µM; R&D Systems) cells were pretreated for 15 min prior to stimulation with VEGF, pGlcNAc or sNAG.

Human umbilical cord vein EC were transfected using the Amaxa nucleofector system in procedures described by the manufacturer, obtaining transfection efficiencies up to 80%. All transfections were monitored by expression of green fluorescent protein (GFP) using a GFP expression vector (pFP-C1; Clontech) or a GFP-directed RNA interference (RNAi; Amaxa). Plasmid-based RNAi directed specifically against Ets1 was purchased from Pandomics, Inc., and the dominant-negative Ets (dn-Ets) construct contains the DNA-binding domain of Ets2 cloned into a pcDNA3 expression vector.

Antibodies and Western Blot Analyses.

The antibodies used for Western blot analysis are as follows: anti-p85 subunit of PI3K (Upstate Biotechnology), anti-phosphospecific VEGFR2 (Cell Signaling), VEGFR2 (Santa Cruz), antiphospho-specific p42/p44 (Promega), and anti-phospho-specific VEGFR2 (BD Biosciences, Inc.), anti-p42/p44 Erk1/2, anti-VEGFR2 and anti-Ets1 (Santa Cruz).

Treated cells were washed once with phosphate-buffered saline (PBS) and lysed in 1×RIPA lysis buffer (50 mM Tris-HCl, pH 7.5, 1% Triton X-100, 150 mM NaCl, 0.1% SDS, 1% sodium deoxycholate, 40 mM NaF), supplemented with complete protease inhibitors without EDTA (Roche) and 200 µM sodium orthovanadate. Protein concentrations were determined by a bicinchoninic acid protein assay (Pierce) resolved by SDS-PAGE and transferred onto Immobilon-P polyvinylidene fluoride membranes (Millipore). Western analyses followed standard procedures. Proteins were visualized using Luminol reagent (Santa Cruz).

Cell Motility and Proliferation Assays.

For "scratch" wound closure assays, EC were grown to confluence on plastic tissue culture dishes and a single 'wound' was created using a pipette tip. Cells were then incubated in serum starvation media supplemented with or without VEGF (20 ng/ml), pGlcNAc, or sNAG at the amounts indicated in the text for 16-18 h. Cells were washed once with PBS, fixed for 10 min in methanol, stained with 0.1% crystal violet for 10 min and rinsed thoroughly with water. Wounding assays were photographed at 10× magnification using an Olympic light microscope equipped with digital imaging, and distance migrated was measured.

For modified transwell assays, transfected or untransfected EC were plated onto 8-µm pore size invasion chambers precoated with fibronectin or vitronectin at 20 µg/µl (Sigma), $5 \times 10^4$ cells per chamber in 500 µl of serum starvation media, and 500 µl of starvation media was added to the well. VEGF (20 ng/ml), pGlcNAc or sNAG was added to the upper chamber. Cells were incubated for 12 h at 37° C. in the presence of 5% $CO_2$. Cells that did not migrate were removed by wiping the top of each membrane with a cotton swab. The migrated cells were fixed in methanol for 10 min and stained with 0.1 µg/ml ethidium bromide in PBS. Migrated cells were counted using a Leica fluorescence microscope. Each assay was performed in triplicate at least 3 independent times, and at least 6 fields per transwell were counted.

For in vitro angiogenesis assays, EC were plated onto reduced growth factor Matrigel matrix (BD Laboratory) at $1.6 \times 10^4$ cells/50 µl per well of a 96-well plate in serum starvation media in the presence or absence of VEGF (20 ng/ml), pGlcNAc or sNAG. Cord formation was assessed for up to 8 h after plating. Cells were fixed and photographed when the VEGF-, pGlcNAc- and sNAG-treated cells began to form cords, while the controls retained a single cell layer. Assays were performed in duplicate and repeated 2 independent times.

For cellular proliferation/viability assessment, 2 different assays were used: trypan blue exclusion by direct cell counts using a hemacytometer and an MTT [3-(4,5-dimethylthiazol-2yl)-2,5-diphenyltetrazolium bromide] assay in procedures described by the manufacturer (Promega).

Antibody Blockade.

To block integrin-mediated cell motility and signaling, EC were preincubated for 15 min with blocking antibodies, at concentrations empirically determined (1 µg/ml), directed against $\alpha V \beta_3$ or $\alpha_5 \beta_1$ (CD49e) purchased from Chemicon International or against the α5 subunit (Santa Cruz) prior to stimulation with pGlcNAc or sNAG. Normal rabbit serum was used as a negative control. For inhibition of cell migration using the $\alpha V \beta_3$ antibody, transwells were pre-coated with vitronectin (Sigma) rather than with fibronectin (20 µg/µl). To block activation of VEGFR, EC were preincubated for 15 min with inhibitor, SU5416 (SU) at concentration of 10 µg/ml.

Reverse Transcription Polymerase Chain Reaction.

For semiquantitative reverse transcription polymerase chain reaction (RT-PCR), cDNA was synthesized from total RNA (2-5 µg), isolated using RNA-STAT 60 (Tel-Test, Inc.) in procedures described by the manufacturer, with a Superscript First-Strand Synthesis Kit purchased from Gibco BRL using oligo(dT) following the manufacturer's instructions. PCR reactions contained equal amounts of cDNA and 1.25 µM of the appropriate primer pair (Proligo, Inc.). The primer sequences are as follows: Ets1, forward 5'-TTCTCAGAGC-CCAGCTTCAT-3' (SEQ ID NO: 1), reverse 5'-AAAGTTT-GAATTCCCAGCCAT-3' (SEQ ID NO: 2); metallothionein 2A, forward 5'-CAACCTGTCCCGACTCTAGC-3' (SEQ ID NO: 3), reverse 5'-AGGAGCAACTCCTGTCCTGA-3' (SEQ ID NO: 4); S26, forward 5'-CTCCGGTCCGTGC-CTCCAAG-3' (SEQ ID NO: 5), reverse 5'-CAGA-GAATAGCCTGTCTTCAG-3' (SEQ ID NO: 6); VEGF, forward 5'-CTACCTCCACCATGCCAAGT-3' (SEQ ID NO: 7), reverse 5'-TGGTGATGTTGGCTCCTCA-3' (SEQ ID NO: 8); IL-1, forward 5'-CTGCGCCAACACA-GAAATTA-3' (SEQ ID NO: 9), reverse 5'-ATTGCATCTG-GCAACCCTAC-3' (SEQ ID NO: 10); IL-8, forward 5'-TCGGATTTCACGATTTCTCC-3' (SEQ ID NO: 11), reverse 5'-GCTACAAGTGCGTCGTCAAA-3' (SEQ ID NO: 12). Cycling conditions were: 94° C. for 5 min; 20-35 cycles of 94° C. for 1 min, 50-65° C. (based on primer T m) for 1 min, 72° C. for 1 min and 45 s+2 s/cycle; 72° C. for 7 min and cooled to 4° C. The cycle number was empirically determined to be within the linear range of the assay for each primer pair used. All semiquantitative RTPCRs were performed in tandem with S26 primers as an internal control. Products were run on 1-1.5% agarose gels (based on product size) and visualized on a BioRad Molecular Imaging System.

Real-time PCR was performed using a Brilliant CYBR green quantitative PCR (QPCR) kit in combination with an M×3000P real-time PCR system, both purchased from Stratagene. Real time was performed at least in triplicate at least 2 independent times. Internal control primers that detect the ribosomal protein subunit S26 were used.

6.3.2 Results

6.3.2.1 pGlcNAc pGlcNAc Protected EC from Cell Death Induced by Serum Starvation.

To test if pGlcNAc fibers had a direct effect on EC, serum-starved EC cells were treated with VEGF or with different concentrations of pGlcNAc fibers. As shown in FIG. 24 at 48 h and 72 h after serum starvation, as compared with the total number of cells plated (control), there was about 2-fold reduction in the number of cells after 48 h or 72 h. At 48 h, this decrease in cell number was rescued by the addition of VEGF or by the addition of pGlcNAc fibers at either 50 or 100 µg/ml. At 72 h, the decrease in cell number was rescued by the addition of VEGF or largely rescued by the addition of pGlcNAc fibers at 100 µg/ml. These results indicated that like VEGF, pGlcNAc fiber treatment prevented cell death induced by serum deprivation.

pGlcNAc Did not Effect Metabolic Rate.

As shown in FIG. 25, pGlcNAc did not result in a higher metabolic rate as measured by MTT assays, indicating that this polymeric material was not causing marked increases in cellular proliferation but was rescuing cell death by serum deprivation.

pGlcNAc Increased Cell Migration.

To test whether pGlcNAc fiber treatment of EC resulted in changes in cell motility, the "scratch" wound closure assay was used. Migration of the cells into the wounded area was significantly increased in the presence of pGlcNAc at both 50, 100 and 250 µg/ml. As shown in FIG. 26, wound closure was similar to that observed for VEGF treatment. These results indicated that pGlcNAc treatment resulted in an increase in EC movement.

pGlcNAc Caused an Increase in Migration Towards Fibronectin.

To determine whether this increased cell motility correlated with an increased cellular invasion, EC motility was measured using transwell assays where membranes were precoated with the extracellular matrix protein, fibronectin. As shown in FIG. 27, pGlcNAc treatment resulted in a 3-fold increase in migration toward fibronectin that was enhanced by the addition of VEGF (4-fold).

pGlcNAc Increased Cord Formation.

Stimulation of cell migration is a prerequisite for increased angiogenesis. To test, in vitro, whether pGlcNAc was proangiogenic, Matrigel assays were performed. EC were plated on growth factor-reduced Matrigel under conditions of serum starvation and assessed for cord formation in the presence or absence of VEGF or pGlcNAc fibers within 6 h. As shown in FIG. 28, both VEGF and pGlcNAc treatment resulted in increased cord formation on Matrigel. These results indicate that pGlcNAc is proangiogenic.

pGlcNAc Induced Effectors Involved in Cell Motility.

Total RNA was isolated from serum-starved EC (SS); SS treated with VEGF, pGlcNAc, Sphingosiing 1-phosphate (SIP), or Zn; SS pre-treated with VEGF or SIP then following pGlcNAc treatment; SS pre-treated with VEGF or pGlcNAc then following the treatment of VEGFR inhibitor, SU5416 (Su). As shown in FIG. 29A, pGlcNAc treatment stimulated the expression of the Ets1 transcription factor, which is an important regulator of EC movement, and metallothionein 2A (MT), Akt3 and Edg3. As shown in FIG. 29B, real-time PCR indicates that Ets1 was induced approximately 2-fold by pGlcNAc treatment. This Ets1 increase in message was accompanied by a higher protein expression as shown in the Western blot analysis in FIG. 29C. FIG. 29A also indicated that MT expression stimulated by pGlcNAc was VEGFR dependent.

pGlcNAc's Induction of Phospho-MAPK was VEGFR2-Dependent.

To test whether pGlcNAc treatment resulted in the activation of pathways previously shown downstream of VEGFR signaling, EC were treated with VEGF or pGlc-NAc. As shown in FIG. 30A, pGlcNAc treatment resulted in a marked increase in the phosphorylation of MAPK. To test whether this increase was VEGFR2 dependent, EC were pretreated by VEGFR inhibitor, following VEGF or pGlc-NAc treatment. The results indicated that pGlcNAc's induction of phosphor-MAPK was dependent on VEGFR2 (see also FIG. 30B).

pGlcNAc did not activate VEGFR2.

To test whether pGlcNAc activated the VEGFR, a series of Western blots were performed using an antibody directed against the phosphorylated form of VEGFR2. As shown in FIG. 31, VEGF treatment caused a rapid phosphorylation of VEGFR, accompanied by turnover of total VEGFR2 protein levels, whereas pGlcNAc had no effect either at these early time points shown, or up to 6 h after treatment (data not shown).

pGlcNAc-Induced Migration was Ets Dependent.

To test whether Ets1 was required for the motility induced by pGlcNAc, Ets1 was inhibited using both a dominant-negative approach as well as by RNAi. A dn-Ets construct expressing the conserved Ets DNA binding domain was transfected into EC. After 24 h to allow for expression of the dn-Ets, the cells were assessed for changes in cell migration toward fibronectin in transwell assays after treatment with pGlcNAc. As shown in FIG. 32A, inhibition of Ets1 activity as well as of other family members expressed in EC resulted in a marked decrease in EC migration in response to pGlcNAc. As a control for the activity of the dn-Ets, FIG. 5B shows that transfection of increasing amounts of dn-Ets results in a decreased total Ets1 protein. Ets1 expression can be controlled not only by another family member, but can also be autoregulated. Inhibition of Ets1 specifically by RNAi also resulted in a decrease in cell motility induced by pGlcNAc on fibronectin (FIG. 32A, right side). As shown in FIG. 32B, in cells transfected with dn-Ets expression plasmid, the Ets1 protein expression decreased with the amount of plasmid increasing. As a control for the RNAi experiment, FIG. 32C shows the resultant expression levels of Ets1 in EC transfected with 2 amounts of plasmid-containing RNAi directed against Ets1. Expression of dn-Ets resulted in a more substantial reduction in cell migration than the Ets1 RNAi, probably due to its blockade of other family members expressed in EC. This findings supported a role for Ets1 in the induction of cell motility by pGlcNAc.

pGlcNAc-Induced Cell Motility Required Integrin.

To test whether the effects of pGlcNAc are integrin dependent, blocking antibodies were used to disrupt integrin-mediated signaling in EC. The effect of these antibodies on pGlcNAc-induced cell migration was assessed using transwell assays. FIG. 33A shows the results when using antibodies directed against $\alpha V\beta_3$ or $\alpha_5\beta_1$ (CD49e) integrin in migration assays toward fibronectin (the $\alpha V\beta_3$ receptor). FIG. 33B shows a similar experiment using antibodies directed against $\alpha V\beta_3$ or $\alpha_5\beta_1$ (CD49e) in transwells coated with vitronectin. Antibody blockade of either integrin subtype resulted in inhibition of pGlcNAc-induced cell motility on their cognate substrates. These results indicate that pGlcNAc stimulates cell motility via integrin activation. The results are also consistent with pGlcNAc stimulating angiogenesis via integrin activation.

pGlcNAc-Induced Cell Motility May Involve the Activation of FAK Via Integrin Engagement.

FAK becomes phosphorylated in response to integrin clustering and activation. FAK is a key regulator of integrin and growth factor-mediated cell motility and invasion. To test integrin activation by pGlcNAc, EC were treated with pGlcNAc fibers for increasing amounts of time and assayed for changes in the level of FAK phosphorylation. As shown in FIG. 34, pGlcNAc treatment resulted in the phosphorylation of FAK within 15 min of treatment. These results indicate that pGlcNAc-induced cell motility may involve the activation of FAK via integrin engagement.

pGlcNAc Activates an Integrin→Ets1 Pathway Leading to Angiogenesis in a Wound-Healing Model.

A role for Ets1 in the transcriptional regulation of a number of integrin subunits has been described, positioning Ets1 upstream of integrins. The finding that motility induced by pGlcNAc is dependent both on integrins and Ets1 implies that Ets1 may be regulated downstream of integrins. To confirm that integrin activation results in the regulation of Ets1 expression, blocking antibodies directed against $\alpha s\beta_1$ (the fibronectin receptor) or $\alpha V\beta_3$ (the vitronectin receptor) were used to inhibit integrins by pGlcNAc. FIG. 35A shows that antibody blockade of $\alpha_5\beta_1$ integrin results in a reduction in pGlcNAc-induced Ets1 expression. This inhibition of Ets1 expression using a blockade of $\alpha_5\beta_1$ integrin is recapitulated on the protein level (FIG. 35B). However, although the $\alpha V\beta_3$ integrin antibody blocked motility on vitronectin, it did not affect the pGlcNAc-induced expression of Ets1 (FIG. 35), indicating that pGlcNAc-induced cell motility on vitronectin may be Ets1 independent. Taken together, these results position Ets1 downstream of certain integrins in primary EC and indicate potential specificity in integrin signaling with respect to Ets1 expression in primary EC. These findings, therefore indicate that pGlcNAc can activate an integrin→Ets1 pathway leading to angiogenesis in a wound-healing model.

pGlcNAc Induced Expression of VEGF and IL1.

To test whether pGlcNAc treatment induced the expression of growth factors or cytokines known to be secreted by activated EC, serum-starved EC were treated with pGlcNAc for 12 h and assessed for changes in expression of VEGF, IL-1 and IL-8. As shown by RT-PCR and QPCR (FIG. 36A), pGlcNAc treatment resulted in an increased expression of both VEGF and IL-1. These findings also indicated that the response of the EC to pGlcNAc is specific since there was no change in expression of another interleukin, IL-8. To test the pGlcNAc-dependent induction of Ets1 expression, a transcription factor known to be regulated by VEGF, secondary to the pGlcNAc effect on VEGF expression, activation of VEGFR was blocked using the pharmacological inhibitor, SU5416 (SU), prior to treatment with pGlcNAc. As shown by QPCR (FIG. 36B), treatment of EC with this inhibitor blocked the induction of Ets1 by VEGF but had no effect on the induction of Ets1 by pGlcNAc.

pGlcNAc Induced Expression of FGF1 and FGFR3.

To test whether pGlcNAc treatment induced the expression of angiogenesis-related factors, EC were treated with pGlcNAc and assessed for changes in expression of FGF1, FGF2, FGFR1, FGFR2, FGFR3, Stabilin, IFNg, CollagenA18. As shown by FIG. 37, pGlcNAc treatment resulted in an increased expression of Stabilin and CollagenA18.

6.3.2.2 sNAG sNAG Increased Cell Migration.

To test whether sNAG fiber treatment of EC resulted in changes in cell motility, the "scratch" wound closure assay was used. Migration of the cells into the wounded area was significantly increased in the presence of sNAG at both 50 and 100 µg/ml. Wound closure was similar to that observed for pGlcNAc treatment (see FIG. 38). These results indicated that sNAG treatment resulted in an increase in EC movement.

sNAG Induced Marked Increase in Metabolic Rate.

As measured by MTT assays, sNAG at 50, 100 or 200 µg/ml resulted in a higher metabolic rate of EC than VEGF (FIG. 39).

sNAG Did not Protect EC from Cell Death Induced by Serum Deprivation.

To test if sNAG fibers had a direct effect on EC, serum-starved EC cells were treated with VEGF or with different concentrations of sNAG fibers. As shown in FIG. 40, at 48 h after serum starvation, as compared with the total number of cells plated (control), there was about 2-fold reduction in the number of cells. This decrease in cell number was rescued by the addition of VEGF but not by the addition of sNAG fibers at 50, 100 or 200 µg/ml. These results indicated that not like VEGF, sNAG fiber treatment did not prevent cell death induced by serum deprivation.

sNAG Induced Expression of VEGF and IL1.

To test whether sNAG treatment induced the expression of growth factors or cytokines known to be secreted by activated EC and compare the effect with pGlcNAc, serum-starved EC were treated with pGlcNAc or sNAG for 12 h and assessed for changes in expression of VEGF, IL-1 and IL-8. As shown by FIG. 41, sNAG treatment resulted in an increased expression of both VEGF and IL-1. These findings also indicated that the response of the EC to sNAG is specific since there was no change in expression of another interleukin, IL-8.

sNAG Induced Expression of FGF1 and FGFR3.

To test whether sNAG treatment induced the expression of angiogenesis-related factors, EC were treated with sNAG and assessed for changes in expression of FGF1, FGF2, FGFR1, FGFR2, FGFR3, Stabilin, IFNg, CollagenA18. As shown by RT-PCR (FIG. 37), sNAG treatment resulted in an increased expression of FGF1 and FGFR3.

The above results demonstrate that both pGlcNAc and sNAG induced EC motility, and that both pGlcNAc and sNAG induce the expression of VEGF and IL-1.

The above results also demonstrate that sNAG increases the metabolic rate of serum-starved EC in a MTT assay and does not rescue apoptosis of serum-starved EC in a trypan blue exclusion test.

6.4 Example 4. Preclinical Testing of sNAG

6.4.1 Test Article

A test article comprising sNAG produced as previously described in Section 6.2.1 supra. was utilized. The test article was supplied sterile by Marine Polymer Technologies, Inc.

6.4.2 Biocompatibility Testing—L929 MEM Elusion Test—ISO 10993-5

Biocompatibility of the test article was tested in mouse fibroblast L929 mammalian cells. No biological reactivity (Grade 0) was observed in the L929 cells at 48 hours, post exposure to the test article. The observed cellular response obtained from the positive control article (Grade 4) and negative control article (Grade 0) confirmed the suitability of the test system. Based on the criteria of the protocol, the test article is considered non-toxic and meets the requirements of the Elution Test, International Organization for Standardization (ISO) 10993-5 guidelines. See Table I below.

TABLE I

REACTIVITY GRADES

| | Test Article | | | Controls | | | | | | | | |
| --- | --- | --- | --- | --- | --- | --- | --- | --- | --- | --- | --- | --- |
| | | | | Medium | | | Negative | | | Positive | | |
| Time | A | B | C | A | B | C | A | B | C | A | B | C |
| 0 Hours | 0 | 0 | 0 | 0 | 0 | 0 | 0 | 0 | 0 | 0 | 0 | 0 |
| 24 Hours | 0 | 0 | 0 | 0 | 0 | 0 | 0 | 0 | 0 | 3 | 3 | 3 |
| 48 Hours | 0 | 0 | 0 | 0 | 0 | 0 | 0 | 0 | 0 | 4 | 4 | 4 |

| Grade | Reactivity | Description of Reactivity Zone |
| --- | --- | --- |
| 0 | None | Discrete intracytoplasmic granules; no cell lysis |
| 1 | Slight | Not more than 20% of the cells are round, loosely attached, and without intracytoplasmic granules; occasional lysed cells are present |
| 2 | Mild | Not more than 50% of the cells are round and devoid of intracytoplasmic granules; no extensive cell lysis and empty areas between cells |
| 3 | Moderate | Not more than 70% of the cell layers contain rounded cells or are lysed |
| 4 | Severe | Nearly complete destruction of the cell layers |

6.4.3 Intramuscular Implantation Test—ISO—4 Week Implantation

6.4.2.1 Materials and Methods

To evaluate the potential of the test article to induce local toxic effects, the Intramuscular Implantation Test—ISO—4 Week Implantation ("Intramuscular Implantation Test") was used. Briefly, the test article was implanted in the paravertebral muscle tissue of New Zealand White rabbits for a period of 4 weeks. The test article was then evaluated separately using two control articles: positive control Surgicel (Johnson and Johnson, NJ) and negative control High Density Polyethylene (Negative Control Plastic).

Preparation of Test and Control Articles.

The test article measured approximately 1 mm to in width and 10 mm in length. The two control articles were prepared. The positive control, Surgicel (C1), measured approximately 1 mm in width by 10 mm in length and was received sterile. Negative Control Plastic (C2), measured approximately 1 mm in width by 10 mm in length and was sterilized by dipping in 70% ethanol.

Pre-Dose Procedure.

Each animal was weighed prior to implantation. On the day of the test, the dorsal sides of the animals were clipped free of fur and loose hair was removed by means of a vacuum. Each animal was appropriately anesthetized. Prior to implantation, the area was swabbed with a surgical preparation solution.

Dose Administration.

Four test article strips were surgically implanted into each of the paravertebral muscles of each rabbit, approximately 2.5 cm from the midline and parallel to the spinal column and approximately 2.5 cm from each other. The test article strips were implanted on one side of the spine. In a similar fashion, positive control article strips (Surgicel) were implanted in the contralateral muscle of each animal. Two negative control strips (Negative Control Plastic) were implanted caudal (toward the tail) to the test article and to C1 control implant sites on either side of the spine (total of four strips). A total of at least eight test article strips and eight of each control article strips are required for evaluation.

Post-Dose Procedures.

The animals were maintained for a period of 4 weeks. The animals were observed daily for this period to ensure proper healing of the implant sites and for clinical signs of toxicity. Observations included all clinical manifestations. At the end of the observation period, the animals were weighed. Each animal was sacrificed by an injectable barbiturate. Sufficient time was allowed to elapse for the tissue to be cut without bleeding.

Gross Observations.

The paravertebral muscles in which the test or control articles were implanted were excised in toto from each animal. The muscle tissue was removed by carefully slicing around the implant sites with a scalpel and lifting out the tissue. The excised implant tissues were examined grossly, but without using excessive invasive procedures that might have disrupted the integrity of this tissue for histopathological evaluation. The tissues were placed in properly labeled containers containing 10% neutral buffered formalin.

Histopathology.

Following fixation in formalin, each of the implant sites was excised from the larger mass of tissue. The implant site, containing the implanted material, was examined macroscopically. Each site was examined for signs of inflammation, encapsulation, hemorrhaging, necrosis, and discoloration using the following scale:
0=Normal
1=Mild
2=Moderate
3=Marked After macroscopic observation, the implant material was left in-situ and a slice of tissue containing the implant site was processed. Histologic slides of hematoxylin and eosin stained sections were prepared by Toxikon. The slides were evaluated and graded by light microscopic examination.

Pathological Assessment of the Effects of the Implant.

The following categories of biological reaction were assessed by microscopic observation for each implant site:
1. Inflammatory Responses:
   a. Polymorphonuclear leukocytes
   b. Lymphocytes
   c. Eosinophils
   d. Plasma cells
   e. Macrophages
   f. Giant cells
   g. Necrosis
   h. Degeneration
2. Healing Responses:
   a. Fibrosis
   b. Fatty Infiltrate Each category of response was graded using the following scale:
0=Normal
0.5=Very Slight
1=Mild
2=Moderate
3=Marked The relative size of the involved area was scored by assessing the width of the area from the implant/tissue interface to unaffected areas which have the characteristics of normal tissue and normal vascularity. Relative size of the involved area was scored using the following scale:
0=0 mm, No site
0.5=up to 0.5 mm, Very slight
1=0.6-1.0 mm, Mild
2=1.1-2.0 mm, Moderate
3=>2.0 mm, Marked The Intramuscular Implantation Test was conducted based upon the following references:
1. ISO 10993-6, 1994, Biological Evaluation of Medical Devices—Part 6: Tests for Local Effects After Implantation.
2. ISO 10993-12, 2002, Biological Evaluation of Medical Devices—Part 12: Sample Preparation and Reference Materials.
3. ASTM F981-04, 2004, Standard Practice for Assessment of Compatibility of Biomaterials for Surgical Implants with Respect to Effect of Materials on Muscle and Bone.
4. ASTM F763-04, 2004, Standard Practice for Short Term Screening of Implant Materials.
5. ISO/IEC 17025, 2005, General Requirements for the Competence of Testing and Calibration Laboratories.

The results of the Intramuscular Implantation Test were evaluated based upon the following criteria:
1. Calculated Rating: For each implanted site, a total score is determined. The average score of the test sites for each animal is compared to the average score of the control sites for that animal. The average difference between test and control sites for all animals is calculated and the initial Bioreactivity Rating is assigned as follows:
0-1.5 No Reaction*
>1.5-3.5 Mild Reaction
>3.5-6.0 Moderate Reaction
>6.0 Marked Reaction
* A negative calculation is reported as zero (0).
2. Modification of the Rating: The pathology observer reviews the calculated level of bioreactivity. Based on the observation of all factors (e.g., relative size, pattern of response, inflammatory vs. resolution), the pathology observer may revise the Bioreactivity Rating. Justification for the modification to the rating is presented in the narrative report (A descriptive narrative report regarding the biocompatibility of the test material is provided by the pathology observer).

6.4.2.2 Results

The results indicated that the test article was non-reactive when implanted for 4 weeks (Bioreactivity Rating of 0.2) when compared to positive control Surgicel; and non-reactive (Bioreactivity Rating of 0.0) when compared to negative control High Density Polyethylene (Negative Control Plastic).

Clinical Observation.

Table II below shows results of the macroscopic evaluation of the test article and control implant sites indicated no significant signs of inflammation, encapsulation, hemorrhage, necrosis, or discoloration at the 4 week time period. Some test sites and the majority of the positive control, Surgicel, were not seen macroscopically and serial sections were submitted for microscopic evaluation.

TABLE II

Macroscopic Observations
4 Week Implantation
Test Article: MP719
Lot/Batch No.: Not Supplied by Sponsor Animal No.: 60959

| Tissue Site: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | 0 | NSF | 0 | NSF | 0 | NSF | NSF | NSF | NSF | N/A | 0 | 0 | 0 | 0 | 0 |
| Encapsulation | 0 | NSF | 0 | NSF | 0 | NSF | NSF | NSF | NSF | N/A | 0 | 0 | 0 | 0 | 0 |
| Hemorrhage | 0 | NSF | 0 | NSF | 0 | NSF | NSF | NSF | NSF | N/A | 0 | 0 | 0 | 0 | 0 |
| Necrosis | 0 | NSF | 0 | NSF | 0 | NSF | NSF | NSF | NSF | N/A | 0 | 0 | 0 | 0 | 0 |
| Discoloration | 0 | NSF | 0 | NSF | 0 | NSF | NSF | NSF | NSF | N/A | 0 | 0 | 0 | 0 | 0 |
| Total | 0 | N/A | 0 | N/A | | N/A | N/A | N/A | N/A | | 0 | 0 | 0 | 0 | |

TABLE II-continued

Macroscopic Observations
4 Week Implantation
Test Article: MP719
Lot/Batch No.: Not Supplied by Sponsor Animal No.: 60961

| Tissue Site: | T1 | T2 | T3 | T4 | Test Ave. | C2-1 | C1-2 | C2-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | NSF | NSF | NSF | NSF | N/A | NSF | NSF | NSF | NSF | N/A | 0 | 0 | NSF | 0 | 0 |
| Encapsulation | NSF | NSF | NSF | NSF | N/A | NSF | NSF | NSF | NSF | N/A | 0 | 0 | NSF | 0 | 0 |
| Hemorrhage | NSF | NSF | NSF | NSF | N/A | NSF | NSF | NSF | NSF | N/A | 0 | 0 | NSF | 0 | 0 |
| Necrosis | NSF | NSF | NSF | NSF | N/A | NSF | NSF | NSF | NSF | N/A | 0 | 0 | NSF | 0 | 0 |
| Discoloration | NSF | NSF | NSF | NSF | N/A | NSF | NSF | NSF | NSF | N/A | 0 | 0 | NSF | 0 | 0 |
| Total | N/A | N/A | N/A | N/A | | N/A | N/A | N/A | N/A | | 0 | 0 | N/A | 0 | |

Animal No.: 60968

| Tissue Site: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | NSF | NSF | NSF | NSF | N/A | NSF | NSF | NSF | NSF | N/A | 0 | 0 | 0 | 0 | 0 |
| Encapsulation | NSF | NSF | NSF | NSF | N/A | NSF | NSF | NSF | NSF | N/A | 0 | 0 | 0 | 0 | 0 |
| Hemorrhage | NSF | NSF | NSF | NSF | N/A | NSF | NSF | NSF | NSF | N/A | 0 | 0 | 0 | 0 | 0 |
| Necrosis | NSF | NSF | NSF | NSF | N/A | NSF | NSF | NSF | NSF | N/A | 0 | 0 | 0 | 0 | 0 |
| Discoloration | NSF | NSF | NSF | NSF | N/A | NSF | NSF | NSF | NSF | N/A | 0 | 0 | 0 | 0 | 0 |
| Total | N/A | N/A | N/A | N/A | | N/A | N/A | N/A | N/A | | 0 | 0 | 0 | 0 | |

T = test site (representative sections were submitted for microscopic assessment)
C1 = Surgicel (Due to the nature of the material, representative sections were submitted for microscopic assessment)
C2 = Negative Control High Density Polyethylene (Negative Control Plastic)
Grading Scale
0 = no reaction
1 = mild reaction
2 = moderate reaction
3 = marked reaction
NSF = No Site Found
N/A = Not Applicable Implantation Site Observations (Microscopic).

Table III below shows results of the microscopic evaluation of the test article implant sites indicated no significant signs of inflammation, fibrosis, hemorrhage, necrosis, or degeneration as compared to each of the control article sites. The Bioreactivity Rating for the 4 week time period (average of three animals) was 0.2, (C1—Surgicel) and 0.0 (C2—Negative Control Plastic) indicating no reaction as compared to either of the control implant sites. The pathologist noted there was a moderate polymorphic and histiocytic (macrophages) infiltrate around the in situ test article that was not unexpected given the nature of the test material.

TABLE III

Microscopic Observations
4 Week Implantation

Animal No.: 60959

| | Categories | | | | | | | | | | |
|---|---|---|---|---|---|---|---|---|---|---|---|
| | Test Sites** | | | Control Sites | | | | | | | |
| Reaction | T1 | T2 | T3 | C1-1 | C1-2 | C1-3 | C1-4 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.5 | 0.0 | 0.0 | 0.0 | 0.0 | 0.0 | 0.0 | 0.0 | 0.0 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.0 | 0.5 | 0.0 | 0.0 | 0.0 | 0.0 | 0.0 |
| * Necrosis | 0.0 | 0.0 | 0.0 | 0.0 | 0.0 | 0.0 | 0.0 | 0.0 | 0.0 | 0.0 | 0.0 |

TABLE III-continued

|  | Microscopic Observations 4 Week Implantation | | | | | | | | | | |
|---|---|---|---|---|---|---|---|---|---|---|---|
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.0 | 0.0 | 0.5 | 0.0 | 0.5 | 0.0 | 0.5 | 0.5 | 0.5 | 0.0 | 0.5 |
| Total | 1.5 | 2.0 | 2.5 | 1.5 | 1.5 | 1.5 | 1.5 | 1.5 | 1.5 | 1.0 | 1.5 |

T = Test Site
C1 = Surgicel
C2 = Negative Control High Density Polyethylene (Negative Control Plastic)
Animal Test Score (Average*) = 2.0
Animal C1 Score (Average*) = 1.5
Animal C2 Score (Average*) = 1.4
Animal Score (Average Test Score − Average C1 Score) = 0.5
Animal Score (Average Test Score − Average C2 Score) = 0.6
*Used in calculation of Bioreactivity Rating.
**No site found in T4.

Animal No.: 60961

|  | Categories | | | | | | | | |
|---|---|---|---|---|---|---|---|---|---|
|  | Test Sites** | | | Control Sites** | | | | | |
| Reaction | T1 | T3 | T4 | C1-1 | C1-3 | C1-4 | C2-1 | C2-2 | C2-3 |
| Foreign Debris | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 |
| * Polymorphs | 0.0 | 0.0 | 0.5 | 0.5 | 0.0 | 0.5 | 0.5 | 0.5 | 0.5 |
| * Lymphocytes | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 |
| * Fatty Infiltrate | 0.0 | 0.5 | 0.0 | 0.5 | 0.0 | 0.5 | 0.5 | 0.5 | 0.5 |
| Total | 1.5 | 2.0 | 2.0 | 2.5 | 1.5 | 2.5 | 2.5 | 2.5 | 2.5 |

T = Test Site
C1 = Surgicel
C2 = Negative Control High Density Polyethylene (Negative Control Plastic)
Animal Test Score (Average*) = 1.8
Animal C1 Score (Average*) = 2.2
Animal C2 Score (Average*) = 2.5
Animal Score (Average Test Score − Average C1 Score) = −0.4
Animal Score (Average Test Score − Average C2 Score) = −0.7
*Used in calculation of Bioreactivity Rating.
**No site found in T2, C1-2, and C2-4.

Animal No.: 60968

|  | Categories | | | | | | | | | | |
|---|---|---|---|---|---|---|---|---|---|---|---|
|  | Test Sites | | | | Control Sites** | | | | | | |
| Reaction | T1 | T2 | T3 | T4 | C1-1 | C1-2 | C1-3 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.0 | 0.5 | 0.0 | 0.0 | 0.5 | 0.5 | 0.0 | 0.0 | 0.5 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 | 0.0 | 0.0 |

TABLE III-continued

| | Microscopic Observations 4 Week Implantation | | | | | | | | | | |
|---|---|---|---|---|---|---|---|---|---|---|---|
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.5 | 0.5 | 0.5 | 0.5 | 0.5 | 0.0 | 0.0 | 0.5 | 0.5 | 0.5 | 0.5 |
| Total | 2.0 | 2.5 | 2.0 | 2.5 | 2.0 | 1.5 | 2.0 | 2.5 | 2.5 | 2.0 | 2.5 |

T = Test Site
C1 = Surgicel
C2 = Negative Control High Density Polyethylene (Negative Control Plastic)
Animal Test Score (Average*) = 2.3
Animal C1 Score (Average*) = 1.8
Animal C2 Score (Average*) = 2.4
Animal Score (Average Test Score − Average C1 Score) = 0.5
Animal Score (Average Test Score − Average C2 Score) = −0.1
*Used in calculation of Bioreactivity Rating.
**No site found in C1-4.

| | C1 | C2 |
|---|---|---|
| Animal Score 60759 = | 0.5 | 0.5 |
| Animal Score 60961 = | −0.4 | −0.7 |
| Animal Score 60968 = | 0.5 | −0.1 |

Bioreactivity Rating = 0.2 = No Reation
Bioreactivity Rating = −0.1 = No Reaction

6.4.4 Intracutaneous Injection Test—ISO 10993-10

USP 0.9% Sodium Chloride for Injection (NaCl) and Cottonseed Oil (CSO) extracts of the test article were evaluated for their potential to produce irritation after intracutaneous injection in New Zealand White rabbits. The test article sites did not show a significantly greater biological reaction than the sites injected with the control article. Based on the criteria of the protocol, the test article is considered a negligible irritant and meets the requirements of the ISO 10993-10 guidelines. Results are shown below in Table IV.

6.4.5 Kligman Maximization Test—ISO 10993-10

UPS 0.9% Sodium Chloride for Injection (NaCl) and Cottonseed Oil (CSO) extracts of the test article elicited no intradermal reaction in Hartley guinea pigs at the challenge (0% sensitization), following an induction phase. Therefore, as defined by the scoring system of Kligman, this is a Grade I reaction and the test article is classified as having weak allergenic potential. Based on the criteria of the protocol, a Grade I sensitization rate is not considered significant and

TABLE IV

Intracutaneous Test Skin Reaction Scores

| | | | Site Numbers Scoring (ER/ED) | | | | | | | | | |
|---|---|---|---|---|---|---|---|---|---|---|---|---|
| Animal # | Vehicle | Time | T-1 | T-2 | T-3 | T-4 | T-5 | C-1 | C-2 | C-3 | C-4 | C-5 |
| NaCl Extract | | | | | | | | | | | | |
| 61917 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| 61919 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | Total | | | | 0.0 | | | | | 0.0 | | |
| CSO Extract | | | | | | | | | | | | |
| 61917 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| 61919 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | Total | | | | 0.0 | | | | | 0.0 | | |

†= Immediately after injection, not used for the evaluation criteria.
Overall Mean Score* for Test Article = 0.0
Overall Mean Score* for Control Article = 0.0
Difference between Test Article and Control Article Overall Mean Score = 0.0 − 0.0 = 0.0
ER = Erythema;
ED = Edema;
T = Test Sites;
C = Control Sites
*Overall Mean Score = Total erythema plus edema scores divided by 12 (2 animals × 3 scoring periods × 2 scoring categories)

the test article meets the requirements of the ISO 10993-10 guidelines. Results are shown below in Table V.

TABLE V

Skin Examination Data

| Group | Animal # | Sex | Scores Day 25 | Scores Day 26 | Scores Day 27 | Percent Animals Sensitized | Allergenic Potential |
|---|---|---|---|---|---|---|---|
| Test Article (NaCl Extract) | 1 | Male | 0 | 0 | 0 | 0% | Weak |
| | 2 | Male | 0 | 0 | 0 | | |
| | 3 | Male | 0 | 0 | 0 | | |
| | 4 | Male | 0 | 0 | 0 | | |
| | 5 | Male | 0 | 0 | 0 | | |
| | 6 | Female | 0 | 0 | 0 | | |
| | 7 | Female | 0 | 0 | 0 | | |
| | 8 | Female | 0 | 0 | 0 | | |
| | 9 | Female | 0 | 0 | 0 | | |
| | 10 | Female | 0 | 0 | 0 | | |
| Test Article (CSO Extract) | 11 | Male | 0 | 0 | 0 | 0% | Weak |
| | 12 | Male | 0 | 0 | 0 | | |
| | 13 | Male | 0 | 0 | 0 | | |
| | 14 | Male | 0 | 0 | 0 | | |
| | 15 | Male | 0 | 0 | 0 | | |
| | 16 | Female | 0 | 0 | 0 | | |
| | 17 | Female | 0 | 0 | 0 | | |
| | 18 | Female | 0 | 0 | 0 | | |
| | 19 | Female | 0 | 0 | 0 | | |
| | 20 | Female | 0 | 0 | 0 | | |
| Negative Control (NaCl) | 21 | Male | 0 | 0 | 0 | 0% | Weak |
| | 22 | Male | 0 | 0 | 0 | | |
| | 23 | Female | 0 | 0 | 0 | | |
| | 24 | Female | 0 | 0 | 0 | | |
| | 25 | Female | 0 | 0 | 0 | | |
| Negative Control (CSO) | 26 | Male | 0 | 0 | 0 | 0% | Weak |
| | 27 | Male | 0 | 0 | 0 | | |
| | 28 | Female | 0 | 0 | 0 | | |
| | 29 | Female | 0 | 0 | 0 | | |
| | 30 | Female | 0 | 0 | 0 | | |
| Positive Control (DNCB) | 31 | Male | 2 | 1 | 0 | 100% | Extreme |
| | 32 | Male | 2 | 2 | 1 | | |
| | 33 | Female | 3 | 2 | 1 | | |
| | 34 | Female | 3 | 2 | 1 | | |
| | 35 | Female | 3 | 3 | 2 | | |

| Sensitization Rate (%) | Grade | Class |
|---|---|---|
| 0-8 | I | Weak |
| 9-28 | II | Mild |
| 29-64 | III | Moderate |
| 65-80 | IV | Strong |
| 81-100 | V | Extreme |

The test results are interpreted based upon the percentage sensitization observed.

7. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. A composition comprising shortened poly-β-1→4-N-acetylglucosamine fibers, wherein the shortened poly-β-1→4-N-acetylglucosamine fibers comprise at least 70% N-acetylglucosamine monosaccharides, wherein the shortened poly-β-1→4-N-acetylglucosamine fibers have the microstructure of non-irradiated poly-β-1→4-N-acetylglucosamine fibers that are about 100 µm in length, and wherein the shortened poly-β-1→4-N-acetylglucosamine fibers are less than 10 µm in length.

2. The composition of claim 1, wherein the shortened poly-β-1→4-N-acetylglucosamine fibers are from about 2 µm to less than 10 µm in length.

3. The composition of claim 1, wherein the shortened poly-β-1→4-N-acetylglucosamine fibers have the microstructure of non-irradiated microalgal poly-β-1→4-N-acetylglucosamine fibers that are about 100 µm in length.

4. The composition of claim 1, wherein the shortened poly-β-1→4-N-acetylglucosamine fibers are between about 2 µm to less than 10 µm in average length.

5. The composition of claim 1, wherein the shortened poly-β-1→4-N-acetylglucosamine fibers are between about 4 µm to less than 10 µm in average length.

6. The composition of claim 1, wherein at least 75% of the composition consists of the shortened poly-β-1→4-N-acetylglucosamine fibers.

7. The composition of claim 1, wherein the length of the fibers is determined by scanning electron microscopic (SEM) analysis.

8. The composition of claim 1, wherein the poly-β-1→4-N-acetylglucosamine is a microalgal poly-β-1→4-N-acetylglucosamine.

9. The composition of claim 1, wherein the poly-β-1→4-N-acetylglucosamine is not a crustacean poly-β-1→4-N-acetylglucosamine.

10. The composition of claim 2, wherein the shortened poly-β-1→4-N-acetylglucosamine fibers comprise at least 80% N-acetylglucosamine monosaccharides.

11. The composition of claim 2, wherein the shortened poly-β-1→4-N-acetylglucosamine fibers comprise at least 90% N-acetylglucosamine monosaccharides.

12. The composition of claim 1, wherein the shortened poly-β-1→4-N-acetylglucosamine fibers comprise 100% N-acetylglucosamine monosaccharides.

13. The composition of claim 1, wherein the shortened poly-β-1→4-N-acetylglucosamine fibers are biocompatible as determined by an elution test, an intramuscular implantation test, or intracutaneous or systemic injection into animal subjects.

14. The composition of claim 13, wherein the shortened poly-β-1→4-N-acetylglucosamine fibers are biocompatible as determined by the intramuscular implantation test, wherein the intramuscular implantation test is a 4 week implantation into paravertebral muscle tissue of a rabbit based on International Organization for Standardization Guidelines, and wherein the shortened poly-β-1→4-N-acetylglucosamine fibers are non-reactive when tested in the intramuscular implantation test.

15. The composition of claim 1, wherein the composition is in a form of a dressing, a barrier, a membrane, a film, a bandage, a gauze, or a mat.

16. The composition of claim 1, which further comprises one or more antimicrobial agents.

17. The composition of claim 1, wherein the shortened poly-β-1→4-N-acetylglucosamine fibers have been produced by irradiation of poly-β-1→4-N-acetylglucosamine fibers.

18. The composition of claim 17, wherein (i) the poly-N-acetylglucosamine fibers have been irradiated in the form of dry fibers, a dry fiber membrane or a dry lyophilized material at 500-2,000 kgy, or (ii) the poly-N-acetylglucosamine fibers have been irradiated in the form of a suspension, a slurry or a wet cake at 100-500 kgy.

19. The composition of claim 18, wherein the irradiation is gamma irradiation.

20. The composition of claim 17, wherein (i) the poly-N-acetylglucosamine fibers have been irradiated by gamma irradiation in the form of dry fibers, a dry fiber membrane or a dry lyophilized material at 750-1,250 kgy, or (ii) the poly-N-acetylglucosamine fibers have been irradiated by gamma irradiation in the form of a suspension, a slurry or a wet cake at 150-250 kgy.

21. The composition of claim 1, wherein the composition increases metabolic rate of serum-starved human umbilical cord vein endothelial cells in a MTT (3-(4,5-Dimethylthiazol-2-yl)-2,5-diphenyltetrazolium bromide) assay, and/or does not rescue apoptosis of serum-starved human umbilical cord vein endothelial cells in a trypan blue exclusion test.

22. The composition of claim 1, which produces no detectable foreign body reaction after exposing a wound of a patient or an animal to the composition for the duration of four weeks, wherein the foreign body reaction is characterized by the formation of foreign body giant cells, encapsulation of the foreign object, and/or chronic inflammation, wherein the encapsulation refers to the firm, generally avascular collagen shell deposited around a foreign body.

23. A composition comprising shortened poly-$\beta$-1→4-N-acetylglucosamine fibers, wherein the shortened poly-$\beta$-1→4-N-acetylglucosamine fibers comprise at least 70% N-acetylglucosamine monosaccharides, wherein the shortened poly-$\beta$-1→4-N-acetylglucosamine fibers are less than 10 µm in average length, and wherein the shortened poly-$\beta$-1→4-N-acetylglucosamine fibers have the chemical and physical structure of microalgal-derived poly-$\beta$-1→4-N-acetylglucosamine nanofibers that average 20-50 nm×1-2 nm×100 µm in dimension as determined by infrared (IR) spectrum, elemental assay and scanning electron microscopic (SEM) analyses.

24. The composition of claim 23, wherein the shortened poly-$\beta$-1→4-N-acetylglucosamine fibers are from about 2 µm to less than 10 µm in average length.

25. The composition of claim 23, wherein the poly-$\beta$-1→4-N-acetylglucosamine is a microalgal poly-$\beta$-1→4-N-acetylglucosamine.

26. The composition of claim 23, wherein the shortened poly-$\beta$-1→4-N-acetylglucosamine fibers comprise at least 90% N-acetylglucosamine monosaccharides.

27. A composition comprising shortened poly-$\beta$-1→4-N-acetylglucosamine fibers, wherein the shortened poly-$\beta$-1→4-N-acetylglucosamine fibers comprise at least 70% N-acetylglucosamine monosaccharides, wherein the shortened poly-$\beta$-1→4-N-acetylglucosamine fibers are from about 2 µm to less than 10 µm in average length, and wherein the shortened poly-$\beta$-1→4-N-acetylglucosamine fibers have the microstructure of non-irradiated microalgal poly-$\beta$-1→4-N-acetylglucosamine fibers.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Ets1 forward primer for RT-PCR

<400> SEQUENCE: 1
ttctcagagc ccagcttcat                                         20

<210> SEQ ID NO 2
<211> LENGTH: 21
<212> TYPE: DNA
<213> ORGANISM: Artificial Sequence
<220> FEATURE:
<223> OTHER INFORMATION: Ets1 reverse primer for RT-PCR

<400> SEQUENCE: 2
aaagtttgaa ttcccagcca t                                       21

<210> SEQ ID NO 3
<211> LENGTH: 20
<212> TYPE: DNA
<213> ORGANISM: Artificial Sequence
<220> FEATURE:
<223> OTHER INFORMATION: metallothionein 2A forward primer for RT-PCR

<400> SEQUENCE: 3
caacctgtcc cgactctagc                                         20
```

<210> SEQ ID NO 4
<211> LENGTH: 20
<212> TYPE: DNA
<213> ORGANISM: Artificial Sequence
<220> FEATURE:
<223> OTHER INFORMATION: metallothionein 2A reverse primer for RT-PCR

<400> SEQUENCE: 4
aggagcaact cctgtcctga                                        20

<210> SEQ ID NO 5
<211> LENGTH: 20
<212> TYPE: DNA
<213> ORGANISM: Artificial Sequence
<220> FEATURE:
<223> OTHER INFORMATION: S26 forward primer for RT-PCR

<400> SEQUENCE: 5
ctccggtccg tgcctccaag                                        20

<210> SEQ ID NO 6
<211> LENGTH: 21
<212> TYPE: DNA
<213> ORGANISM: Artificial Sequence
<220> FEATURE:
<223> OTHER INFORMATION: S26 reverse primer for RT-PCR

<400> SEQUENCE: 6
cagagaatag cctgtcttca g                                      21

<210> SEQ ID NO 7
<211> LENGTH: 20
<212> TYPE: DNA
<213> ORGANISM: Artificial Sequence
<220> FEATURE:
<223> OTHER INFORMATION: VEGF forward primer for RT-PCR

<400> SEQUENCE: 7
ctacctccac catgccaagt                                        20

<210> SEQ ID NO 8
<211> LENGTH: 19
<212> TYPE: DNA
<213> ORGANISM: Artificial Sequence
<220> FEATURE:
<223> OTHER INFORMATION: VEGF reverse primer for RT-PCR

<400> SEQUENCE: 8
tggtgatgtt ggctcctca                                         19

<210> SEQ ID NO 9
<211> LENGTH: 20
<212> TYPE: DNA
<213> ORGANISM: Artificial Sequence
<220> FEATURE:
<223> OTHER INFORMATION: IL-1 forward primer for RT-PCR

<400> SEQUENCE: 9
ctgcgccaac acagaaatta                                        20

<210> SEQ ID NO 10
<211> LENGTH: 20
<212> TYPE: DNA
<213> ORGANISM: Artificial Sequence
<220> FEATURE:

```
<223> OTHER INFORMATION: IL-1 reverse primer for RT-PCR

<400> SEQUENCE: 10
attgcatctg gcaaccctac                                               20

<210> SEQ ID NO 11
<211> LENGTH: 20
<212> TYPE: DNA
<213> ORGANISM: Artificial Sequence
<220> FEATURE:
<223> OTHER INFORMATION: IL-8 forward primer for RT-PCR

<400> SEQUENCE: 11
tcggatttca cgatttctcc                                               20

<210> SEQ ID NO 12
<211> LENGTH: 20
<212> TYPE: DNA
<213> ORGANISM: Artificial Sequence
<220> FEATURE:
<223> OTHER INFORMATION: IL-8 reverse primer for RT-PCR

<400> SEQUENCE: 12
gctacaagtg cgtcgtcaaa                                               20
```